(12) United States Patent
Desinger

(10) Patent No.: US 7,094,233 B2
(45) Date of Patent: Aug. 22, 2006

(54) HOLLOW SURGICAL PROBE

(76) Inventor: Kai Desinger, Rubensstrasse 108, Berlin, D-12157 (DE)

( * ) Notice: Subject to any disclaimer, the term of this patent is extended or adjusted under 35 U.S.C. 154(b) by 258 days.

(21) Appl. No.: 10/276,836

(22) PCT Filed: May 22, 2001

(86) PCT No.: PCT/EP01/05880

§ 371 (c)(1),
(2), (4) Date: Nov. 19, 2002

(87) PCT Pub. No.: WO01/89388

PCT Pub. Date: Nov. 29, 2001

(65) Prior Publication Data

US 2004/0097920 A1  May 20, 2004

(30) Foreign Application Priority Data

May 24, 2000  (DE) ......................... 100 26 508

(51) Int. Cl.
*A61B 18/18* (2006.01)

(52) U.S. Cl. .................. 606/45; 606/167; 600/564; 600/567

(58) Field of Classification Search ............ 606/41, 606/42, 45–50, 32, 39, 40, 167; 604/21, 22; 600/564, 567
See application file for complete search history.

(56) References Cited

U.S. PATENT DOCUMENTS

| 1,639,996 A | * | 8/1927 | Groff ..................... 606/45 |
| 5,749,869 A | | 5/1998 | Lindenmeier |
| 5,775,333 A | | 7/1998 | Burbank |
| 5,782,795 A | | 7/1998 | Bays |
| 5,810,806 A | | 9/1998 | Ritchart |
| 5,817,034 A | | 10/1998 | Milliman |
| 6,050,955 A | | 4/2000 | Bryan |
| 6,261,241 B1 | | 7/2001 | Burbank |
| 6,331,166 B1 | | 12/2001 | Burbank |

FOREIGN PATENT DOCUMENTS

| DE | 38 30 193 C2 | 10/1990 |
| DE | 197 06 751 A1 | 10/1997 |
| DE | 195 28 440 C2 | 9/1998 |
| EP | 0 761 170 A2 | 3/1997 |
| EP | 0 919 192 A2 | 6/1999 |
| GB | 2 311 468 A | 10/1997 |
| WO | WO 96/14018 A1 | 5/1996 |
| WO | WO 98/08441 A1 | 3/1998 |
| WO | WO 99/44506 A1 | 9/1999 |
| WO | WO 00/16697 A2 | 3/2000 |

* cited by examiner

*Primary Examiner*—Rosiland Rollins
(74) *Attorney, Agent, or Firm*—Hahn Loeser & Parks, LLP; Robert J. Clark

(57) ABSTRACT

A hollow surgical probe for the minimally invasive removal of tissue has an elongate hollow body and an electrical conductive ring-shaped or loop-shaped cutting element. The elongate hollow body includes two segments of which at least one encloses a cavity for receiving tissue and which can be separated from each other and which are movably relative to each other in such a way that an opening between the segments is to be selectively opened or closed. The electrically conductive ring-shaped or loop-shaped cutting element is movable relative to at least one of the segments and is adapted for electrosurgically cutting out tissue which has penetrated into the opening between the hollow body segments.

36 Claims, 65 Drawing Sheets

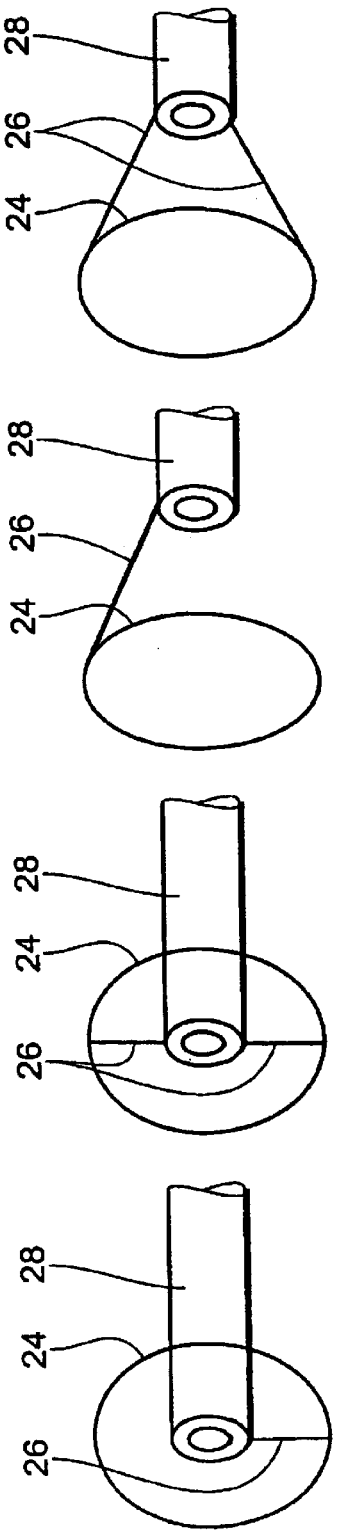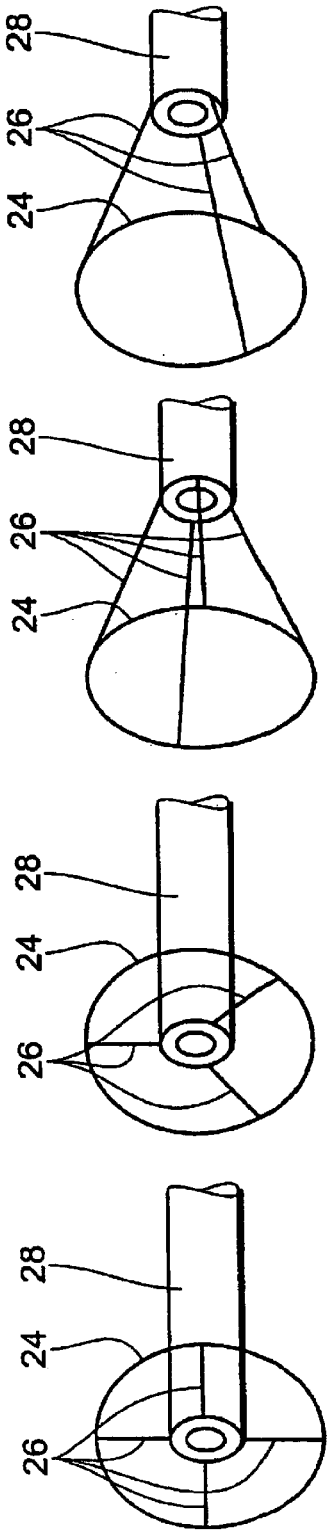
Fig. 10a Fig. 10b Fig. 10c Fig. 10d Fig. 10e Fig. 10f Fig. 10g Fig. 10h

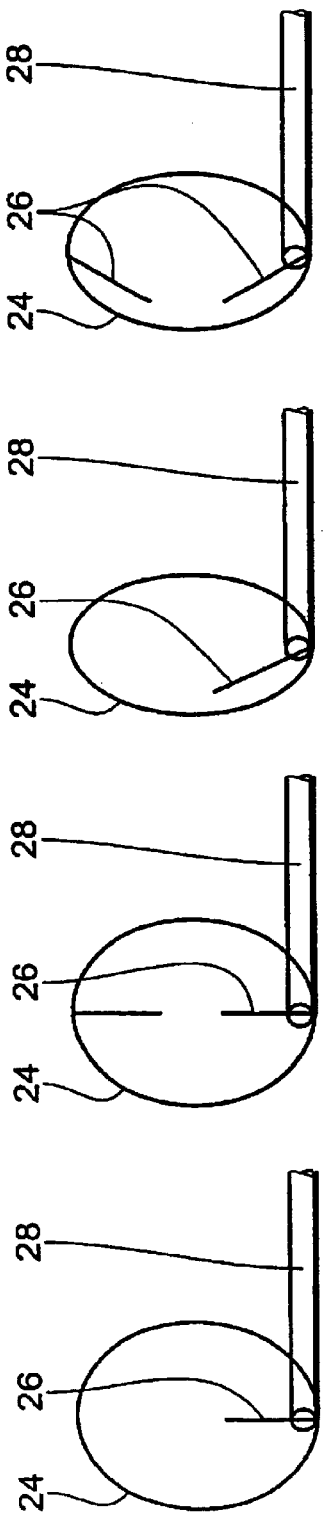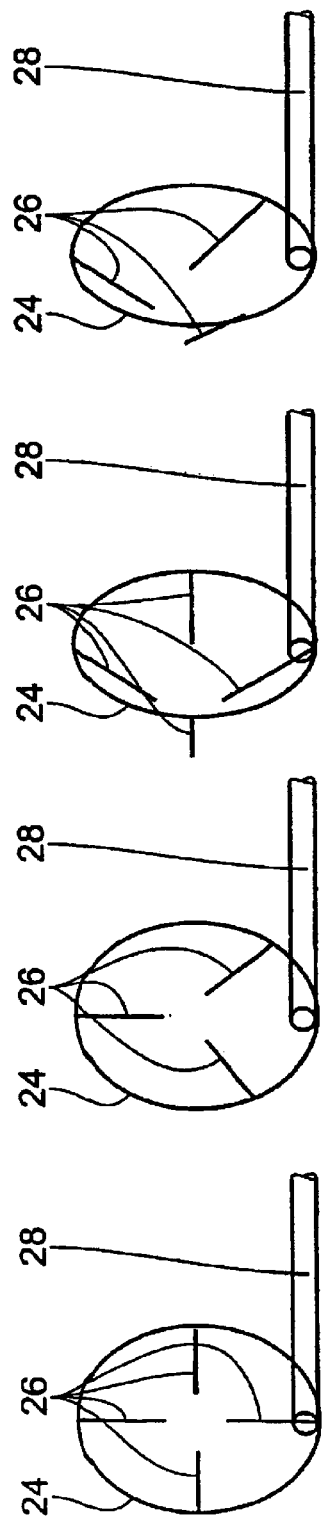

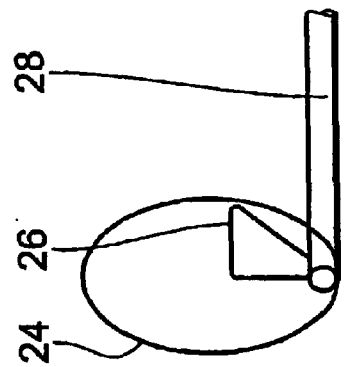
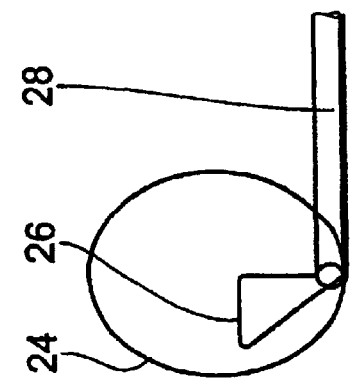
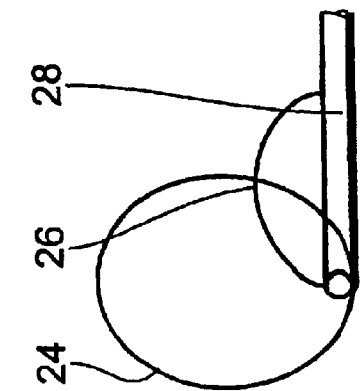

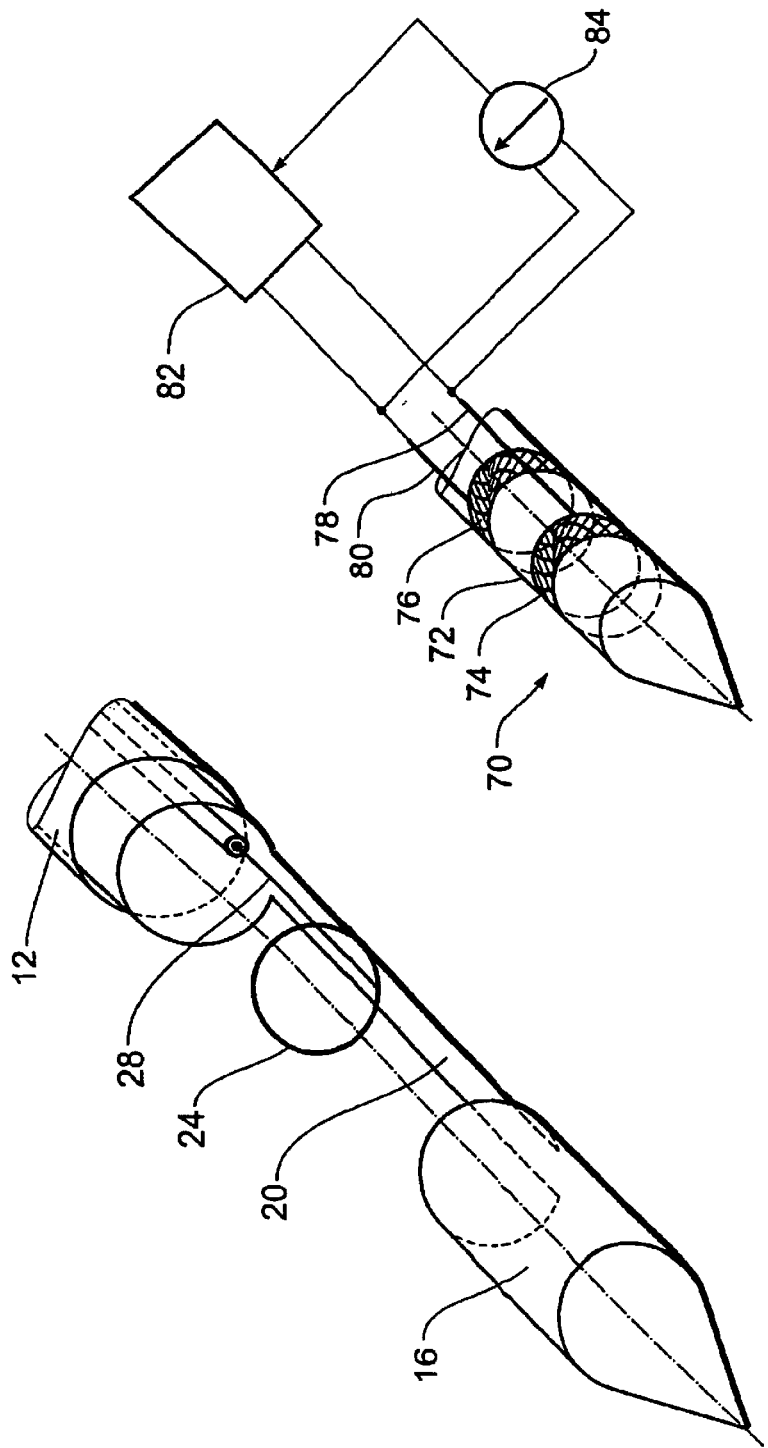

HOLLOW SURGICAL PROBE

This application is a 371 of PCT/EP01/05880 filed May 22, 2001.

The invention concerns a hollow surgical probe for the minimally invasive removal of tissue comprising an elongate hollow body which includes two segments of which at least one encloses a cavity for receiving tissue and which can be separated from each other and which are arranged movably relative to each other in such a way that an opening between the segments is to be selectively opened or closed.

BACKGROUND OF THE ART

In the context of minimally invasive medicine the endeavor is to carry out an operation which causes the minimum degree of trauma to the patient. In that respect the endeavor is to gain access to the depth of the tissue either by way of the natural body openings of the patient as in the case of interventional endoscopy by way of instruments (endoscope) with visual control or however by way of small incisions directly at the location of intervention, in order there to remove tissue for diagnostic purposes, for example for histological tissue determination or for therapy purposes, for example for tumor removal.

In recent years the development of suitable instruments for minimally invasive surgery has been the subject of rapid progress as that operating technique affords considerably advantages for cosmetic reasons, for minimizing post-operative complications and for speeding up the healing process.

Apparatuses are known by the name "Fine needle aspiration" (FNA) or "true cut needle biopsy", which have a fine needle which is introduced into a suspicious area of tissue and by means of which one or more tissue samples can be removed purely mechanically by way of a cutting or perforating mechanism in order to subject that tissue to histological examination.

Thereafter possibly in the event of malignant findings suitable surgical measures can be initiated. The volumes of tissue which can be removed with those needle probes however are only very small and are therefore suitable exclusively for diagnostic purposes. By virtue of the small volume of tissue which can be removed in one puncture insertion a plurality of puncture insertions into the suspicious area of tissue are therefore often required, which under some circumstances can result in spreading of malignant tumor cells. In addition the degrees of accuracy of the histological tissue results are not optimum, by virtue of the small volume of tissue involved.

U.S. Pat. Nos. 5,775,333 and 5,782,795 disclose surgical instruments which permit larger volumes of tissue to be removed by virtue of multiple tissue removal from the same target area. Those known instruments use a vacuum-supported mechanical punching-cutting device which reduces the number of puncture insertions required and which in addition also improves the level of accuracy of the diagnostic findings, by virtue of the larger volume of tissue. It is also often possible with those known instruments for relatively small changes in tissue to be already removed in toto, which under some circumstances makes a subsequent operation unnecessary.

In the case of the instrument in accordance with U.S. Pat. No. 5,775,333 a needle-shaped hollow probe is introduced into the target area, for example a breast tumor. Disposed laterally at the end of the probe is an elongate opening into which the tissue to be removed is sucked. Disposed within the apparatus is a rotating hollow blade which by the way of a mechanical advance cuts off the tissue which has been sucked into the opening, within the apparatus, and sucks it away through the hollow probe by means of a vacuum. By successive rotation of the shaft through 360° a given volume of tissue which has been previously sucked into the hollow probe and cut away is removed around the distal end of the probe, which however is often not entirely sufficient for complete removal of the medically suspicious area of tissue.

U.S. Pat. No. 5,817,034 discloses a surgical instrument in which a tubular cylindrical blade of a diameter of up to 25 mm is advanced as far as the target area. The head portion of the cylinder which is thus punched out within the apparatus is severed by way of a loop which is disposed at the end and which is subjected to the action of HF-voltage, and then the entire severed cylinder of tissue is removed by way of the apparatus. Admittedly that known system can provide that the suspicious area of tissue can be removed in toto, but also a great deal of healthy tissue is removed, until the tip of the probe has reached the suspicious area of tissue, and a relatively large scar is then left behind by virtue of the large diameter of the apparatus.

U.S. Pat. No. 5,810,806 discloses a surgical probe in which the tissue is not cut into by means of a mechanical annular blade but by means of an axially immovable loop which is fixed at the distal end of the hollow body and which is supplied with an HF-voltage and thereby acts as a cutting blade. In a cutting operation the cylinder of tissue which is cut off at the periphery by the HF-loop is displaced frontally into the forwardly open hollow body and then is severed at the end of the procedure by a windshield wiper-like rotary movement of the loop which is subjected to the action of HF-voltage. That known apparatus also provides that the tissue is completely severed only when it is in the hollow body, whereby a great deal of healthy tissue is also removed therewith until the tip of the probe has been advanced as far as the suspicious area of tissue. A further disadvantage is that only the cylinder of tissue in front of the front opening of the hollow body can be removed.

German applications 197 06 751 and 195 28 440 disclose an electrosurgical device of the kind set forth in the opening part of this specification, in which a loop-shaped cutting element is adapted for electrosurgically cutting out tissue in parallel relationship with the longitudinal axis of an elongate hollow body and while retaining that orientation can be moved in a loop shape out of the hollow body so that then the adjoining tissue can be cut out in a toric shape by virtue of rotation of the hollow probe. The tissue which is cut out can then be introduced into the hollow passage of the hollow body through the same opening through the cutting element issues, and can then be transported along the hollow passage to the proximal end of the device. That known device has the advantage that the puncture location is of small dimensions and that it is then possible to take at the treatment location a piece of tissue which surrounds the hollow probe in externally adjoining relationship therewith. A disadvantage in this case however is that the volume of tissue which can be cut out is relatively is small and is therefore not sufficient for thorough examination of even larger regions of tissue.

PCT application WO 99/44506 issued as U.S. Pat. No. 6,331,166, discloses a loop-shaped cutting element which can be moved out of the hollow body in a plane which extends transversely with respect to the longitudinal axis of the hollow body, wherein after the cutting element has been moved out of the hollow body it is displaceable along the hollow body.

U.S. Pat. No. 5,810,659 discloses a surgical probe for removing tissue, in which the distal end of a shaft carries a sharply ground cutting sleeve to which a HF-voltage can be applied. Disposed distally behind the cutting sleeve, at a guide wire extending centrally through the catheter, is a ceramic body as a counterpart support for the cutting sleeve, at the end of which a rounded-off metal electrode is fixed and connected by way of the guide wire to a HF-generator. By way of an operating member, the cylindrical counterpart support can be moved by way of the guide wire to the sharply ground metal sleeve, in which case the tissue disposed therebetween is purely mechanically severed by the sharp ground portion of the metal sleeve and is thus collected within the proximal cutting sleeve. Both the proximal sleeve and also the metal electrode fixed to the counterpart support are connected to an HF-generator and thus permit bipolar coagulation of tissue in order possibly also to stop bleeding. That however does not involve a technical solution for easily removing the biopsate once collected. The tissue has to be removed from the sleeve in a complicated procedure using micro-tweezers or a needle.

PCT published application PCT/US99/21416 now U.S. Pat. No. 6,261,241, discloses a rigid surgical instrument, which also comprises a sleeve configuration displaceable relative to each other in order to remove tissue samples and to coagulate the tissue. The novelty in relation to the state of the art lies on the one hand in the complicated and expensive, partly automated operating member, and in the possibility of applying a cutting current to one of the two displaceable sleeves in order to electrosurgically cut off the tissue. In a further embodiment the cutting operation is not implemented by way of the sleeve itself, but a fixed cutting electrode which is let into the casing at the proximal periphery of the sleeve.

SUMMARY OF THE INVENTION

The object of the invention is to provide a surgical probe of the kind set forth in the opening part of this specification, which while avoiding the disadvantages of the state of the art is easy and reliable to handle.

That object is attained by a surgical hollow probe which has an electrically conductive ring-shaped or loop-shaped cutting element which is movable relative to at least one of the segments and which is adapted for electrosurgically cutting out tissue which has penetrated into the opening between the hollow body segments, and in addition an ejector for ejecting tissue from the hollow probe.

Such a hollow probe makes it possible in particular to move the cutting element into a particularly preferred exposed position. If then a high frequency voltage is applied to the cutting element as is intended, then by virtue of the field concentration around the cutting element the tissue directly adjoining the cutting element is heated. With the cutting element being exposed, that heating effect can be to such an extent that a vapor cushion is formed around the cutting element so that the cutting element can penetrate in a practically contact-less manner through the tissue. It has been found that such an effect in which the cutting element is completely surrounded by a vapor cushion, in the case of an electrode which is let into the front end of a sleeve as is known from PCT/US99/21416, does not occur or occurs only when greater field strengths are involved.

Due to the applied high frequency voltage (>200 V) the cutting electrode which is in the form of a wire loop or wire noose produces many small spark discharges along the electrode. That results in the production of a vapor cushion between the tissue and the electrode, which permits virtually contact-free electrical cutting. The use of a rather sinusoidal high-frequency alternating current makes it possible to produce cuts in the tissue with minimal thermal edge coagulation. Different degrees of coagulation can be adjusted at the cut surface by altering the so-called crest factor, that is to say the ratio of peak voltage to effective voltage and additional HF-modulation. In an embodiment of the invention the return of the current is effected by way of one or more functional surfaces on the hollow body. Patient-safe and low-pain interventions can be carried out with a low generator output, with that bipolar electrode configuration. This probe is also to be operated however in a monopolar configuration, with a return electrode which can be applied to the patient extremity.

In addition the hollow probe according to the invention permits tissue which has been removed to be easily ejected. That is effected by an ejector which is integrated into the probe so that a special tool is not required for the removal of tissue from the hollow probe.

Preferably the two segments of the hollow probe can be separated from each other along a peripheral line around the cavity. The two segments are then preferably axially displaceable relative to each other. In a preferred embodiment the separation line between the two segments extends near the distal end of the hollow probe. In a hollow probe preferably one segment is formed by the tip of the hollow probe while the second segment is a sleeve which is axially displaceable with respect to the tip and which is of round, oval or polygonal cross-section. After insertion of the hollow probe into tissue a displaceable sleeve can be withdrawn, so that, depending on respective cross-sectional shape of the sleeve, that affords a cylindrical or prism-shaped opening between the tip of the hollow probe and the sleeve.

Preferably that displaceability is achieved by a thrust rod which is fixedly connected to the tip and longitudinally guided in the sleeve. The thrust rod can either extend centrally in a cavity enclosed by the sleeve or near the wall of the sleeve.

The first-mentioned variant affords the advantage of a symmetrical distribution of forces while the second-mentioned variant affords the advantage that the cavity defined by the sleeve does not extend around the thrust rod but the thrust rod is disposed entirely at one side of the cavity. That affords advantages in terms of ejection of body tissue which has been removed with the hollow probe.

In a particularly preferred feature the distal end of the hollow probe converges to a point and carries a first electrode which, when cutting out tissue, can serve as a counterpart electrode for the cutting element. In the cutting operation in that case one terminal of the HF-voltage source is applied to the cutting element and the other terminal to the first electrode. Upon insertion of the probe the cutting element lies passively without being subjected to voltage in the interior of the hollow body.

The cutting element is preferably formed by a wire loop which is round, oval or of a polygonal shape and which defines a plane and which is guided perpendicularly to that plane relative to at least one of the segments axially displaceably by means of preferably a thrust rod. Such a wire loop has the property of being electrically conductive and can thus serve as an electrode for the application of an electrical high-frequency voltage. The counterpart electrode can represent for example the one segment which is formed by the tip of the hollow probe or the other segment of the hollow probe which is formed by the displaceable sleeve. If the wire for the cutting element is of a diameter of between 0.05 and 1 mm, preferably about 0.15 mm, the counterpart electrode can easily be of a substantially larger surface area than the cutting element so that an electrical field between the cutting element and the counterpart electrode is concentrated around the cutting element. That desired field concentration effect has the result that the above-described formation of a vapor bubble occurs only around the cutting element.

In a preferred embodiment the wire loop or wire noose comprises a cutting wire which is bent in a ring shape and which is connected to a central tubular bar or sleeve by way of one or more cutting wires which are arranged in a spoke configuration. By moving the central sleeve forward and back the ring electrode can be pushed through the tissue and rotated around the central axis to cut out or cut into tissue.

Particularly in the situation where the thrust rod connecting the two segments extends centrally in the cavity, it is advantageous if a further wire serving as a cutting electrode is provided between the wire loop and the thrust rod, so that for example a portion of tissue which embraces the thrust rod in a toric-like configuration can also be cut out at the side.

In such a variant the cutting electrode is connected at its periphery to a bar-shaped body which is arranged at a right angle thereto, as the thrust rod, while the thrust rod connecting the two segments extends centrally substantially through the center point of the wire loop. Loops or spokes disposed between the central thrust rod and the ring electrode which is in the form of the wire loop serve for cutting into the toric tissue samples to be removed, the loops or spokes permitting subsequent removal of the sample. In that situation the thrust rod for the wire loop is supported displaceably within the hollow body and is in the form for example of a shaped body or is supported non-rotatably by other known measures. In this embodiment the cutting electrode is not rotatable.

The cutting element is connected to an HF-voltage source by way of a connecting line which is guided for example along the inside wall of the hollow body. The HF-voltage source is disposed at the proximal end of the hollow probe. The other terminal of the HF-voltage source is connected to a counterpart electrode which is either applied from the exterior to the skin of the patient or—in order to prevent an uncontrolled flow of current through the tissue—is disposed at the hollow body or part thereof. If the hollow body is made from metal the entire hollow body of the hollow probe can also serve as the counterpart electrode, thereby affording a controlled, locally closely restricted flow of current from the cutting element to the counterpart electrode. In that case however they both have to be well electrically insulated from each other in order to avoid a short-circuit.

In addition the two segments are preferably in the form of electrodes to which the high-frequency voltage can be applied for thermal inactivation of tissue. An insulating element can be disposed for that purpose between the two segments.

In a particularly preferred feature during the insertion procedure the first electrode which is preferably formed by the metal tip is subjected to the action of HF-voltage and a counterpart electrode is applied from the exterior to the patient in the proximity of the area of tissue to be investigated. The tissue adjoining the probe is then thermally inactivated by means of a locally restricted, high-frequency alternating current over an individually predeterminable period of time. If in addition a second electrode is applied to the hollow body at a predetermined axial spacing the high-frequency alternating field can be produced between the two—preferably cylindrical—electrodes whereby the alternating field—upon insertion of the probe—is locally restricted to immediately adjoining zones of tissue. The counterpart electrode which is applied from the exterior can then be omitted. In that case the HF-voltage is so fixed that temperatures of between 55° and 100° C., preferably between 60° and 80° C., can be maintained in the tissue over a relatively long period of time of for example between 5 and 20 minutes, in order thus irreversibly to terminate the metabolic processes within the tumor cells. That thermal inactivation effect ensures that in the subsequent removal of tissue the tumor cells can no longer spread and metastasize.

Particularly preferred is an electrical apparatus which includes a hollow probe of the described kind with two electrodes arranged at or in the immediate proximity of the hollow probe for the introduction of high-frequency current into the tissue surrounding the hollow probe, which is connected to an apparatus for measuring the impedance between the two electrodes. Such an apparatus makes it possible to measure the impedance between the two electrodes during the introduction of the high-frequency current. That can be effected by detecting the current strength, voltage or the thread angle. The power effectively introduced into the tissue can also be calculated.

Impedance measurement during the introduction of the high-frequency current makes it possible to determine in particular the specific resistance of that tissue which surrounds the hollow probe. Unlike the situation involving a monopolar procedure with a counterpart or neutral electrode which is externally applied to the body and at which the entire peripheral tissue resistance is measured, in the case of the bipolar procedure which is preferred here it is the real, local, specific tissue resistance between the electrodes that is measured. The data obtained in that way are preferably fed to a power or impedance regulator for a generator which serves to produce the electrical power to be introduced into the tissue. The generator power is always matched to the respectively current tissue status by impedance or tissue resistance-dependent regulation. In addition the respectively obtained data can also be displayed for example acoustically or optically as information about the respectively current tissue status. That affords a surgeon for example the option of adapting the treatment with the hollow probe presented here individually and currently to the respectively notified tissue status.

The ejector is preferably a piston-like body which is arranged longitudinally slidably in the manner of a ram in the cavity and which in its rest position is preferably disposed at an end of the cavity and which is displaceable out of that rest position in the direction of the cavity in order to be able to eject tissue in the cavity when the cavity is opened upon displacement of the segments. If such tissue were intended in the manner of a torus for example to embrace a thrust rod for one of the segments, it is possible to provide on the side of the ejector associated with the cavity, one or more severing blades which cut the tissue upon ejection in such a way that the torus is no longer closed around the thrust rod.

In accordance with a preferred embodiment of the invention the ejector is a piston element which is arranged displaceably within the cavity in the proximal part of the hollow body and which is supported sealingly in relation to the metal sleeve in such a way that, after the tissue body has been cut off by way of the axially displaceable cutting element, retraction of the piston element causes the formation of a vacuum which promotes introduction of the cut-out cylinder or torus into the proximal sleeve of the hollow body.

In a further embodiment the vacuum can alternatively or additionally be produced by a separately connected vacuum pump and can be applied to the hollow body for pulling in the tissue.

Advantageous developments of the invention are characterized by the features of the appendant claims.

BRIEF DESCRIPTION OF THE DRAWINGS

Embodiments of the invention are described in greater detail hereinafter with reference to the drawings in which:

FIGS. 1a through 1l show a first embodiment of a hollow probe in various operating conditions, FIGS. 10a through 10h show various variants of a central thrust rod with a cutting loop secured thereto, FIGS. 11a through 11k show alternative variants of a decentral thrust rod with a cutting loop, FIG. 15 is a diagrammatic perspective view showing a hollow probe similar to that shown in FIG. 3, and FIG. 16 shows a surgical apparatus with a hollow probe and an HF-generator.

DETAILED DESCRIPTION OF A PREFERRED EMBODIMENT

Figure 1A:
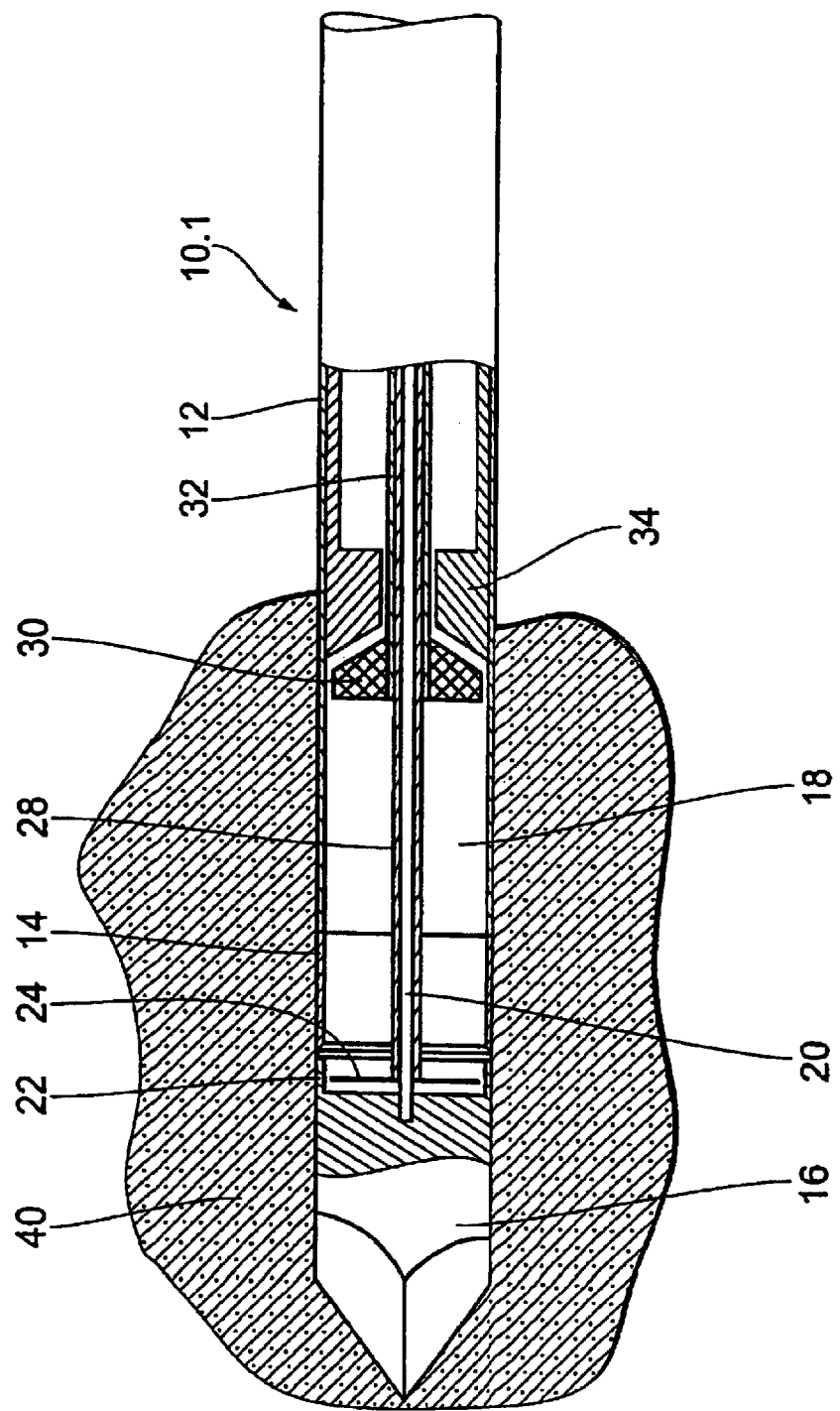

Essential components of the hollow probe 10.1 shown in FIGS. 1a through 1l are a metal sleeve 12 which is insulated at its distal end portion 14 and a metal tip 16. The metal sleeve 12 with its distal end portion 14, together with the metal tip 16, encloses a receiving space or cavity 18. The metal tip 16 is connected to the metal sleeve 12 by way of a thrust rod 20 which is supported axially slidably in the metal sleeve 12. As shown in FIGS. 1b through 1l the metal tip 16 and the metal sleeve 12 can be displace relative to each other in such a way that a cylindrical opening to the receiving space 18 is selectively produced or closed, between a collar 22 at the metal tip 16 and the distal end portion 14. The metal sleeve 12 with its distal end portion 14 in that way forms a first segment of a hollow body whose second segment is the metal tip 16 which is slidable axially relative to the first segment.

A further component of the hollow probe 10.1 is a cutting element 24 which is formed by a wire ring whose diameter is slightly smaller than the diameter of the receiving space 18. The cutting element 24 is connected by way of a wire strut 26 (not shown in FIG. 1, see FIG. 10) to a second thrust rod 28 which is axially slidably guided in the manner of a sliding sleeve on the first thrust rod 20 for the metal tip 16. In that way the cutting element 24 is also axially displaceable relative to the metal tip 16 as well as relative to the metal sleeve 12.

Also arranged in the hollow probe 10.1 is an ejector 30 which is fixed to a third thrust rod 32 which is axially slidably guided in the manner of a sliding sleeve on the second thrust rod 28. The ejector 30 is movable in the manner of a ram from the position shown in FIGS. 1a through 1i into the position shown in FIG. 1k in order to eject tissue disposed in the receiving space 18; see FIG. 1j.

The three thrust rods 20, 28 and 32 are guided in an insulating axial guide 34 which is arranged between the metal sleeve 12 and the third thrust rod 32. The axial guide 34 serves at the same time to seal off the receiving space 18 with respect to the rest of the space enclosed by the metal sleeve 12.

The mode of operation of the hollow probe 10.1 will now be described with reference to FIGS. 1a through 1l. Firstly the hollow probe 10.1 is caused to penetrate into the tissue, with the sharpened metal tip 16 leading. In the meantime firstly a high-frequency ac voltage is applied between the metal tip 16 serving as a first electrode and a large-area counterpart electrode to the body of the patient. The consequence of this is that tissue adjoining the hollow probe is thermally inactivated by means of a locally limited, high-frequency alternating current. If the hollow probe is further inserted into the tissue so that the metal sleeve 12 also penetrates into the tissue, the metal sleeve 12 can serve as a second electrode for applying the high-frequency ac voltage. In this case the metal tip 16 and the metal sleeve 12 are electrically insulated from each other by the insulating distal end portion 14 of the metal sleeve 12. If the high-frequency alternating field is bipolar between the metal tip 16 and the metal sleeve 12, the alternating field can be limited upon insertion of the metal probe locally to immediately adjoining tissue zones. The large-area counterpart electrode is then no longer required. The high-frequency voltage applied is so set that temperatures of between 55 degrees Celsius and 100 degrees Celsius, preferably between 60 degrees Celsius and 80 degrees Celsius, are produced in the tissue adjoining the hollow probe 10.1, over a period of between 5 and 20 minutes, in order in particular to irreversibly terminate metabolic processes within tumor cells. Thermal inactivation of that kind ensures that in particular tumor cells are no longer spread in the subsequent tissue removal procedure so that the risk of metastases is reduced.

Figure 1B:
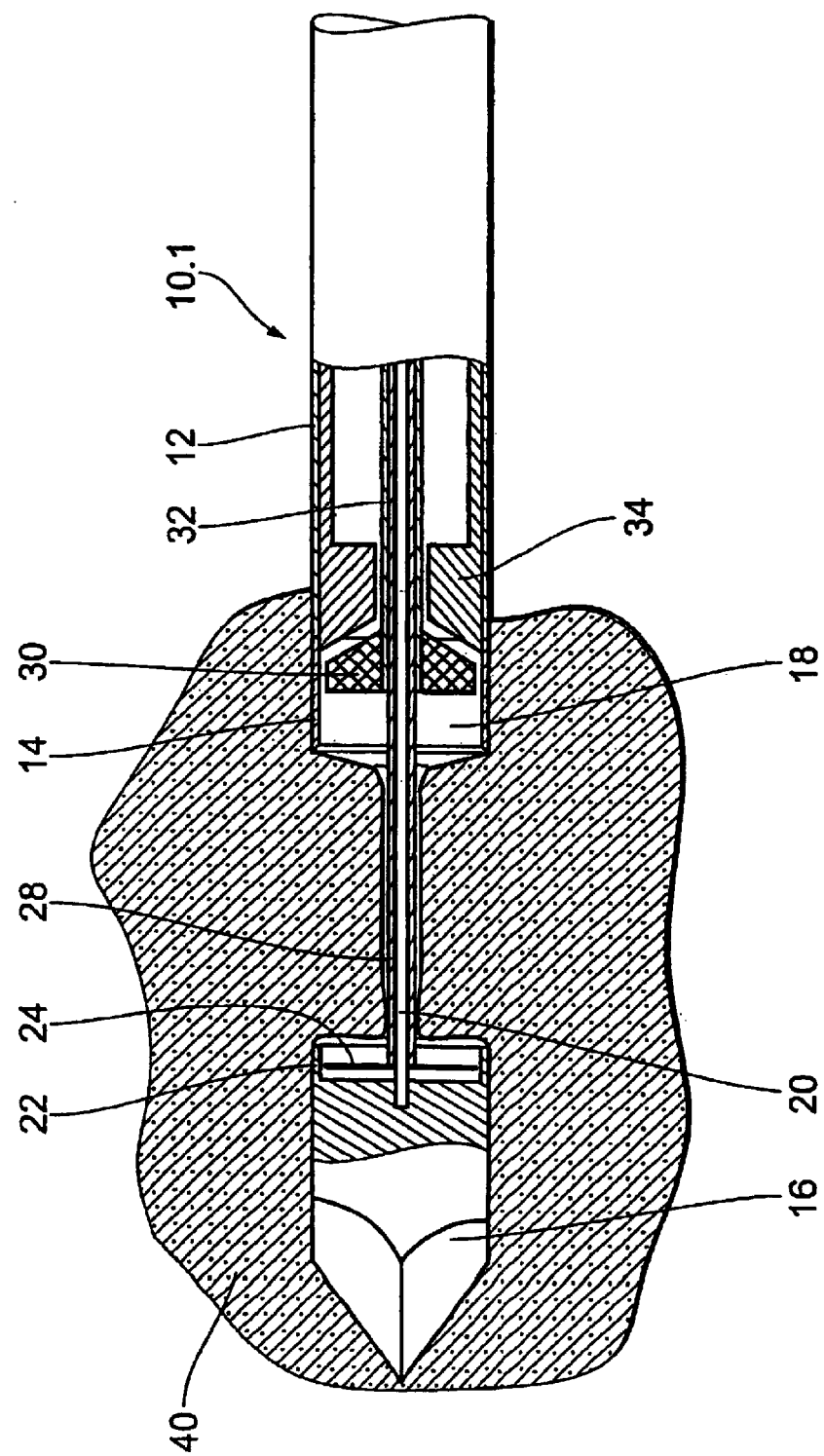

FIG. 1a shows the hollow probe 10.1 completely inserted into the tissue. After insertion of the hollow probe 10.1 the metal sleeve 12 is retracted with respect to the axial guide 34, the ejector 30, the cutting element 24 and the metal sleeve 16. In that way a cylindrical opening is afforded between the collar 22 of the metal tip 16 and the distal end portion 14 of the metal sleeve 12. The tissue which is initially displaced laterally by the hollow probe 10.1 upon insertion thereof passes in through the cylindrical opening and bears against the second thrust rod 28. That is shown in FIG. 1b.

Figure 1C:
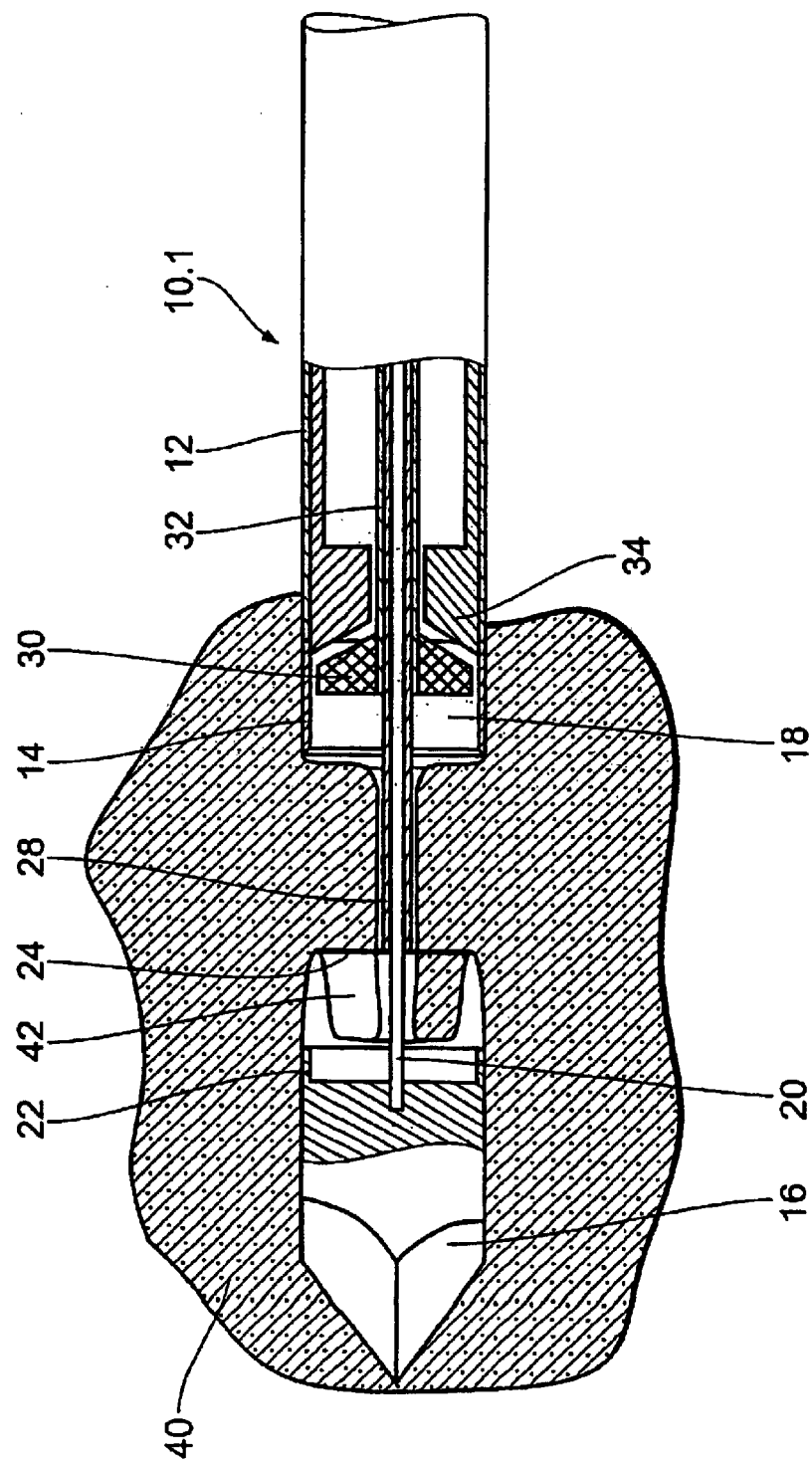
Figure 1D:
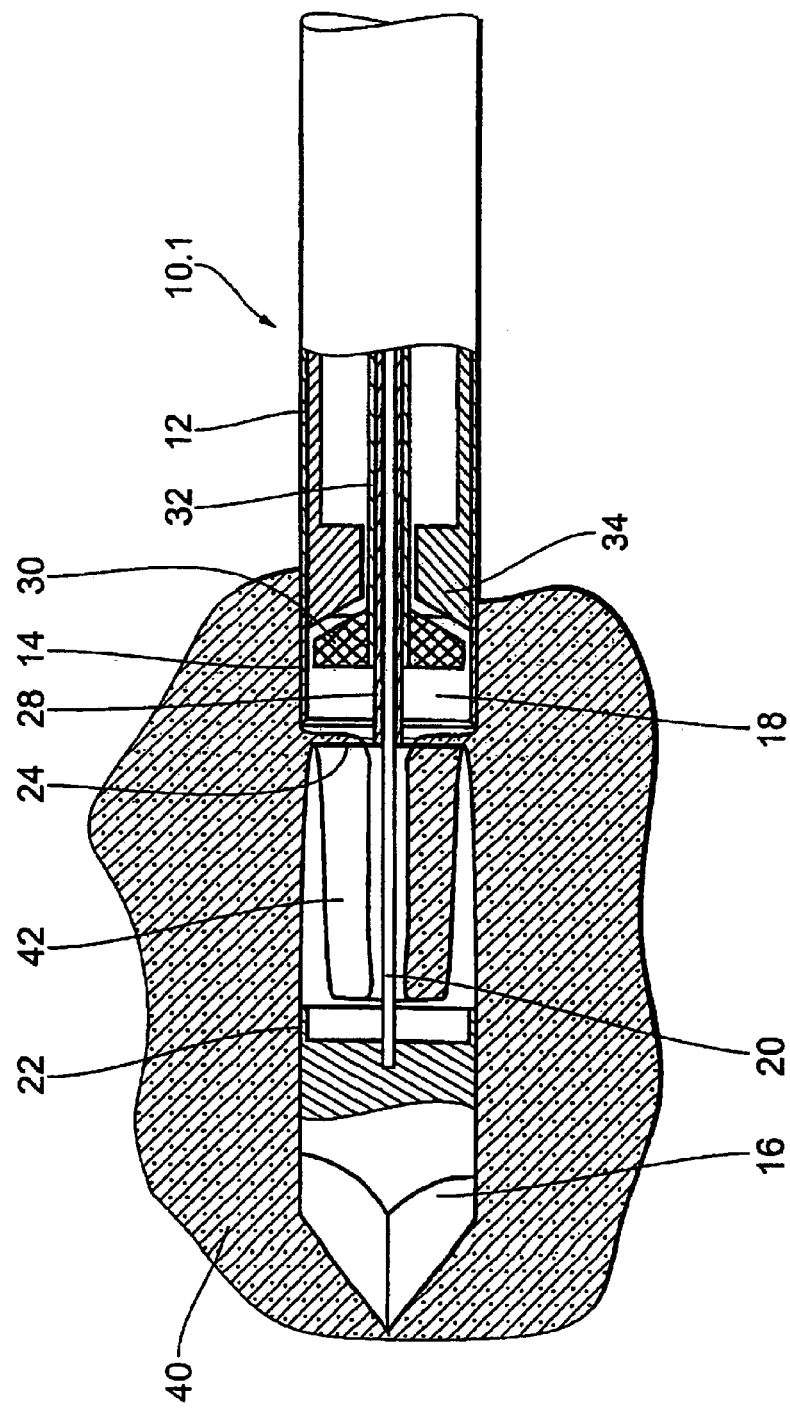

Then the cutting element 24 is retracted in the direction of the ejector 30 by means of the second thrust rod 28. In the meantime a high-frequency ac voltage is applied between the wire ring forming the cutting element 24 and the metal sleeve 12 serving as the counterpart electrode. The cutting electrode formed by the wire ring in that case produces many small spark discharges along the wire ring, due to the applied high-frequency voltage. As a result, produced between the tissue 40 and the cutting element 24 is a vapor cushion which permits contact-free electrical cutting. Cuts can be produced in the tissue with minimal thermal edge coagulation by virtue of the use of a rather sinusoidal high-frequency alternating current. Other degrees of coagulation at the cut location can be set by altering the so-called crest factor which describes the ratio of peak voltage to the effective voltage, and by additional high-frequency modulation. The operating procedure involved in cutting out the tissue is shown in FIGS. 1c and 1d, in which respect it can be seen in particular from FIG. 1d that the tissue portion 42 produced is in the form of a torus which surrounds the first thrust rod 20 and which, by virtue of the wire struts or the struts 26 (see FIG. 10) is slit in such a way that it admittedly completely embraces the thrust rod 20 but is divided in such a fashion that the tissue portion 42 can be later removed from the thrust rod 20.

Figure 1E:
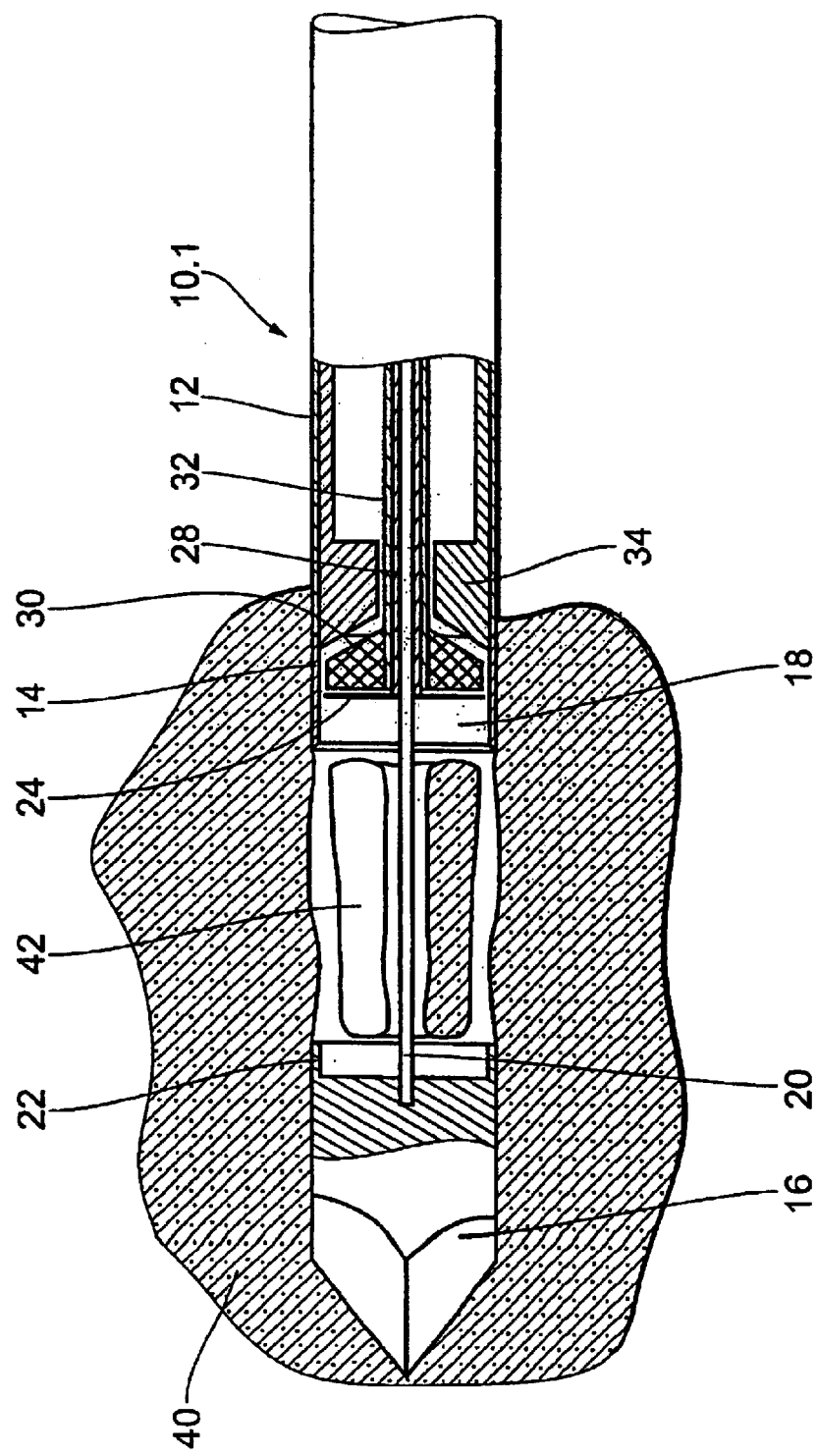
Figure 1F:
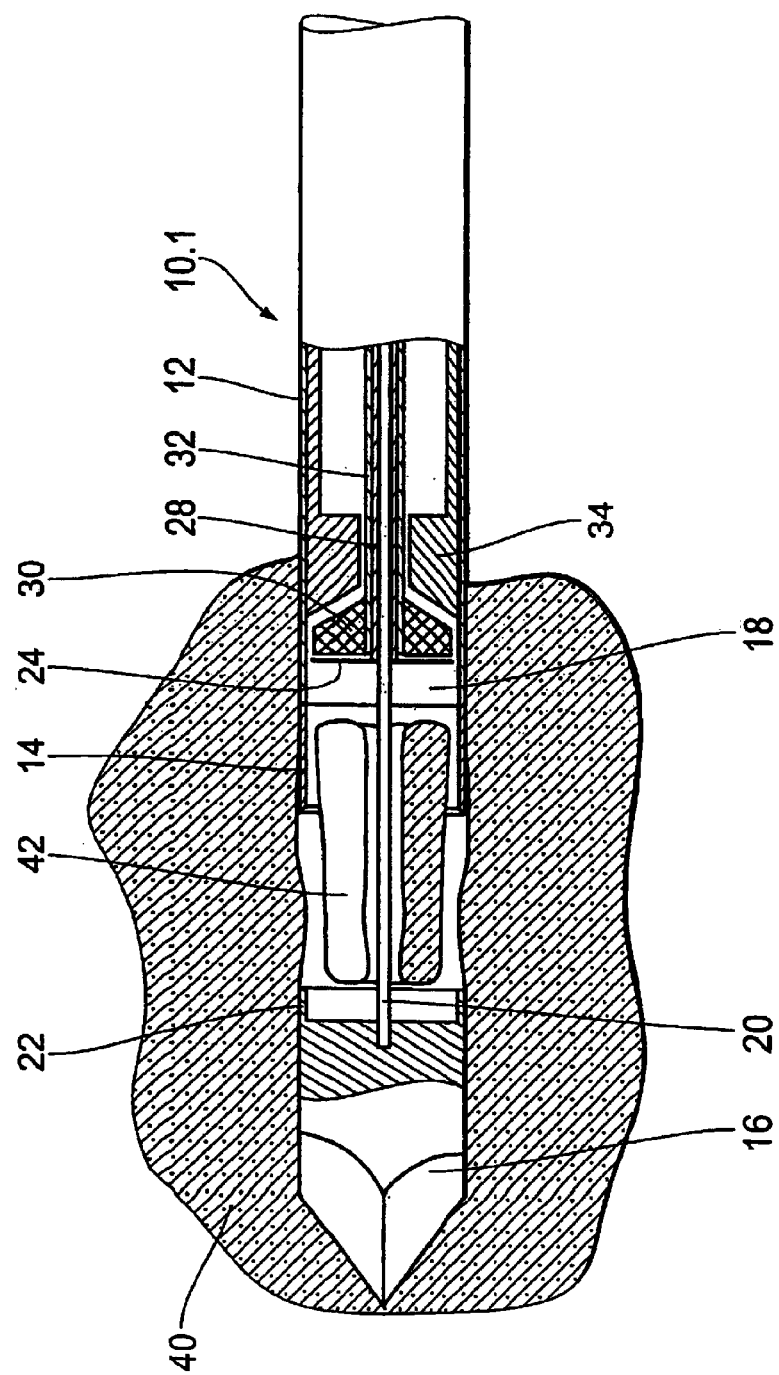
Figure 1G:
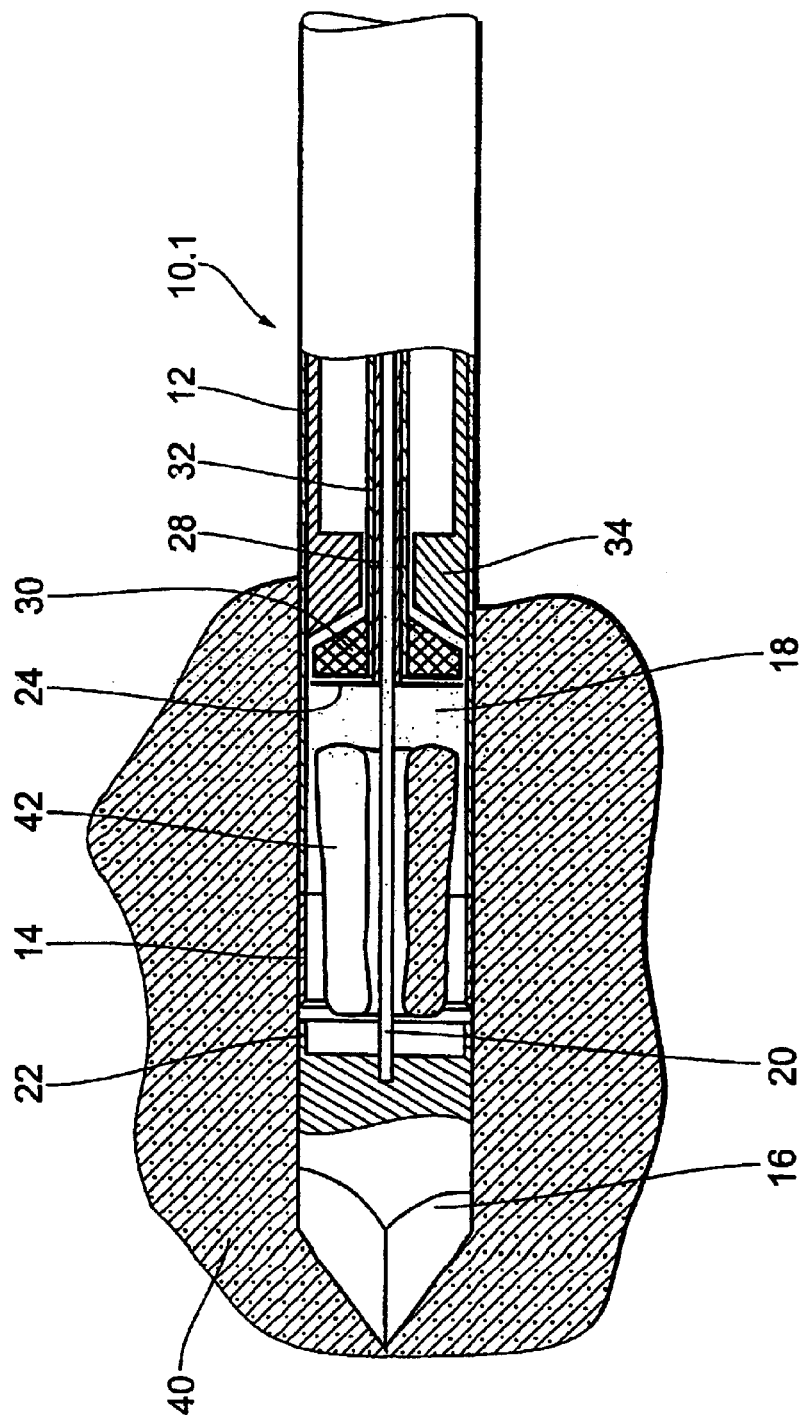
Figure 1H:
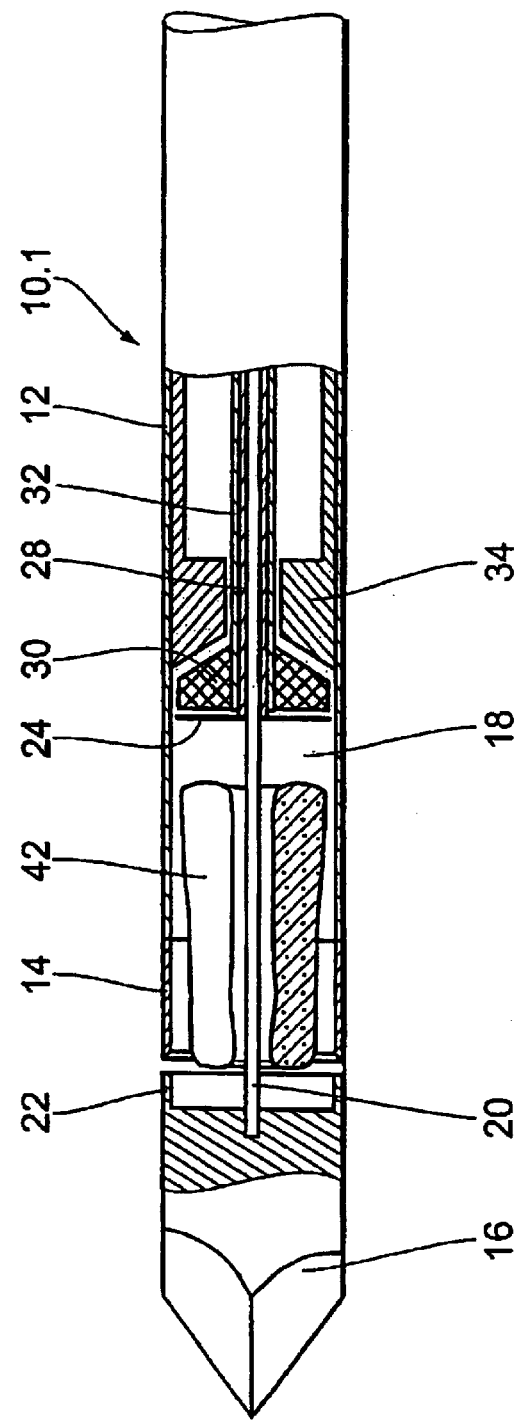
Figure 1I:
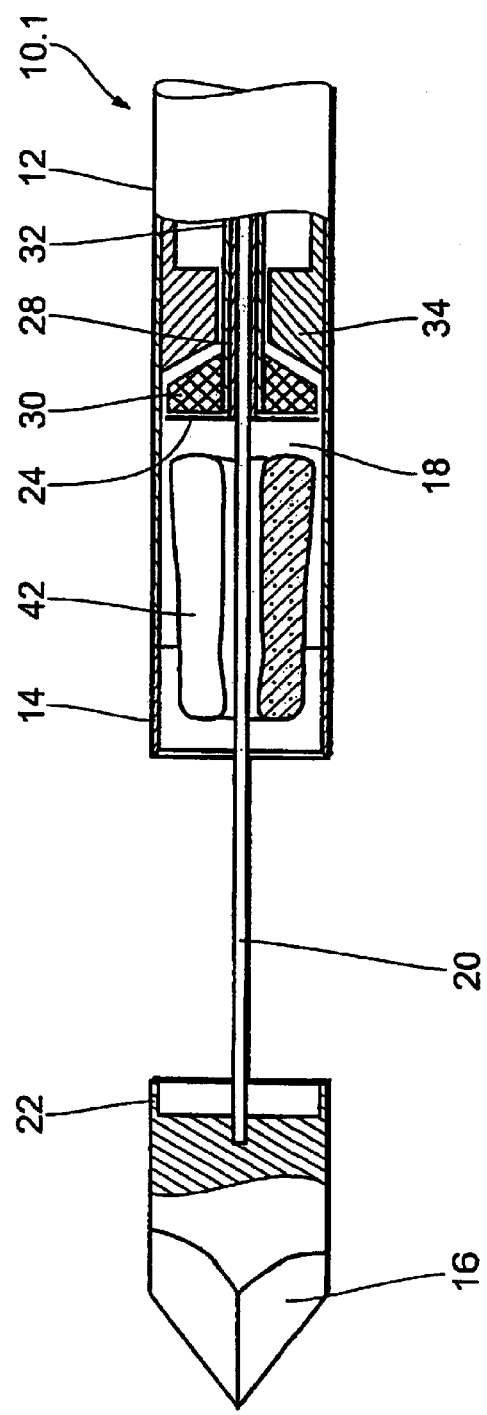
Figure 1J:
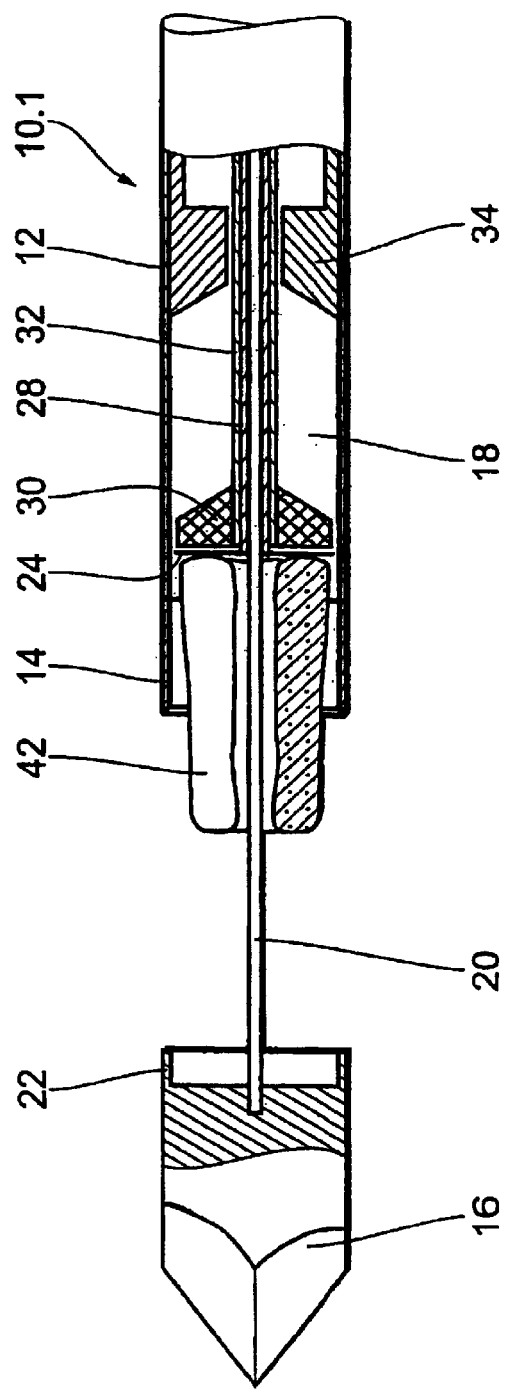
Figure 1K:
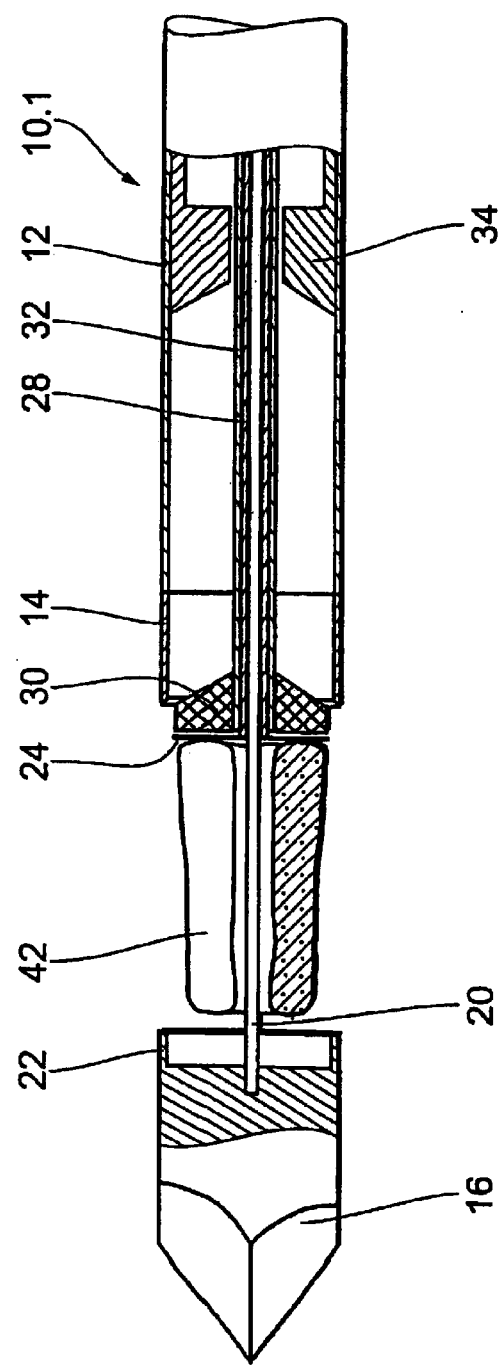
Figure 1I:
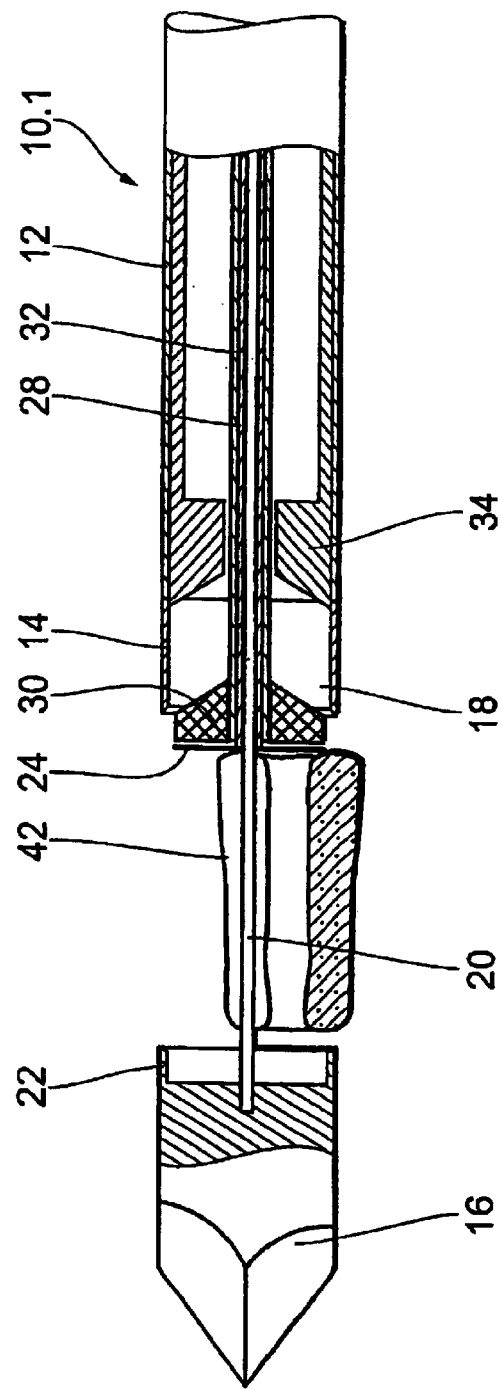

After the tissue portion 42 has been completely severed as shown in FIG. 1e the cutting element 24 is immediately in front of the ejector 30. After complete severing of the tissue portion 42 the metal sleeve 12 is displaced again in the direction of the metal tip 16, as shown in FIG. 1f. When the hollow probe 10.1 is then closed as shown in FIG. 1g, it is pulled out of the tissue 40; FIG. 1h shows the closed hollow probe 10.1 in the condition of having been pulled out of the tissue 40. The metal tip 16 is then pushed by means of the thrust rod 20 forwardly, in a distal direction with respect to the hollow probe 10.1. A cylindrical opening is again formed between the collar 22 and the distal end portion 14.

Then the ejector 30 together with the cutting element 24 is pushed forwardly in the direction of the metal tip 16. That causes ejection of the tissue portion 42 from the cavity 18, see FIGS. 1j and 1k.

As the tissue portion 42 is already slitted by virtue of the wire struts 26 of the cutting element 24, it easily falls away from the thrust rod 20, as is shown in FIG. 1l. After the tissue portion 42 has been ejected the hollow probe 10.1 can be put into its condition as shown in FIG. 1a again and is ready for fresh use.

Instead of cutting out a torus of tissue over the full length of the opening between the metal tip 16 and the metal sleeve 14, as described, by displacing the cutting element 24 appropriately over that length, it is also possible for only a part of the tissue which penetrates into the opening to be cut off. That is effected by a procedure whereby firstly a part of the tissue is cut as described above, so that the condition shown in FIG. 1c for example obtains. In that case the tissue which has already been partially severed is still connected to the other tissue, on the side towards the metal sleeve 12. When the cutting element 24 is rotated in the position shown in FIG. 1c together with thrust rod 28 about the longitudinal axis of the latter, the arm or arms or strut or struts 26 (see FIG. 10) completely sever the tissue which hitherto has been partially cut away, from the rest of the tissue. Then a small portion of tissue can also be removed by closing the opening between the metal tip 16 and the metal sleeve 12. That can also be achieved if the opening between the metal tip 16 and the metal sleeve 12 is not opened quite as far as shown in FIGS. 1b through 1e, but only in part, so that overall less tissue also penetrates into the then smaller opening between the metal tip 16 and the metal sleeve 12.

Figure 2A:
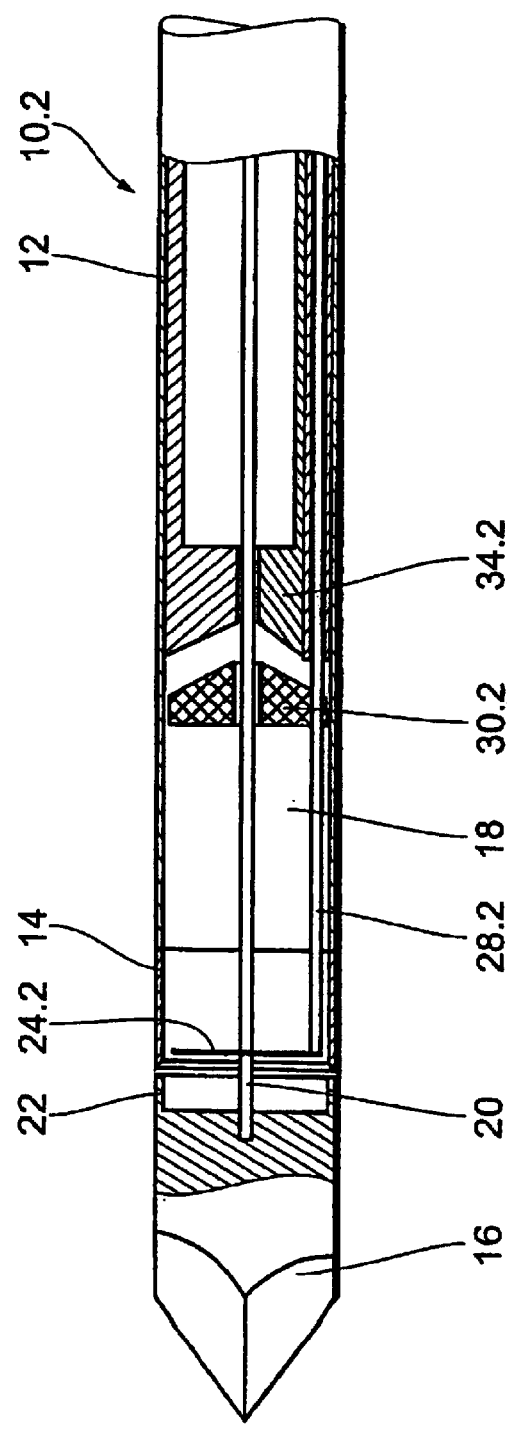
FIGS. 2 through 9 show alternative embodiments of a hollow probe in various operating conditions.
Figure 2B:
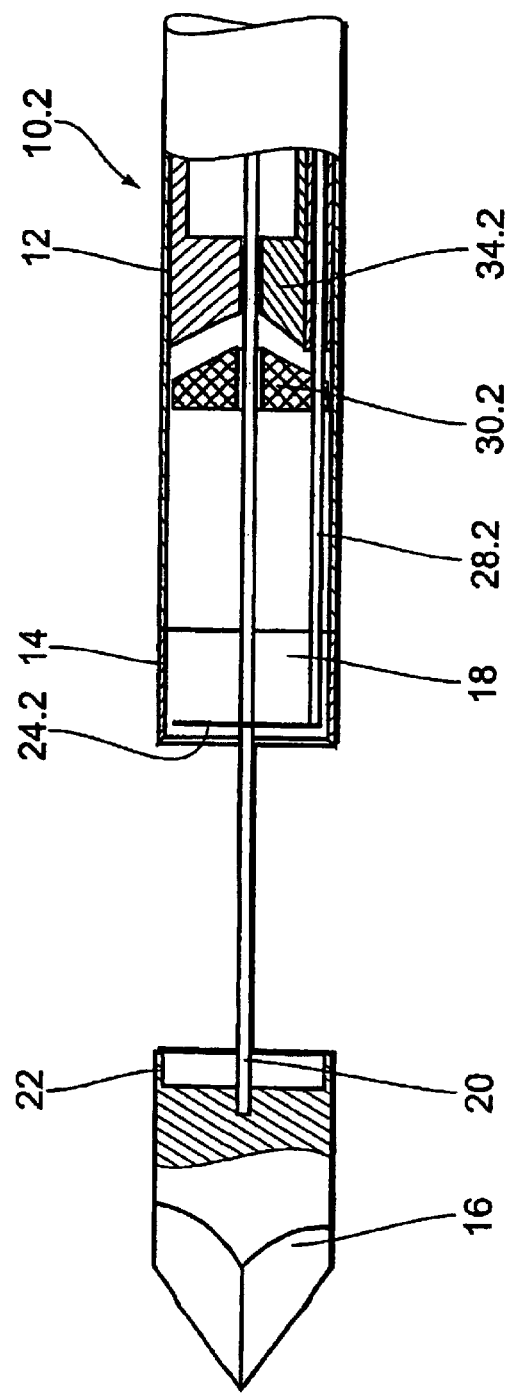
Figure 2C:
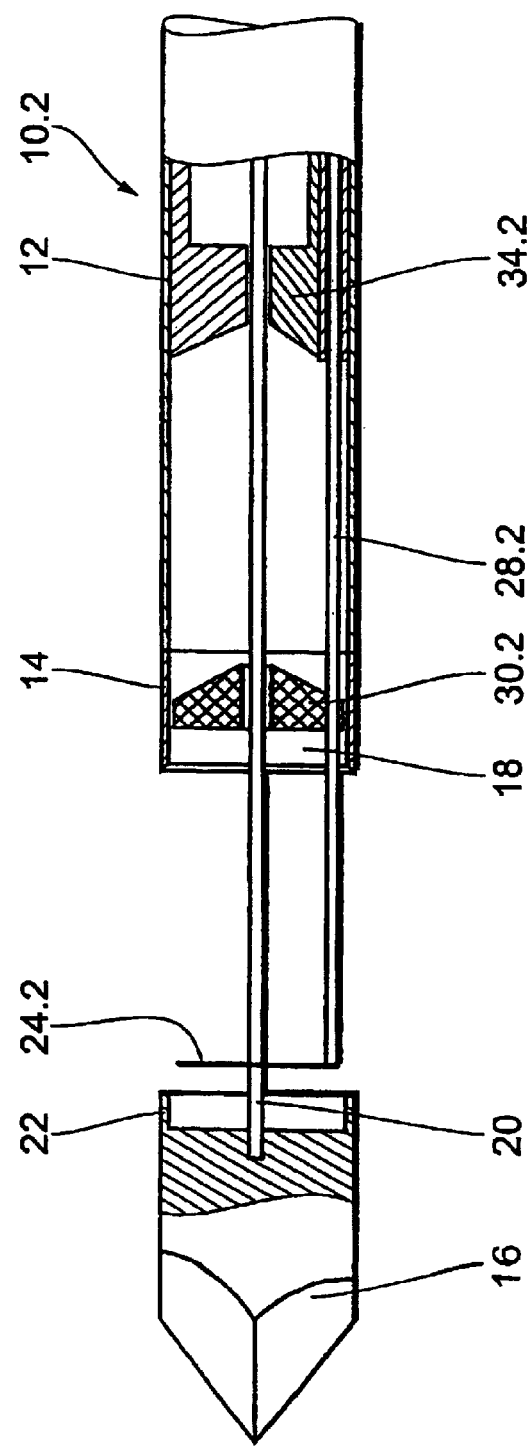
Figure 2D:
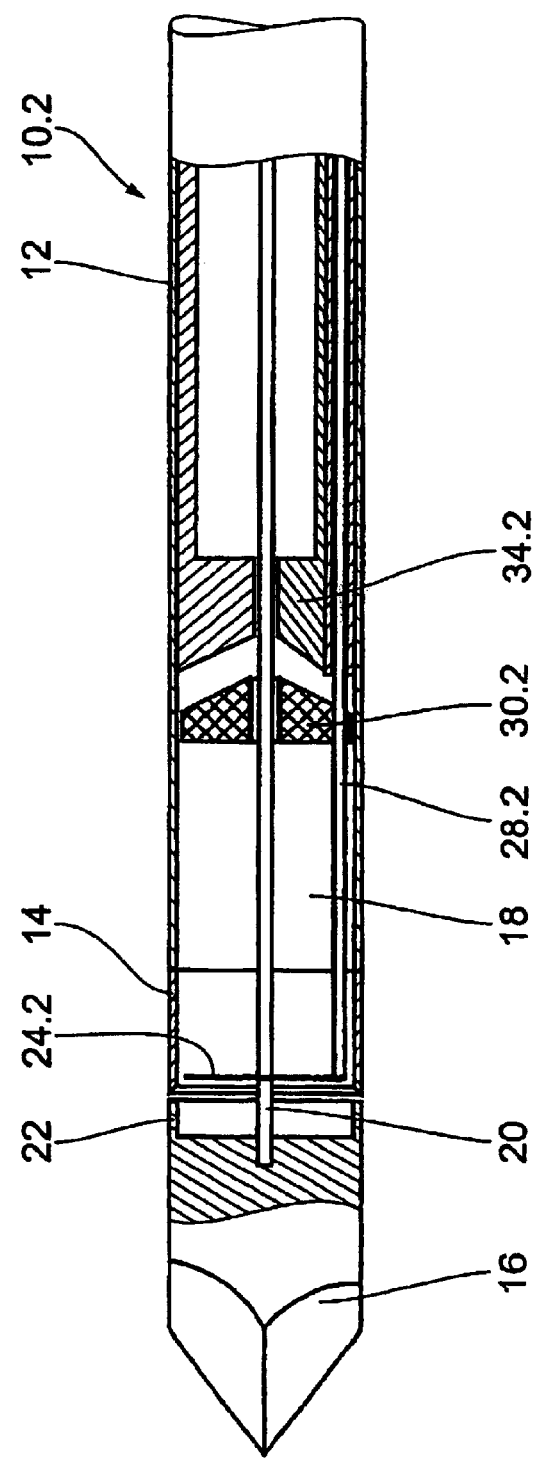
Figure 2E:
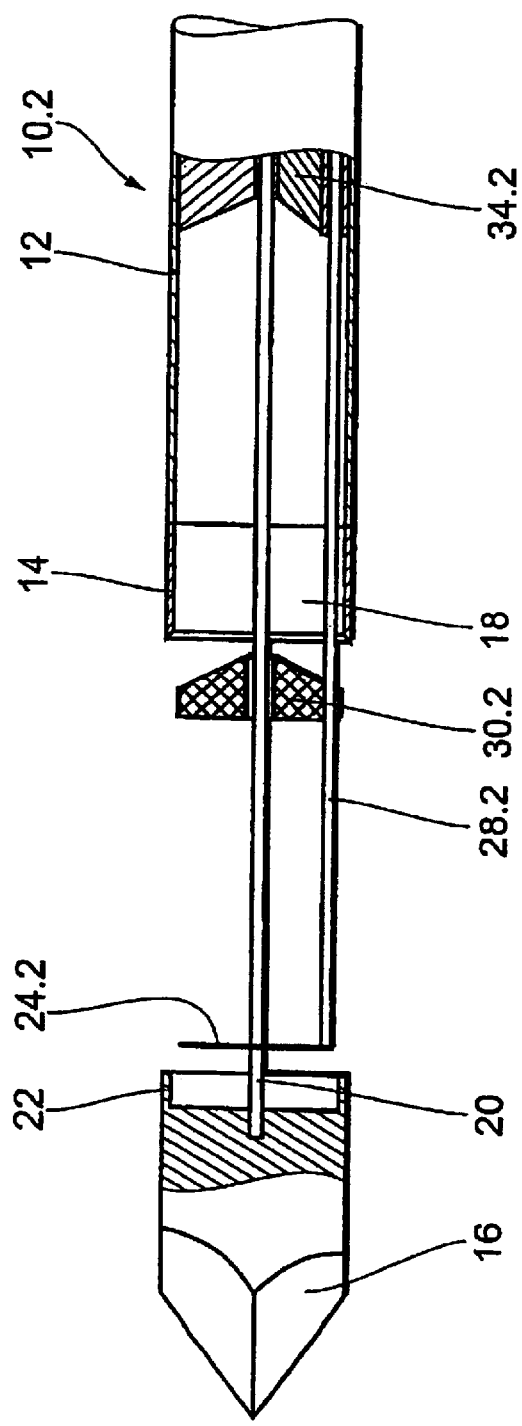
Figure 3A:
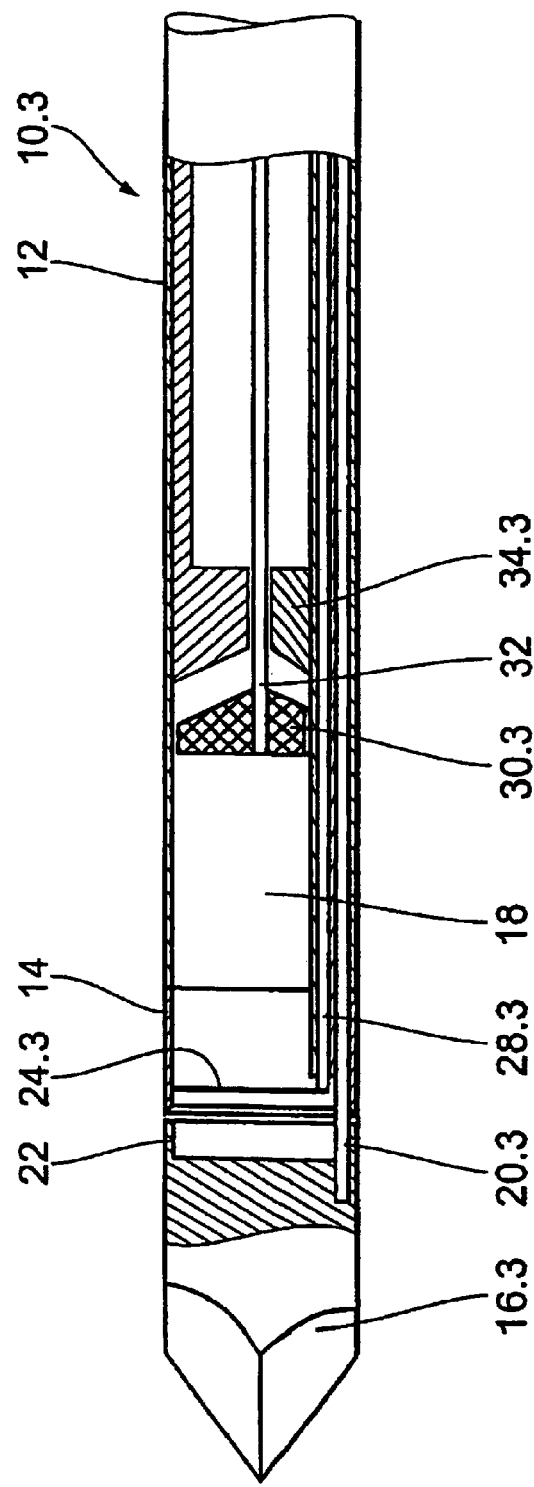
Figure 3B:
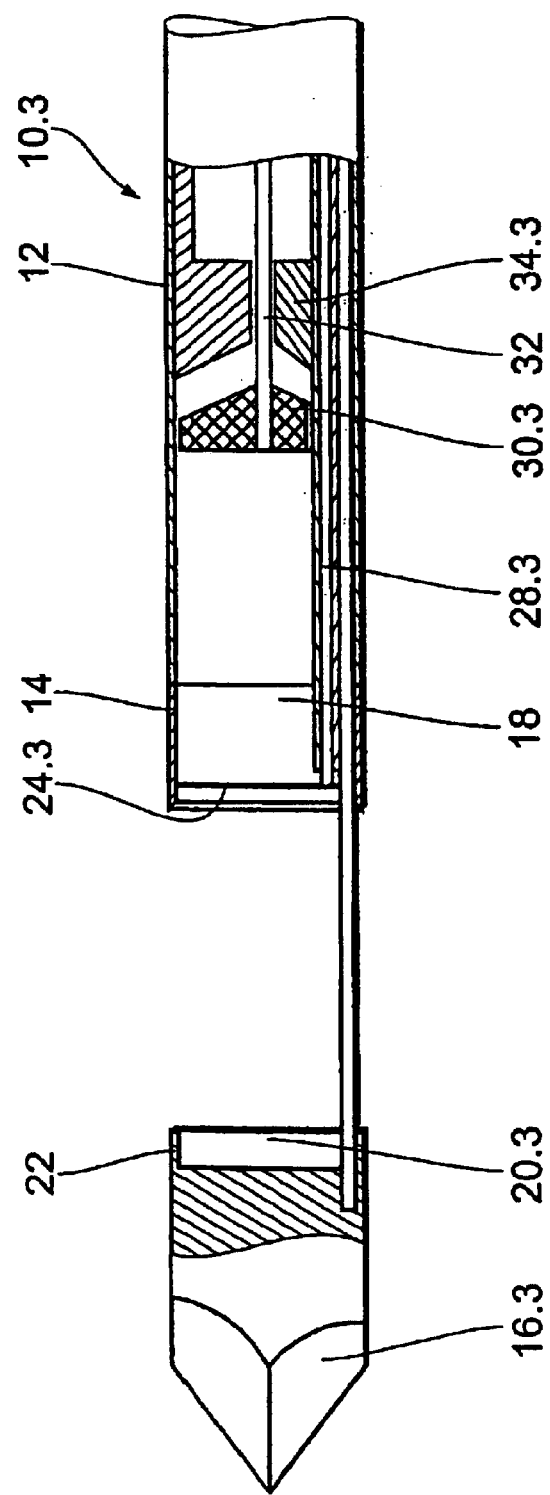
Figure 3C:
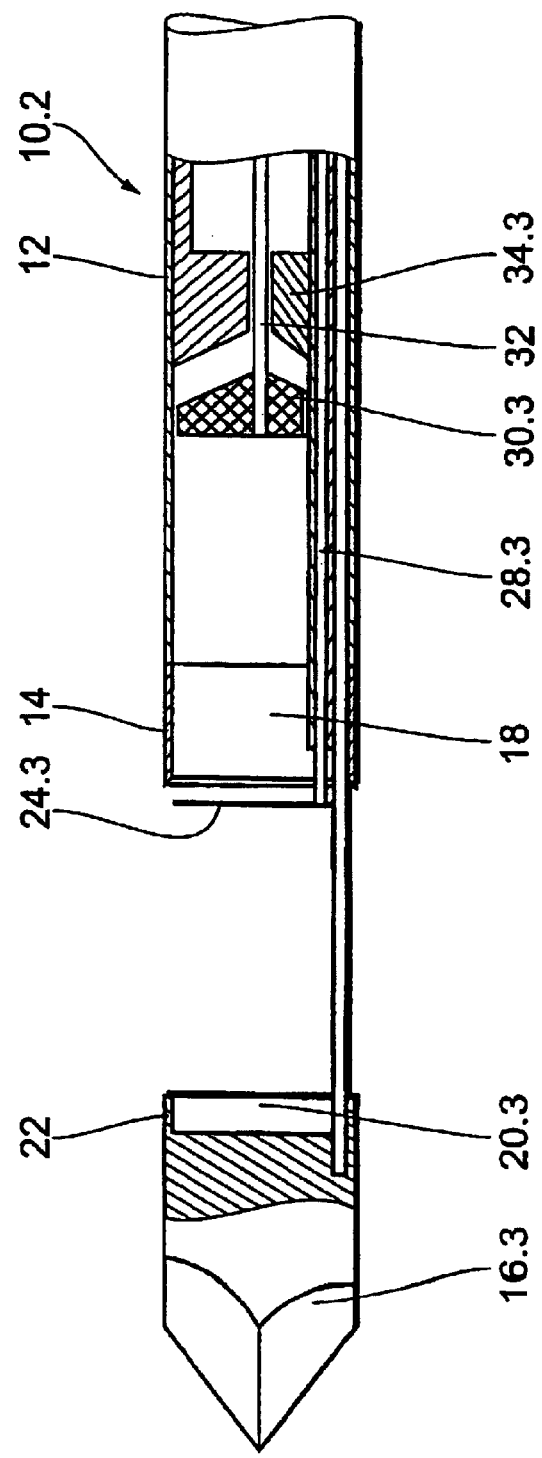
Figure 3D:
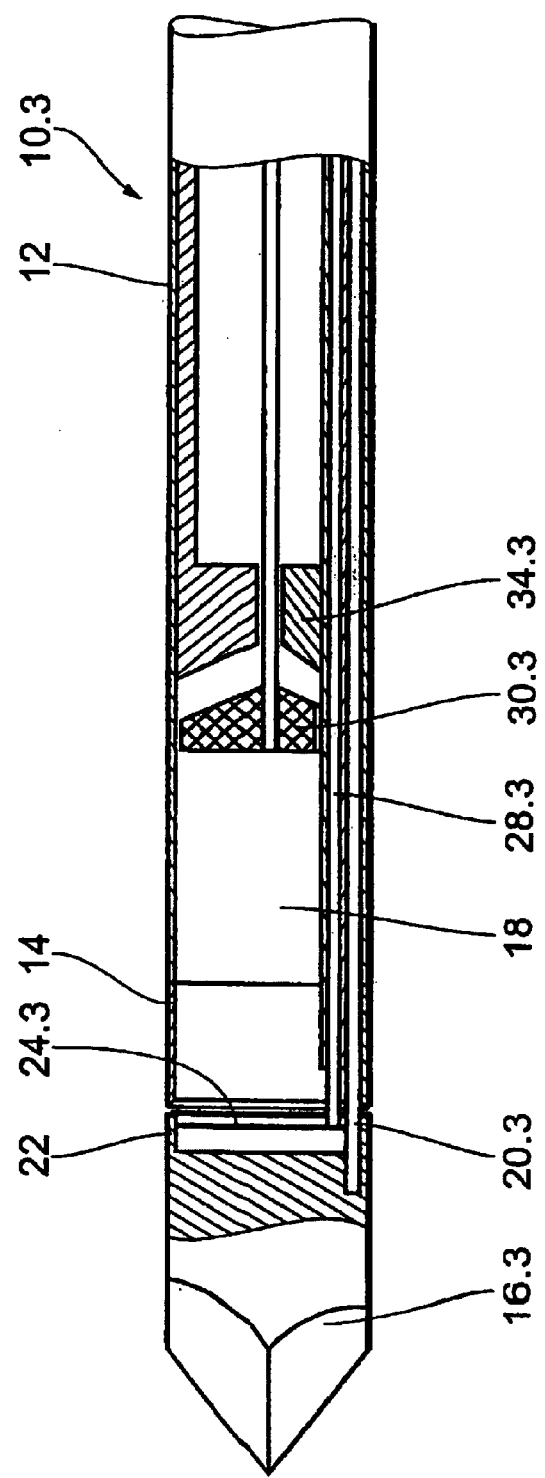
Figure 3E:
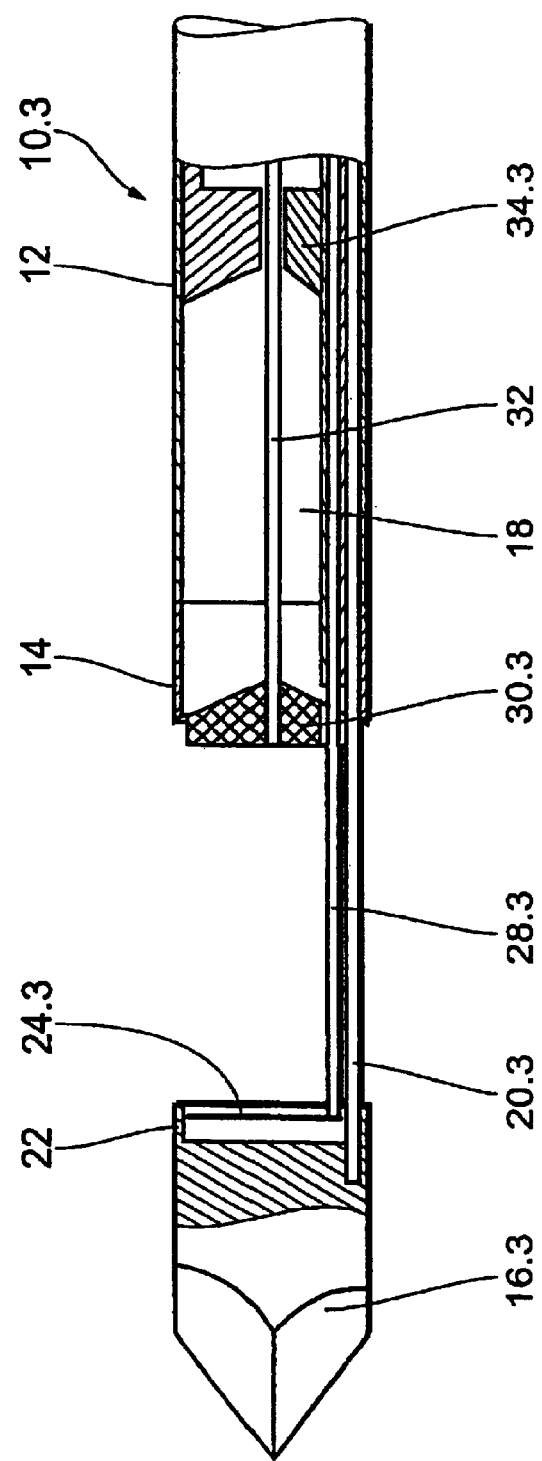

The hollow probe 10.2 shown in FIGS. 2a through 2e differs from the hollow probe 10.1 shown in FIGS. 1a through 1l in some structural details. Hereinafter only the differences in the hollow probe 10.2 in relation to the hollow probe 10.1 shown in FIG. 1 will be discussed. The thrust rod 28.2 for the cutting element 24.2 is not arranged centrally but at the side of the receiving space 18. In addition the unit does not have a separate thrust rod for the ejector 30.2. Rather the ejector 30.2, like the cutting element 24.2, is fixed to the thrust rod 28.2. The cutting element 24.2 and the ejector 30.2 are therefore equally moved by the thrust rod 28.2 and maintain their fixed spacing from each other. As can be seen from FIG. 2b, to open the opening between the metal tip 16 and the metal sleeve 12, the metal sleeve 12 together with thrust rod 28.2 is withdrawn in the cutting element 24.2 so that, immediately after opening of the opening, the cutting element 24.2 is still within the distal end portion 14 of the metal sleeve 12. Then, for cutting out tissue, the thrust rod 28.2 is pushed forwardly in the direction of the metal tip 16, together with the cutting element 24.2 and the ejector 30.2. This is shown in FIG. 2c. As soon as the cutting element 24.2 has reached its end position in the proximity of the metal tip 16 and a suitable tissue portion has been severed, the metal sleeve 12 is pushed relative to the metal tip 16 and the thrust rod 20 thereof and relative to the cutting element 24.2, its thrust rod 28.2 and the ejector 30.2 fixed thereto, in the direction of the metal tip 16 in order to close the opening. The closed condition of the hollow probe 10.2 is shown in FIG. 2d.

The closed hollow probe 10.2 is then pulled out of the tissue together with the severed tissue. After the hollow probe 10.2 has been pulled out of the tissue, the hollow probe is opened again for ejection of the severed tissue. For that purpose the metal sleeve 12 is retracted relative to the metal tip 16 and the cutting element 24.2 as well as the ejector 30.2, that is to say the metal tip 16, the cutting element 24.2 and the ejector 30.2 maintain their relative positions with respect to each other. By virtue of the ejector 30.2 the tissue is not retracted together with the metal sleeve 12 but is ejected from the receiving space 18.

The hollow probe 10.3 shown in FIGS. 3a through 3e has thrust rods 20.3 and 28.3 respectively which are arranged laterally of the receiving space, both for the metal tip 16.3 and also for the cutting element 24.3. As in FIG. 1 the ejector 30.3 has a central thrust rod 32. The metal tip 16.3, the cutting element 20.3 and the ejector 30.3 can be moved separately by means of the thrust rods 20.3, 28.3 and 32, as in the case of the hollow probe 10.1 shown in FIG. 1. The operating movements shown in FIGS. 3b through 3e differ from those in FIG. 1 in that the metal sleeve 12 together with the cutting element 24.3 and the ejector 30 is retracted to open the opening between the metal sleeve 12 and the metal tip 16 after the hollow probe 10.3 has been inserted into tissue. Then, to cut out a portion of tissue, the cutting element 24.3, as in the variant shown in FIG. 2, is pushed out of the metal sleeve 12 forwardly in the direction of the metal tip 16. Then the hollow probe 10.3 is closed and all of the severed portion of tissue is removed from the tissue. Ejection of the severed portion of material is effected after opening of the hollow probe 10.3 by means of the ejector 30.3 in the same manner as shown in FIG. 1; see FIG. 3e.

Figure 4A:
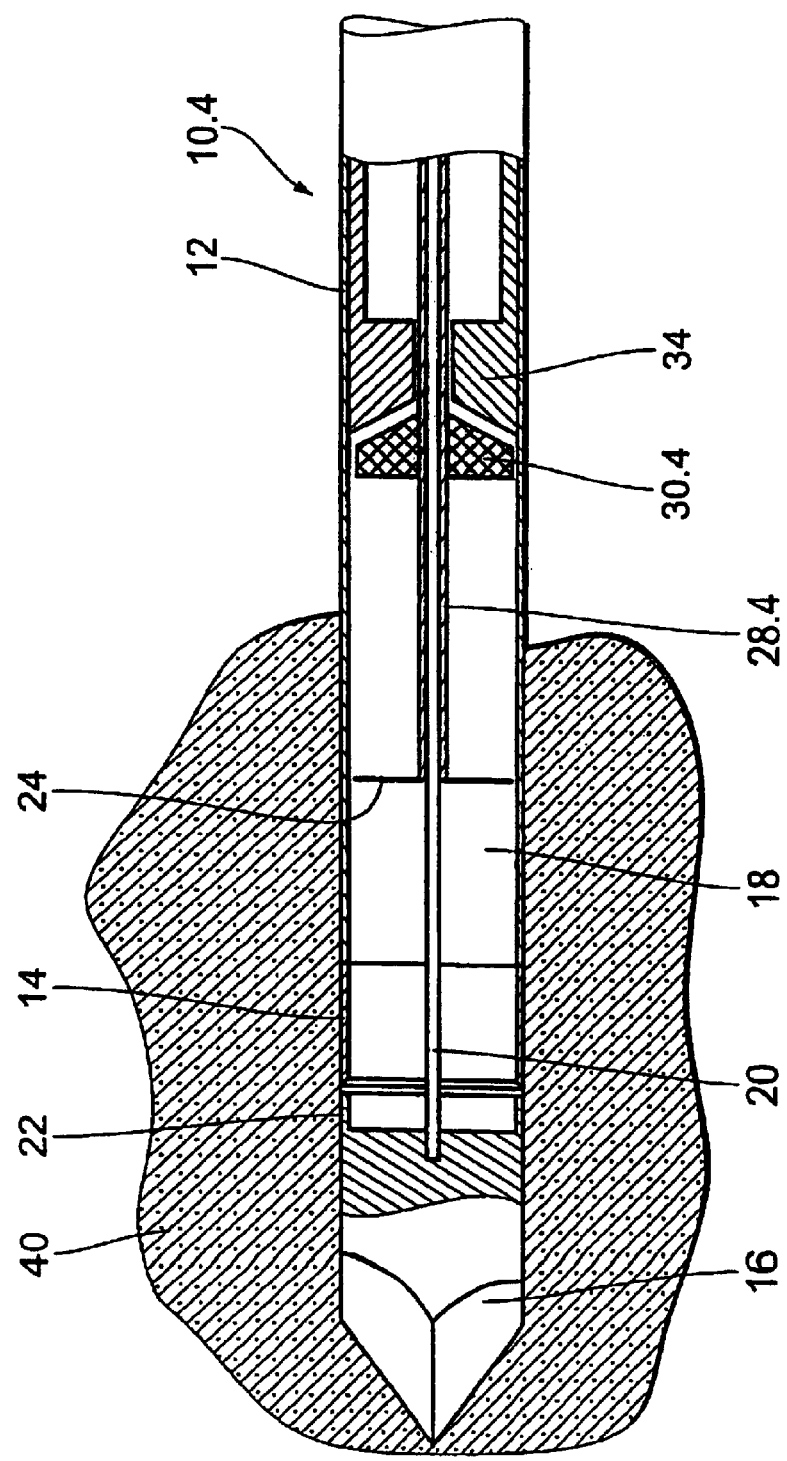
Figure 4B:
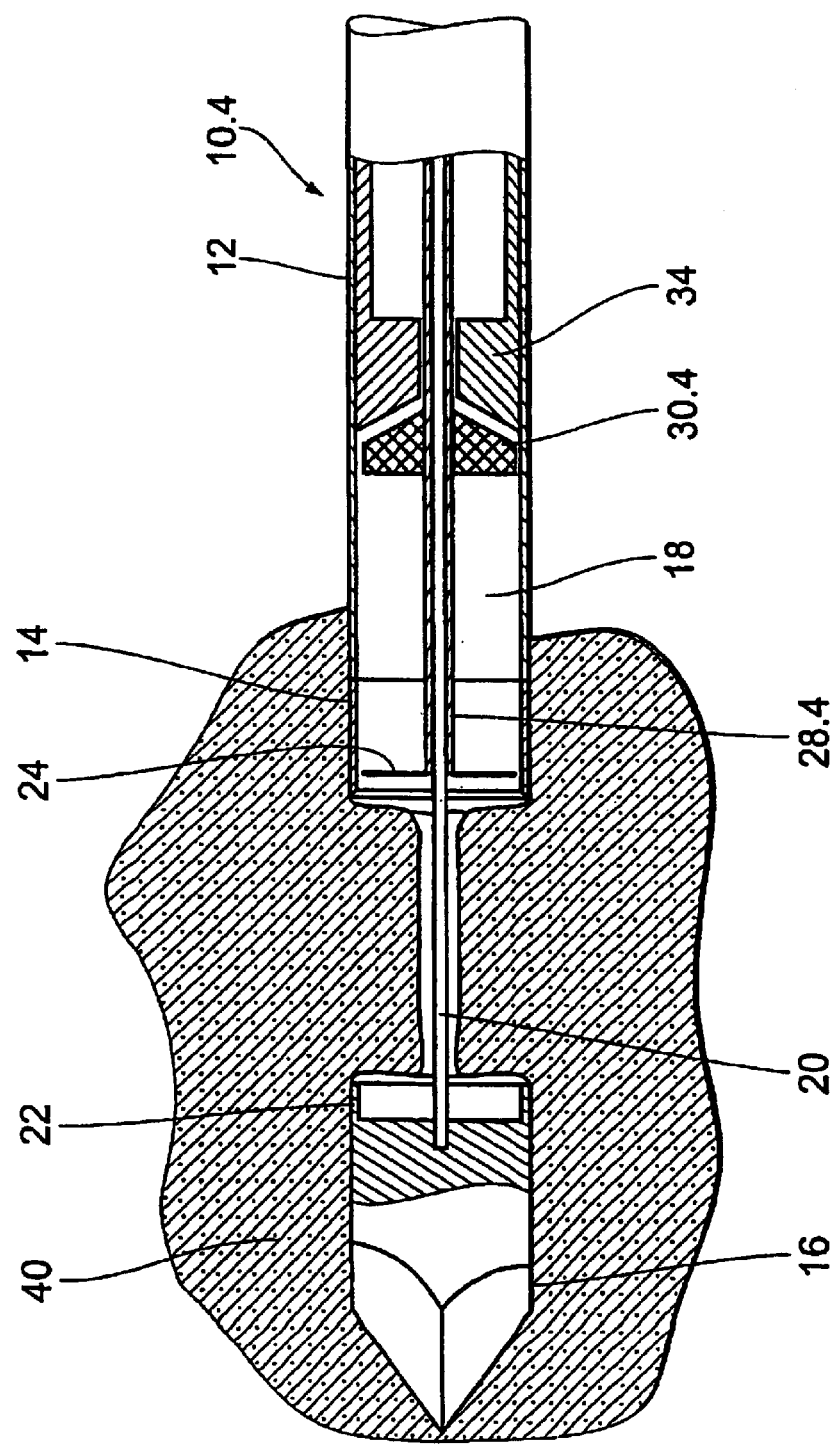
Figure 4C:
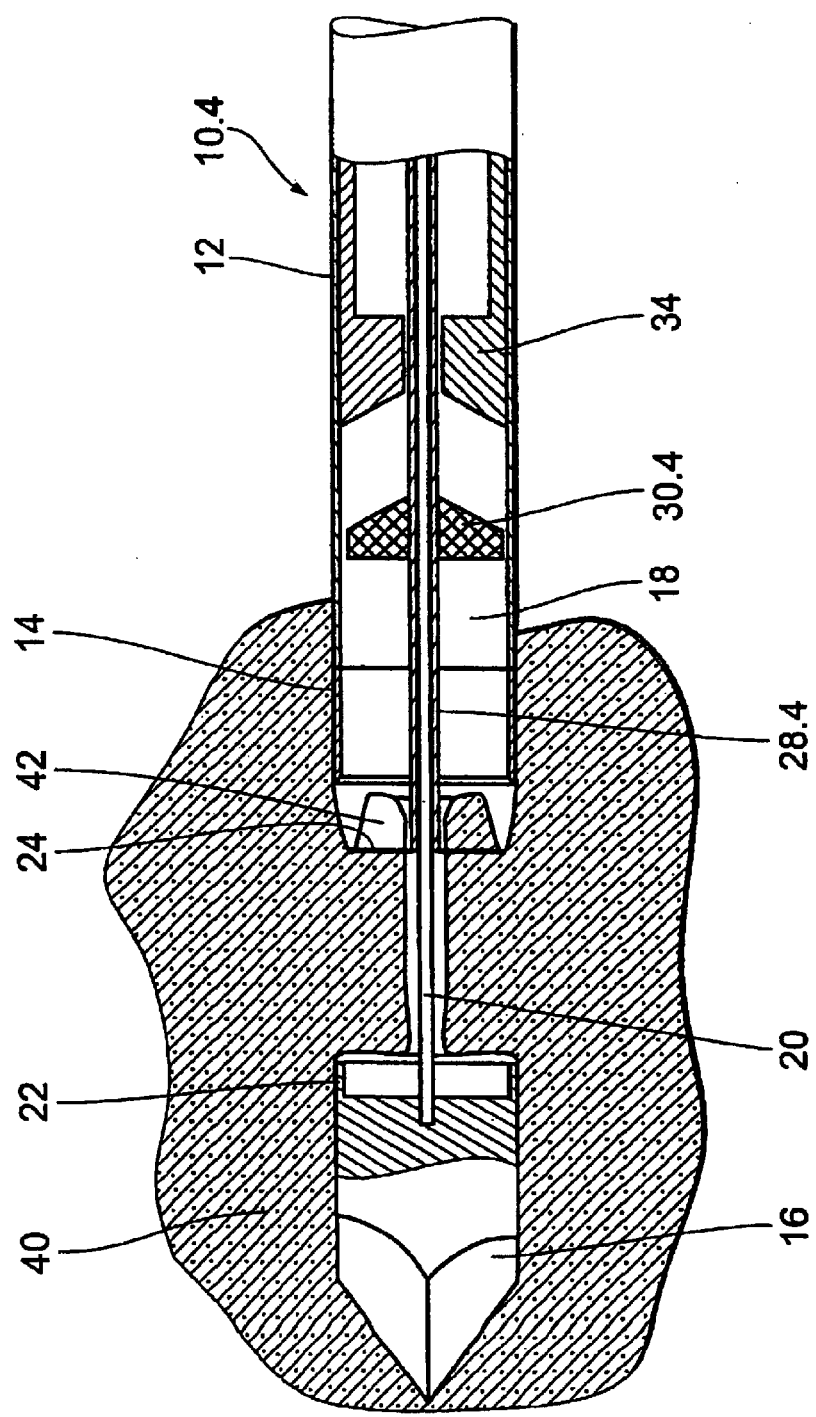
Figure 4D:
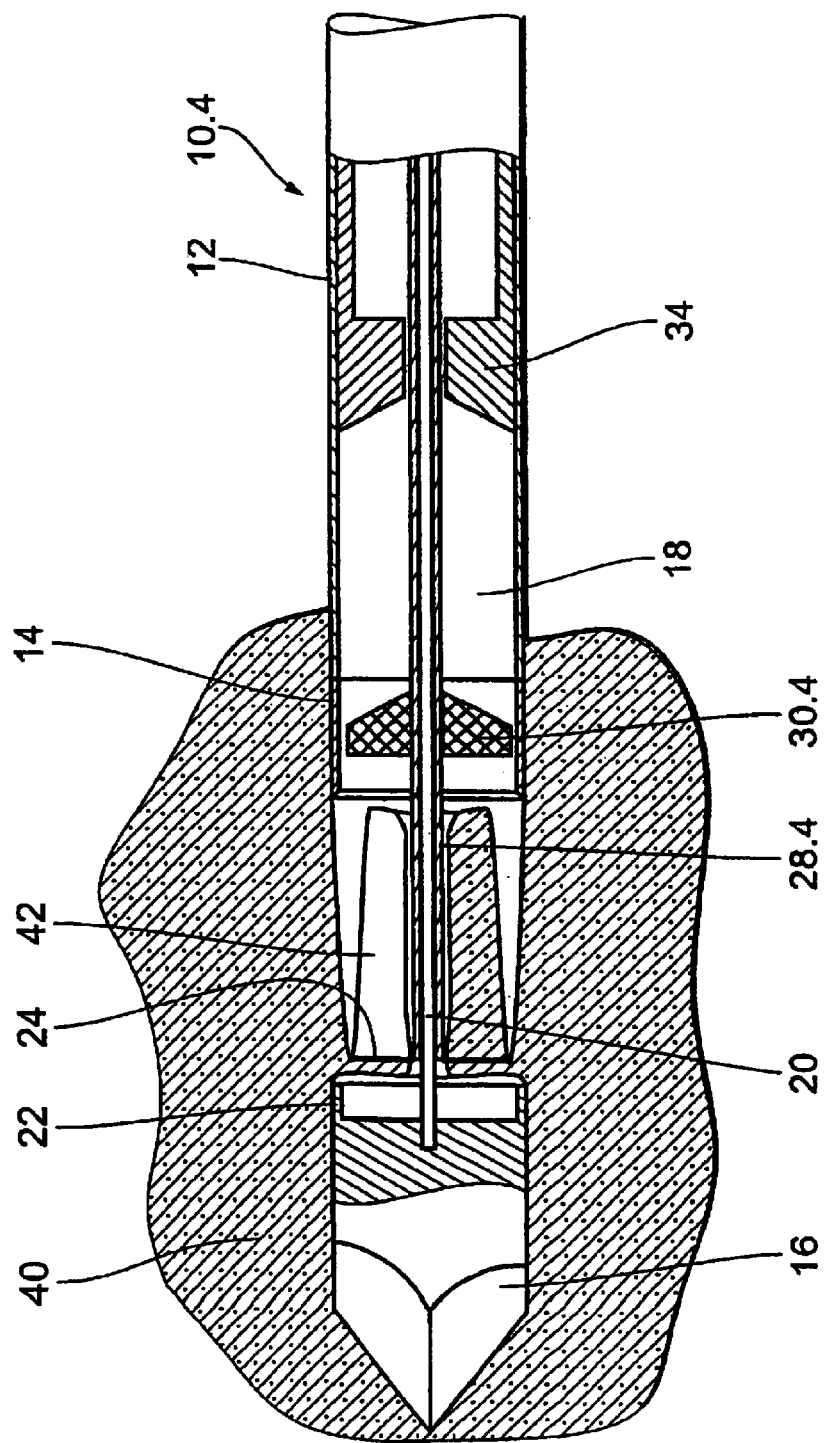
Figure 4E:
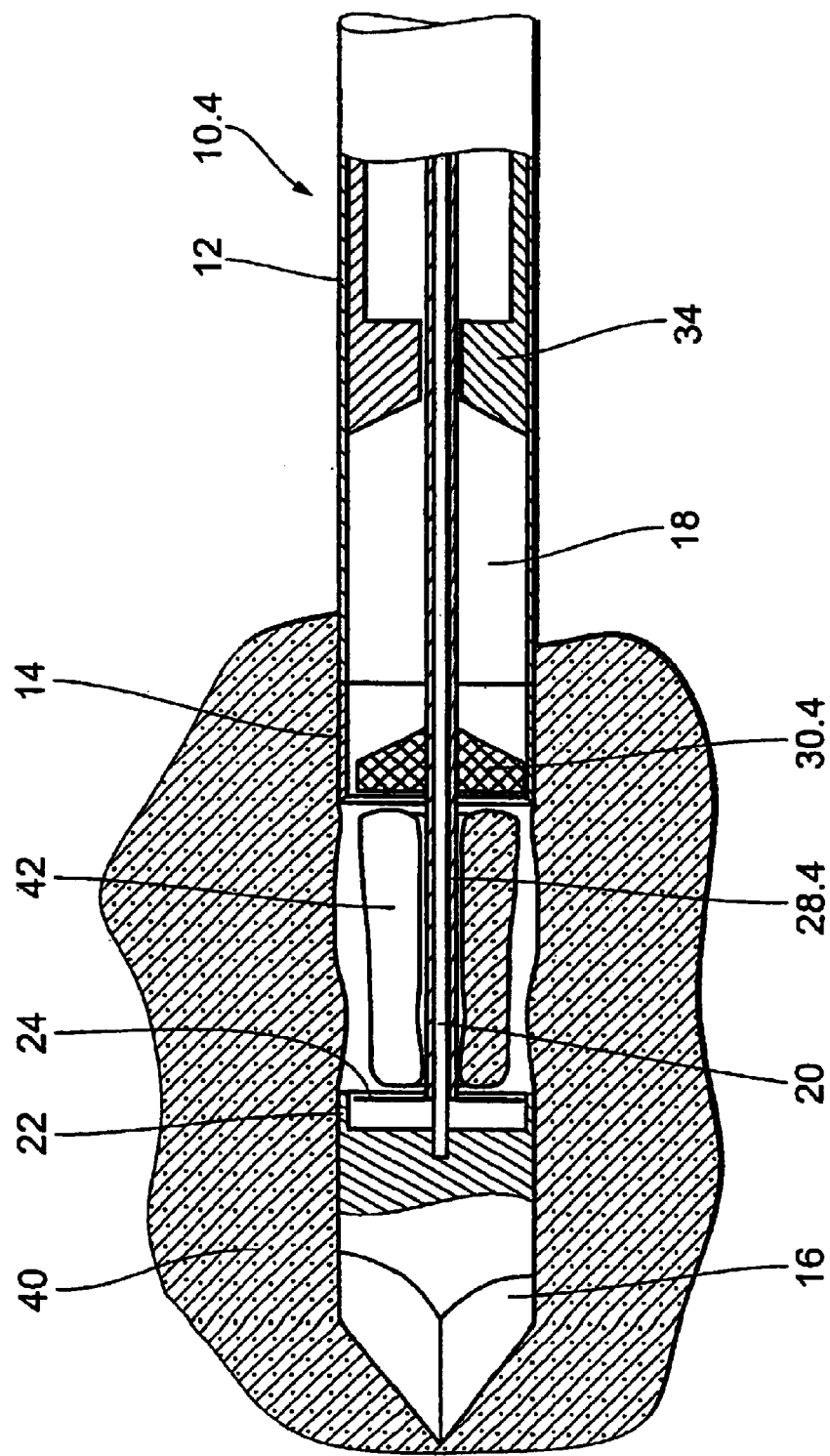
Figure 4F:
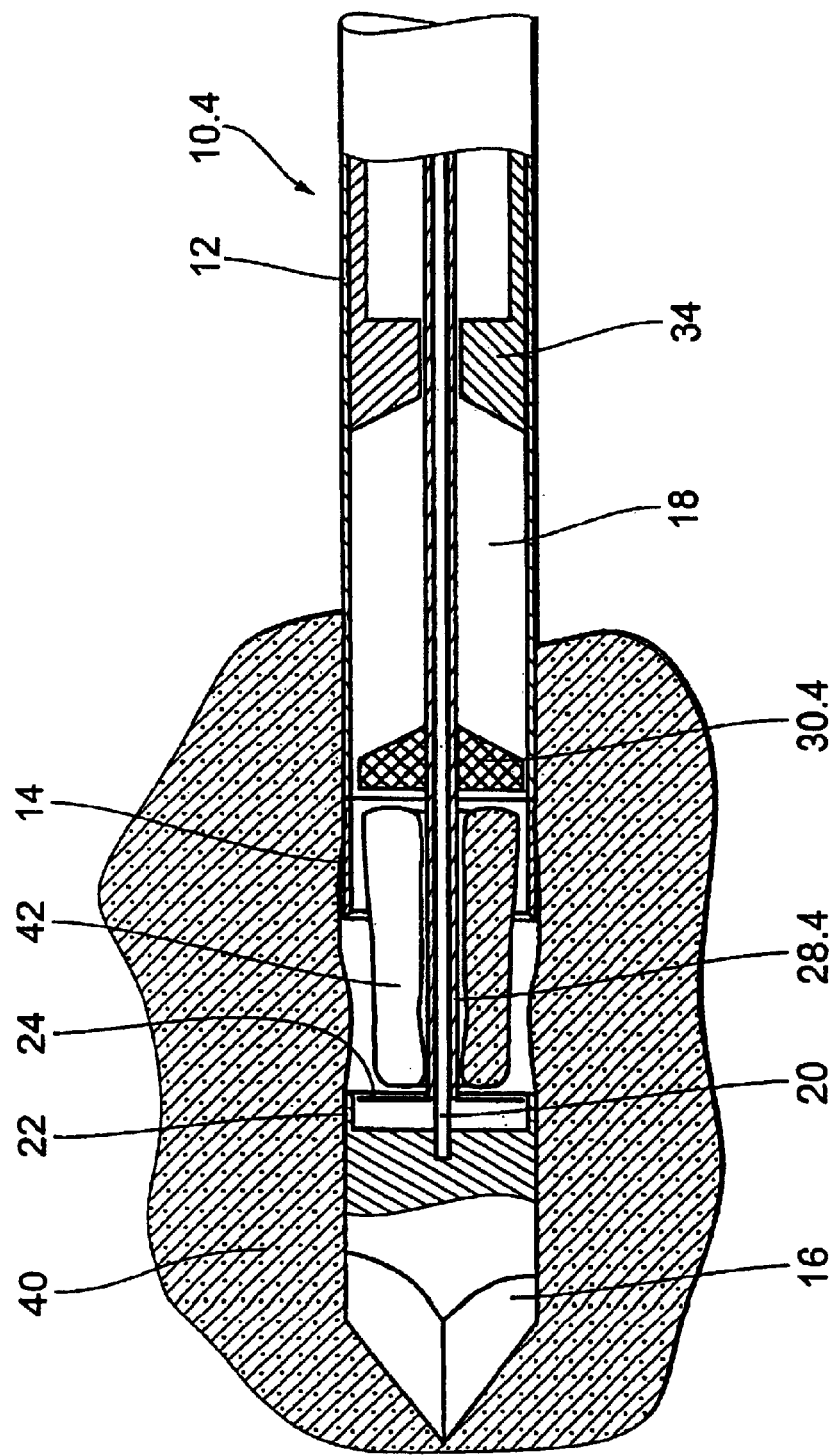
Figure 4G:
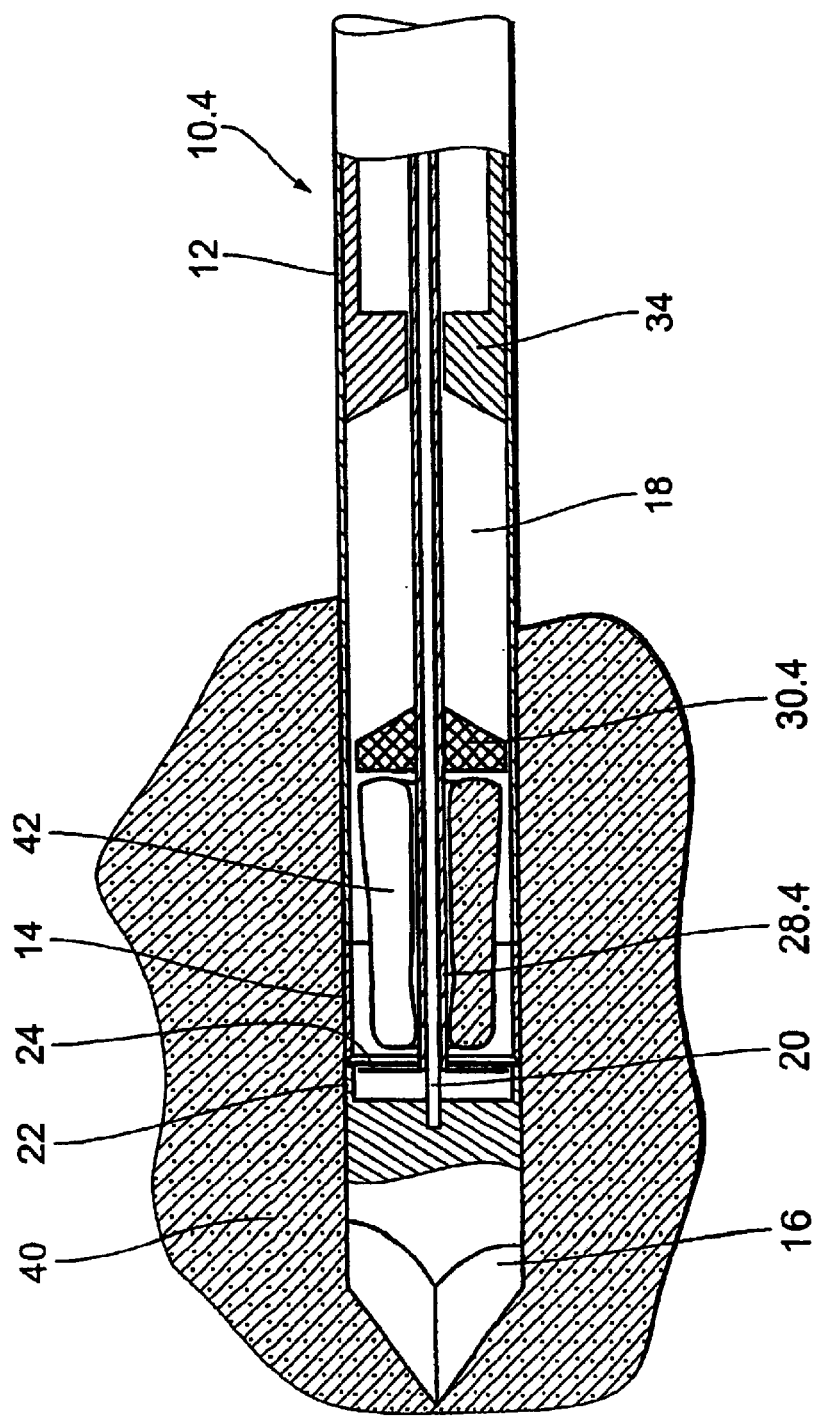
Figure 4H:
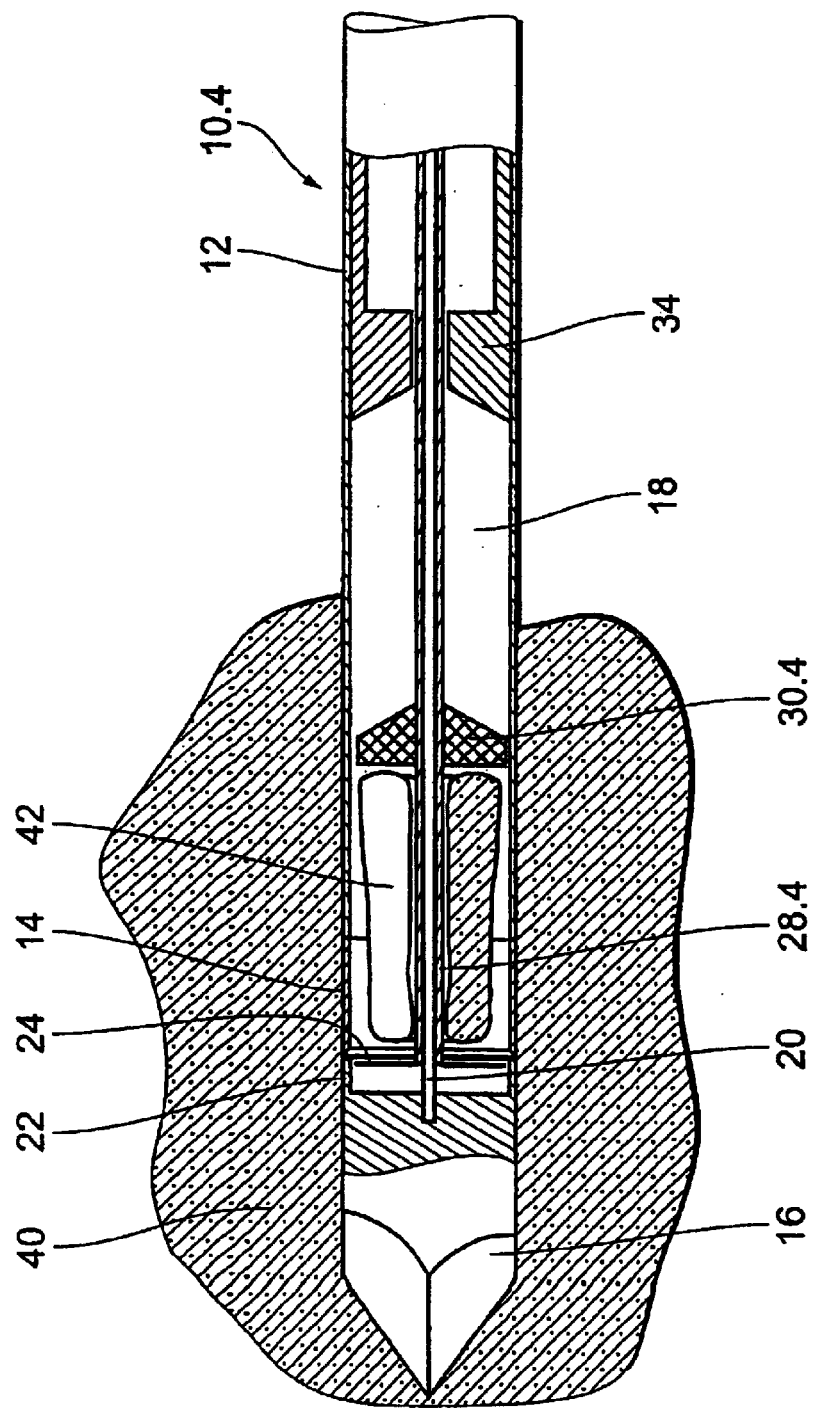
Figure 4I:
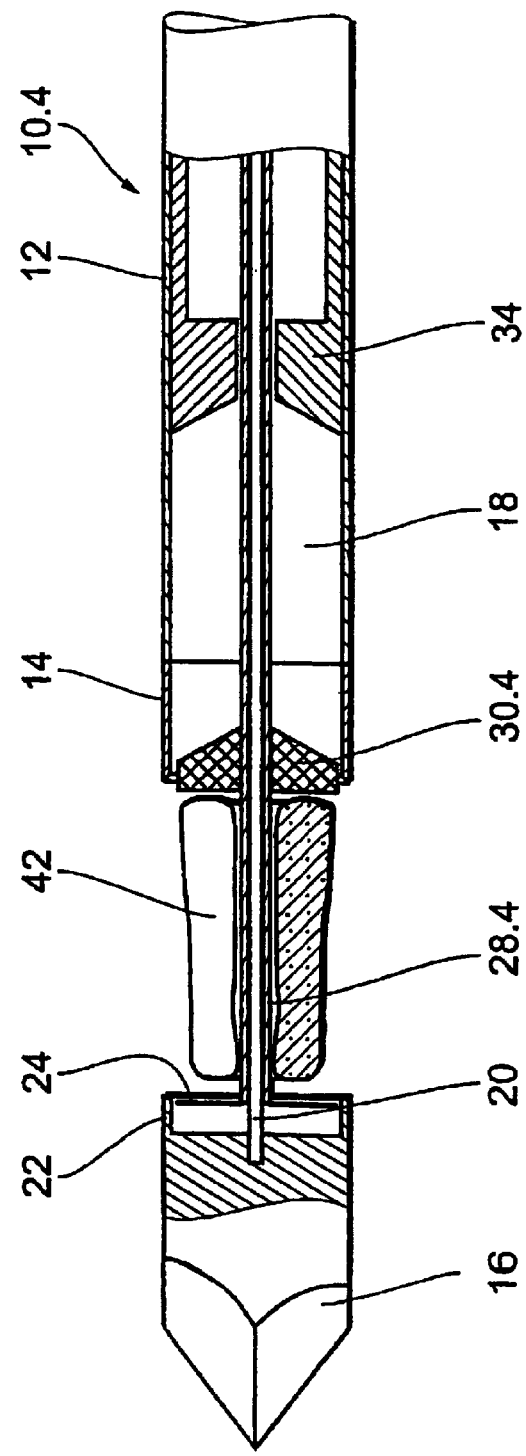
Figure 4J:
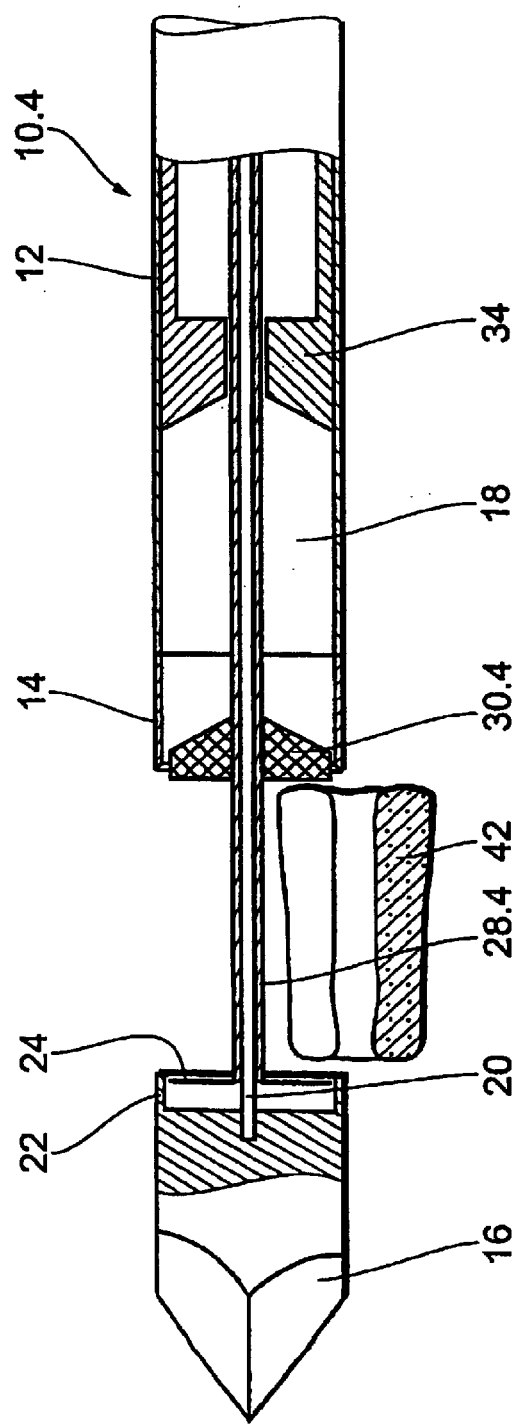

The variant of a hollow probe 10.4 shown in FIGS. 4a through 4j, as a departure from the hollow probe shown in FIG. 1, has a central thrust rod 28.4 at the distal end of which the cutting element 24 is fixed and to which an ejector 30.4 is also fixed. As in the variant shown in FIG. 2 therefore the cutting element 24 and the ejector 30.4 are moved by a common thrust rod 28.4. In that case movement of the cutting element 24 is effected after opening of the hollow probe 10.4, as in the embodiment shown in FIG. 3, out of the metal sleeve 12 towards the metal tip 16. As shown in FIGS. 4c through 4e the ejector 30.4 is pushed simultaneously with the cutting element 24 in a direction towards the metal tip 16.

When the cutting element 24 is rotated in its position shown in FIG. 4c or FIG. 4d about the longitudinal axis of its thrust rod 28.4 the struts 26 connecting the ring-shaped cutting element 24 to the thrust rod 28.4 completely cut the tissue portion 42 which has already been partially severed, completely away from the rest of the tissue 40.

After complete severing of a portion 42 of tissue—as shown in FIG. 4e—the hollow probe 10.4 is closed again. For that purpose either the metal sleeve 12 is pushed forwardly in the direction of the metal tip 16, but it is also possible for the metal tip 16 together with the cutting element 24 and the ejector 30 to be retracted into the receiving space 18. In a preferred embodiment the ejector 30 is in sealing relationship with the wall of the metal sleeve 12. That assists with sucking a severed portion 42 of tissue into the receiving space 18 while the hollow probe 10.4 is closed.

Besides a kind of vacuum which is produced by the movement of the ejector 30 in the receiving space 18 vacuum can also additionally be applied to the receiving space 18 by way of external means. It is preferred in that case if the ejector 30 is not in sealing relationship with the wall of the metal sleeve 12. The application of a vacuum to the receiving space 18 can also be implemented in all other variants of the invention.

After closure of the hollow probe 10.4 it is removed from the tissue 40. Subsequent opening of the hollow probe 10.4 (FIG. 4i) and ejection of the severed portion 42 of tissue by means of the ejector 30 (FIG. 4j) are effected in a similar manner to the above-described variants of the invention.

Figure 5A:
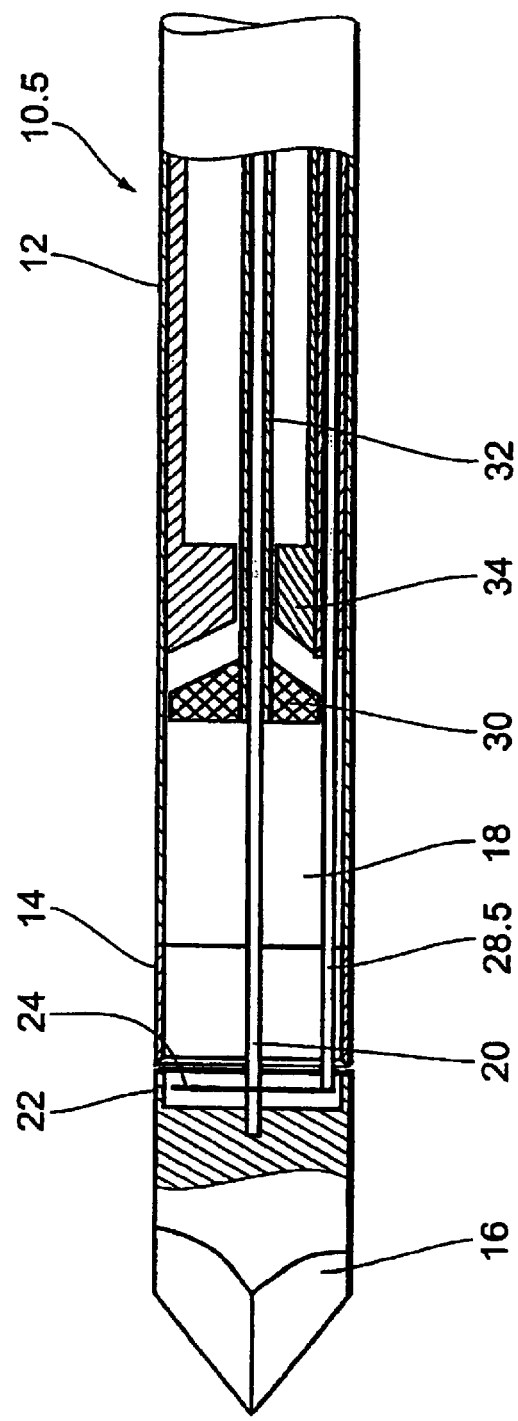
Figure 5B:
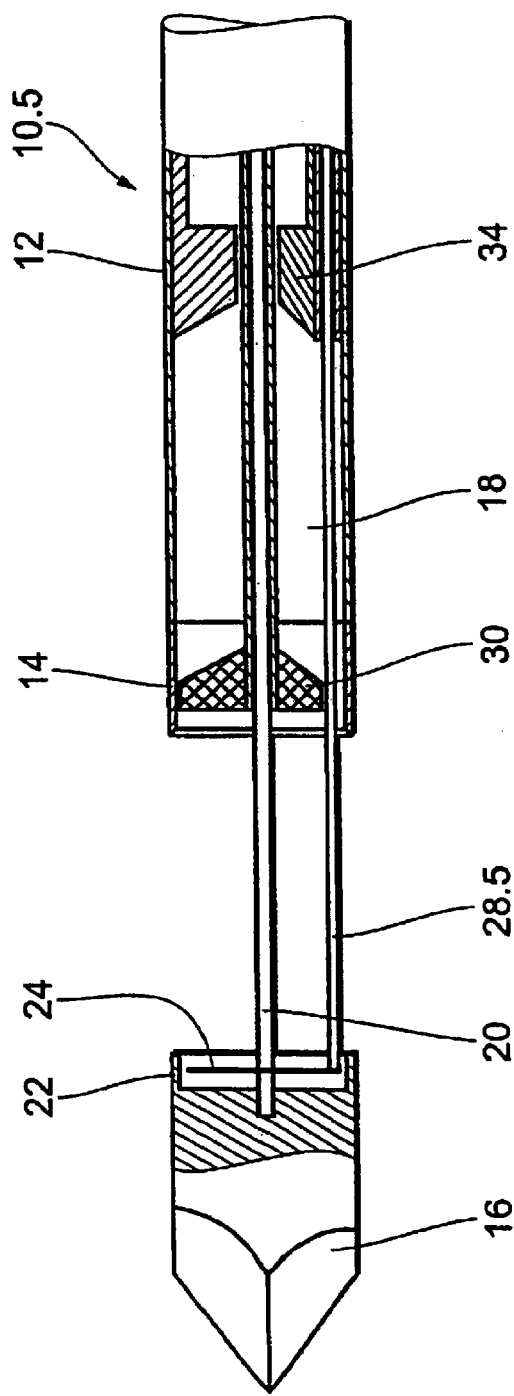
Figure 5C:
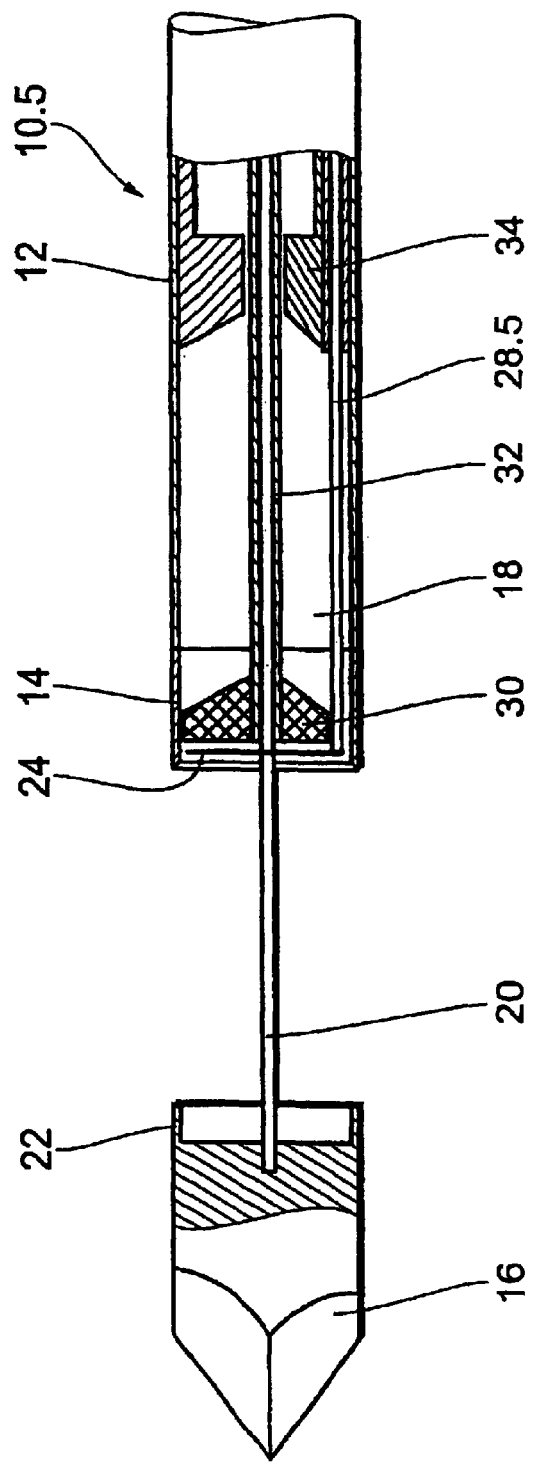
Figure 5D:
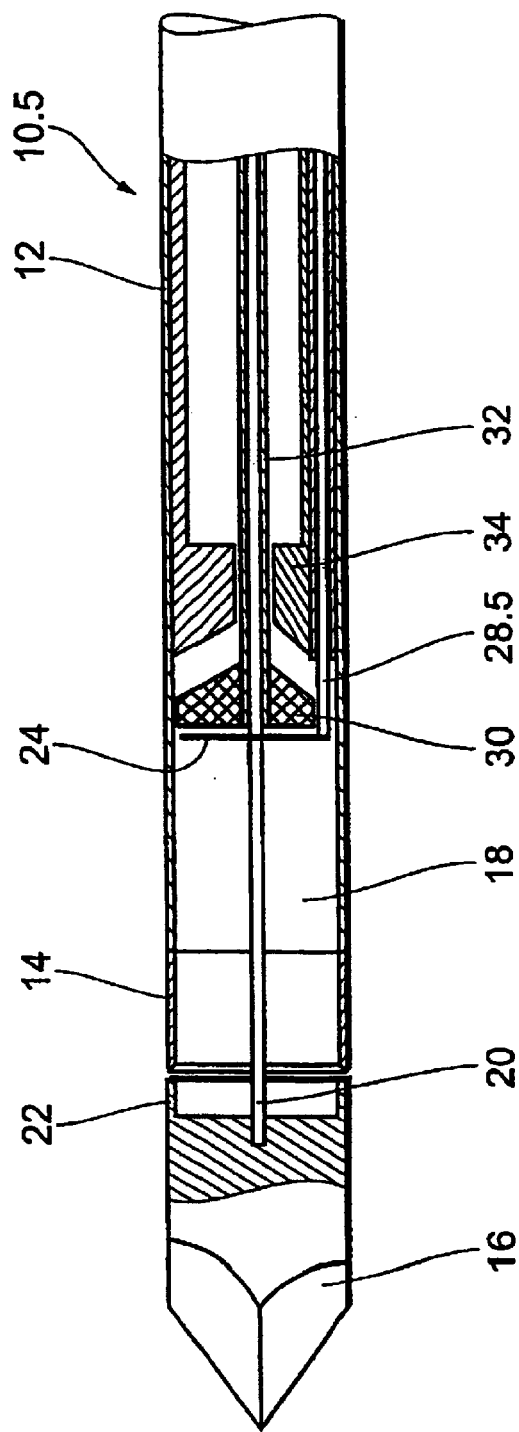
Figure 5E:
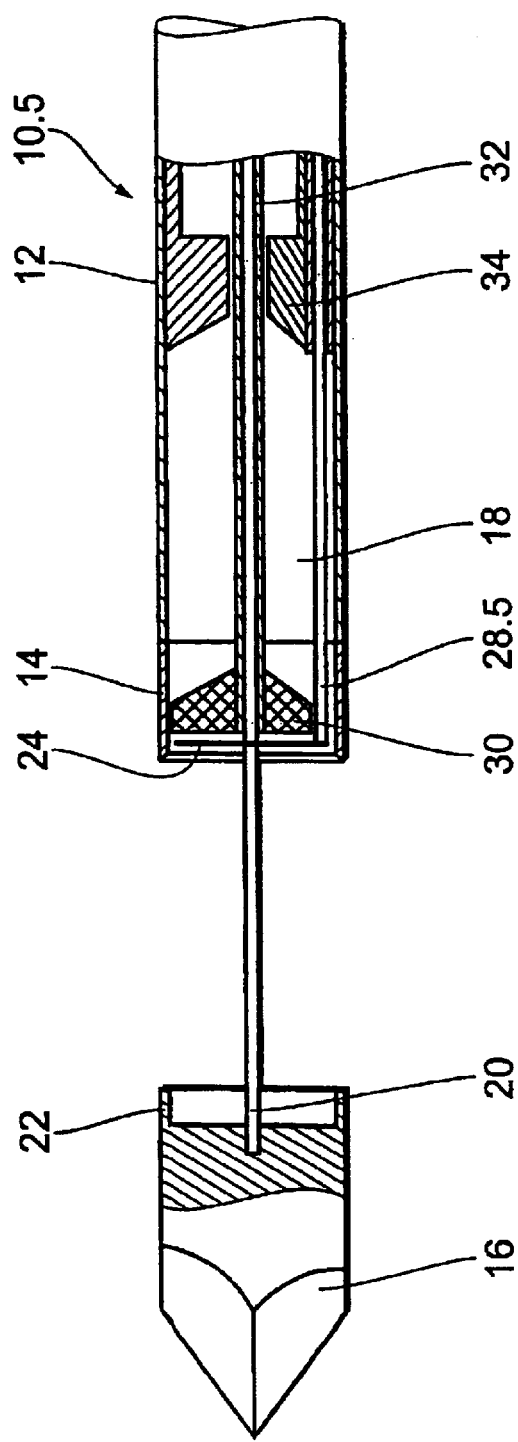

FIG. 5a shows a variant of the hollow probe 10.5. Similarly to the embodiments shown in FIGS. 2 and 3 the thrust rod 28.5 is arranged laterally of the receiving space 18. As in the case of the variant described with reference to FIG. 1 the metal tip 16 and the ejector 30 are movable separately by their own respective central thrust rods 20 and 32 respectively. The operating movements involved are similar to those shown in FIG. 1, with the difference that the ejector 30, upon retraction of the metal sleeve 12, after insertion of the hollow probe 10.5 into corresponding tissue, for opening the opening of the metal tip 16 and the metal sleeve 12, is not retracted with the metal sleeve 12 so that it is in the region of the distal end portion 14 of the metal sleeve 12 after opening of the hollow probe 10.5. The operation of cutting off a portion of tissue is effected by withdrawal of the cutting element 24 from the metal tip 16 to the distal end portion 14 of the metal sleeve 12. During closure of the hollow probe 10.5 the ejector 30 is withdrawn together with the cutting element 24 successively into the receiving space 18 and, if the ejector 30 bears sealingly against the wall of the metal sleeve 12, can promote the severed portion of tissue being sucked into the receiving space 18. Opening of the hollow probe 10.5 after removal thereof from the tissue and the ejection of severed tissue are effected similarly to the above-illustrated variants; see FIG. 5e.

Figure 6A:
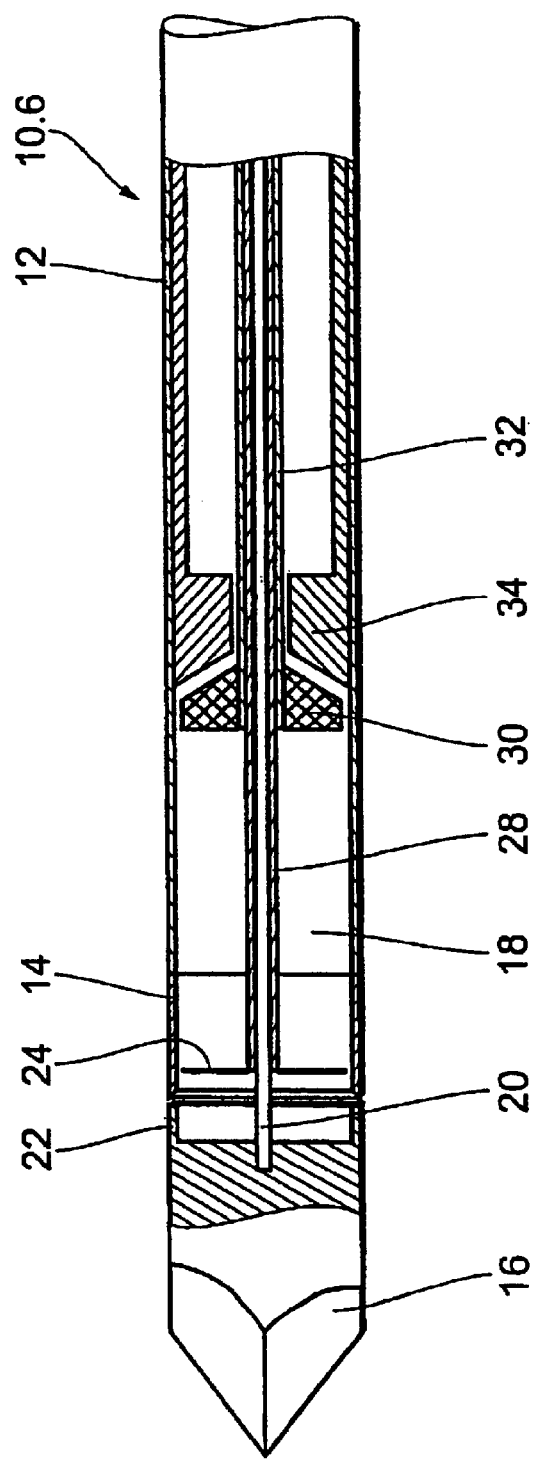
Figure 6B:
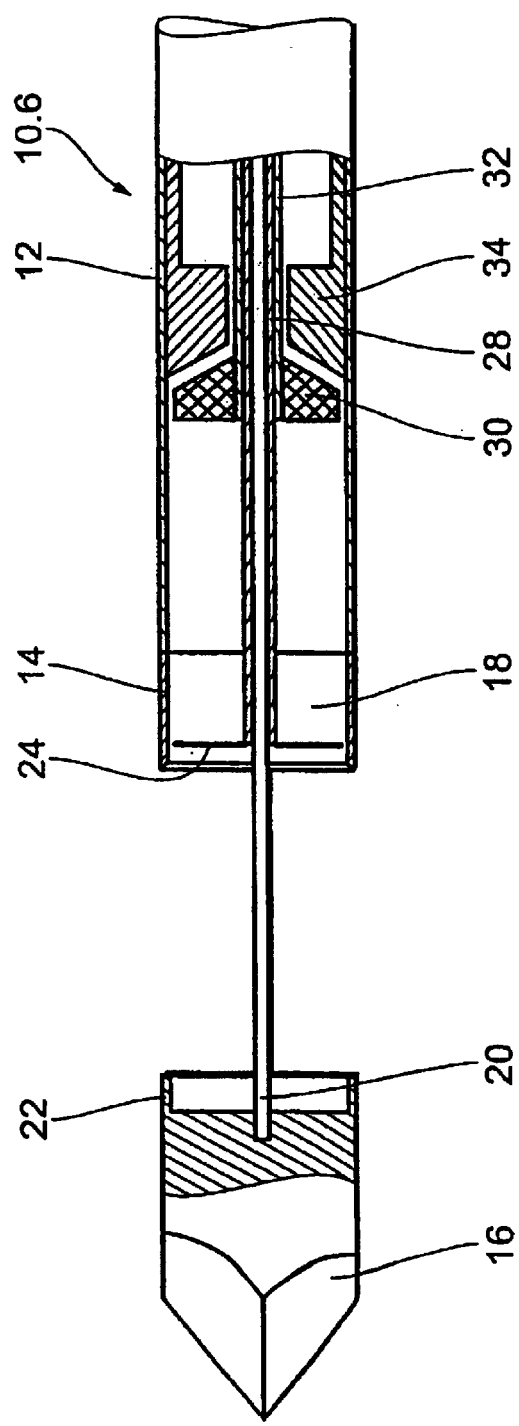
Figure 6C:
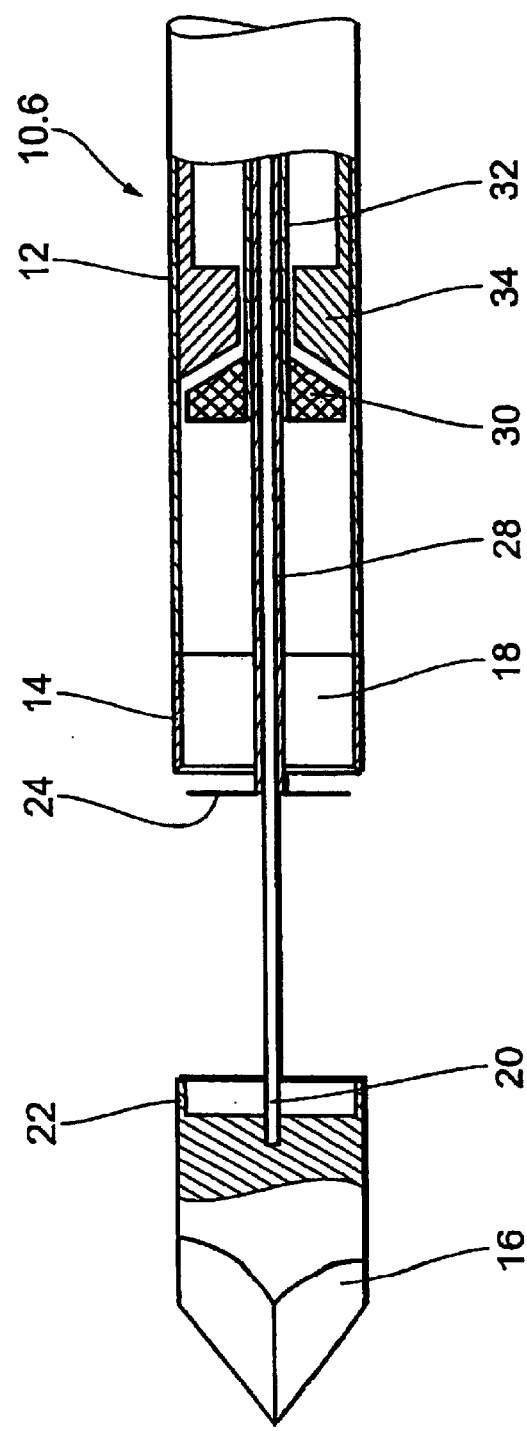
Figure 6D:
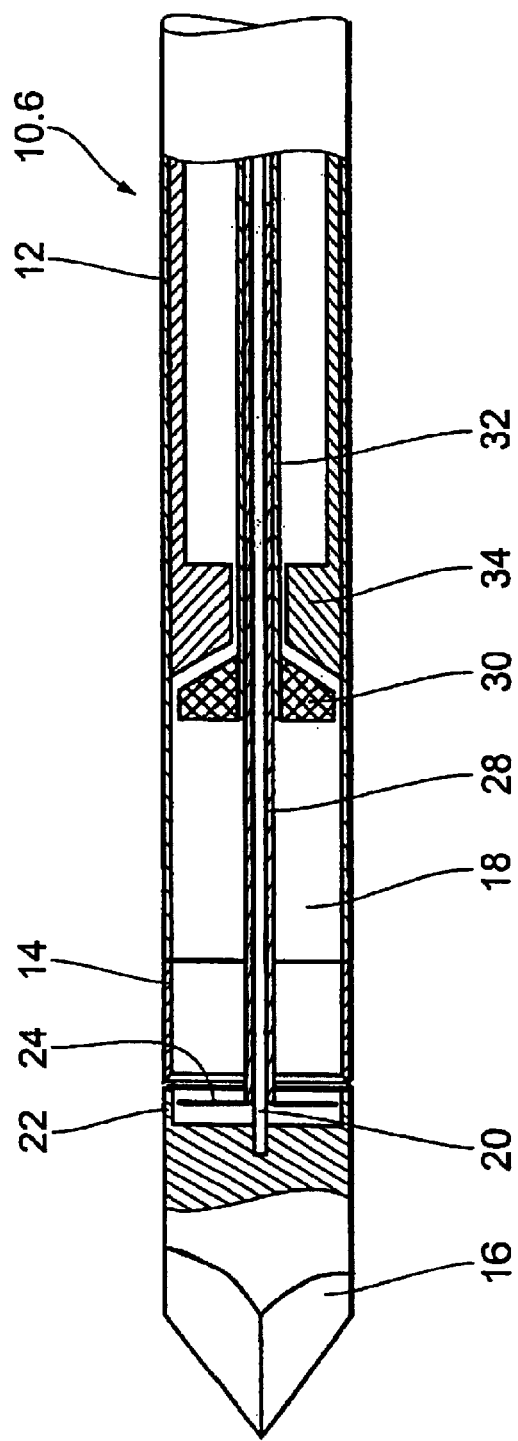
Figure 6E:
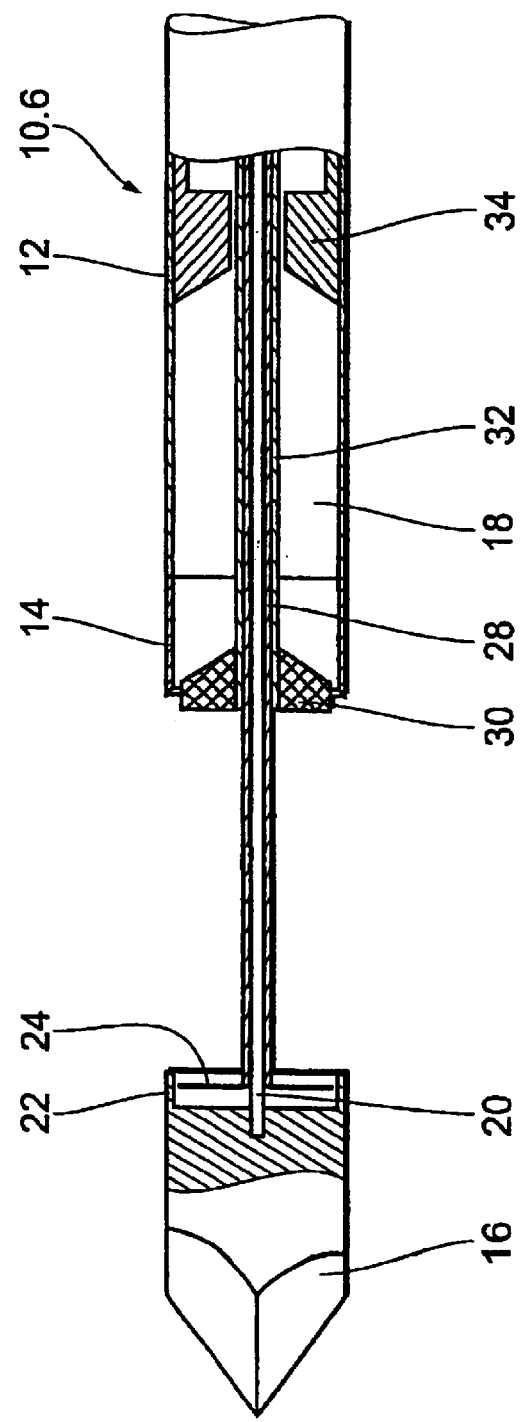
Figure 7A:
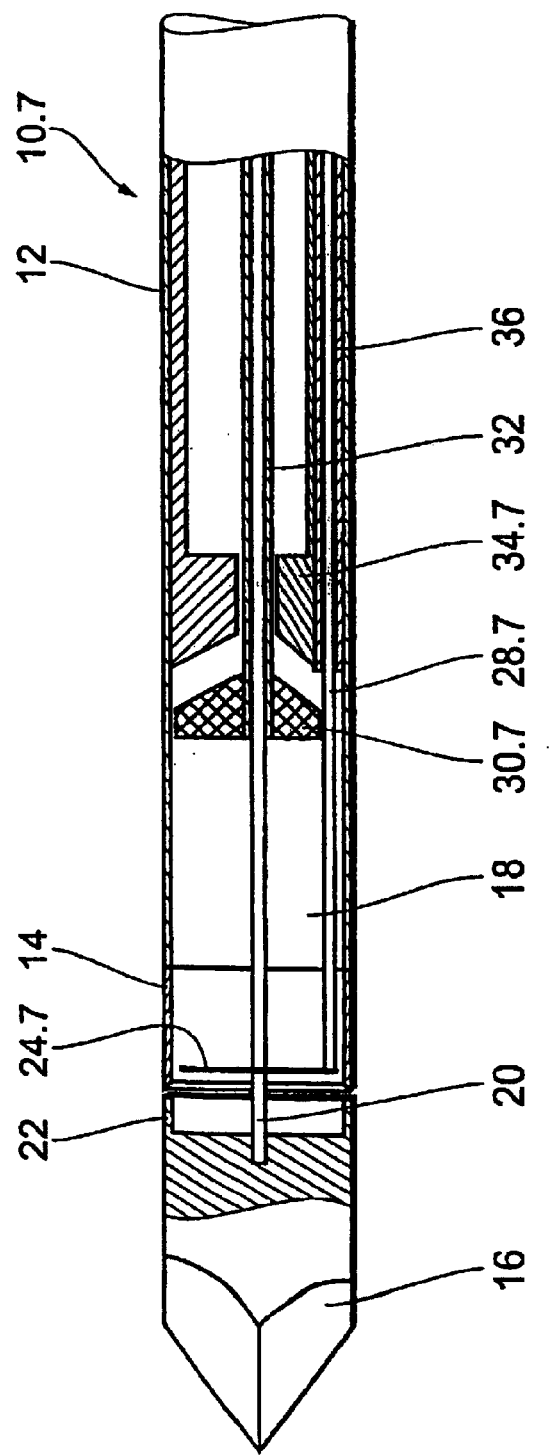
Figure 7B:
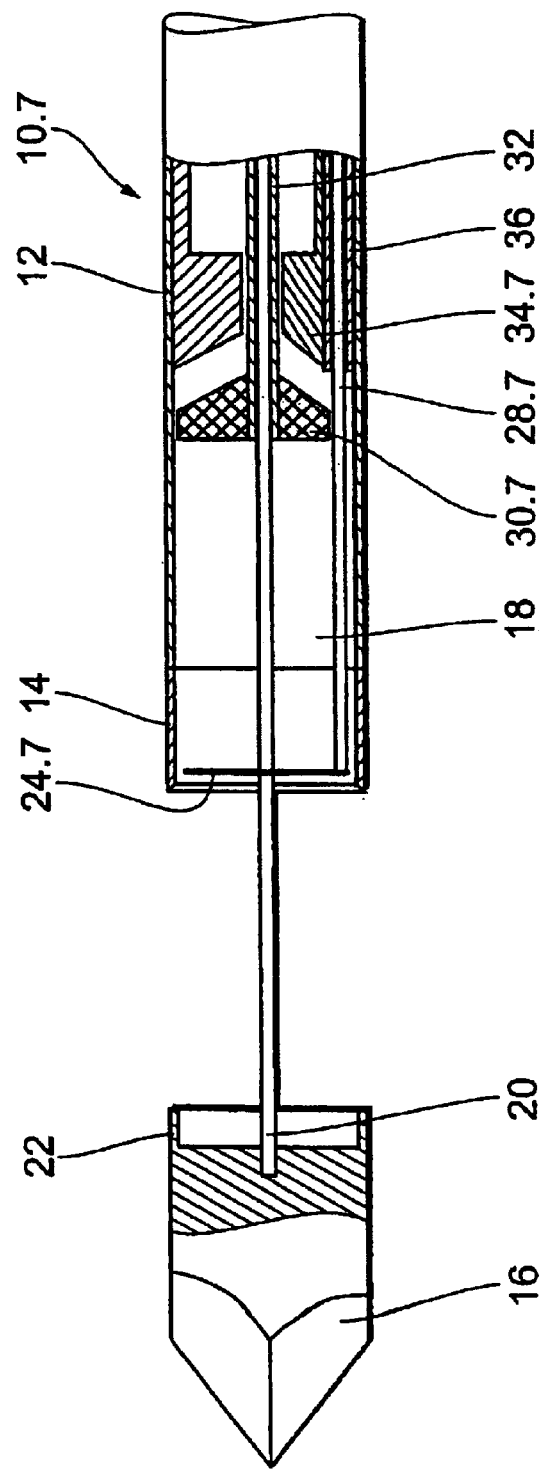
Figure 7C:
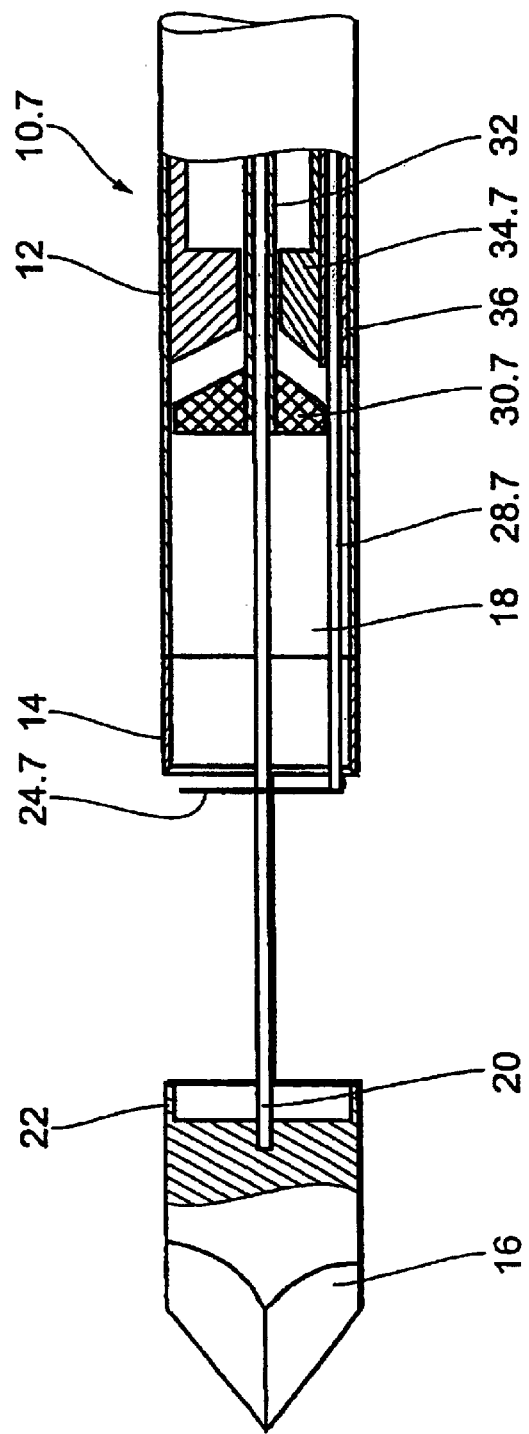
Figure 7D:
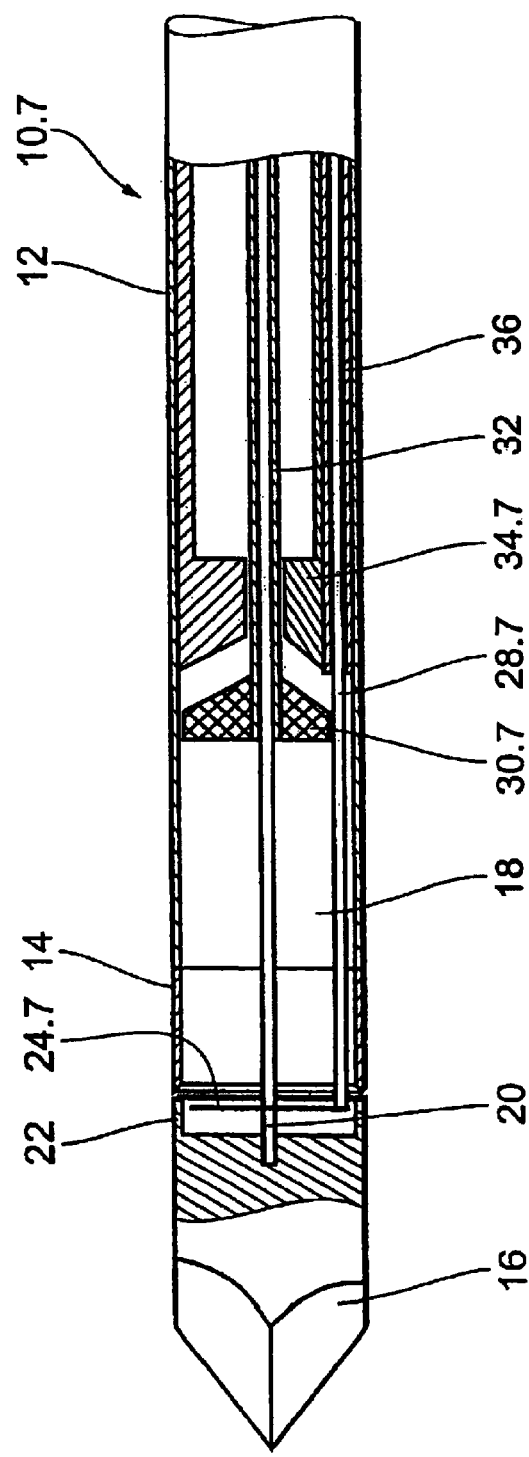
Figure 7E:
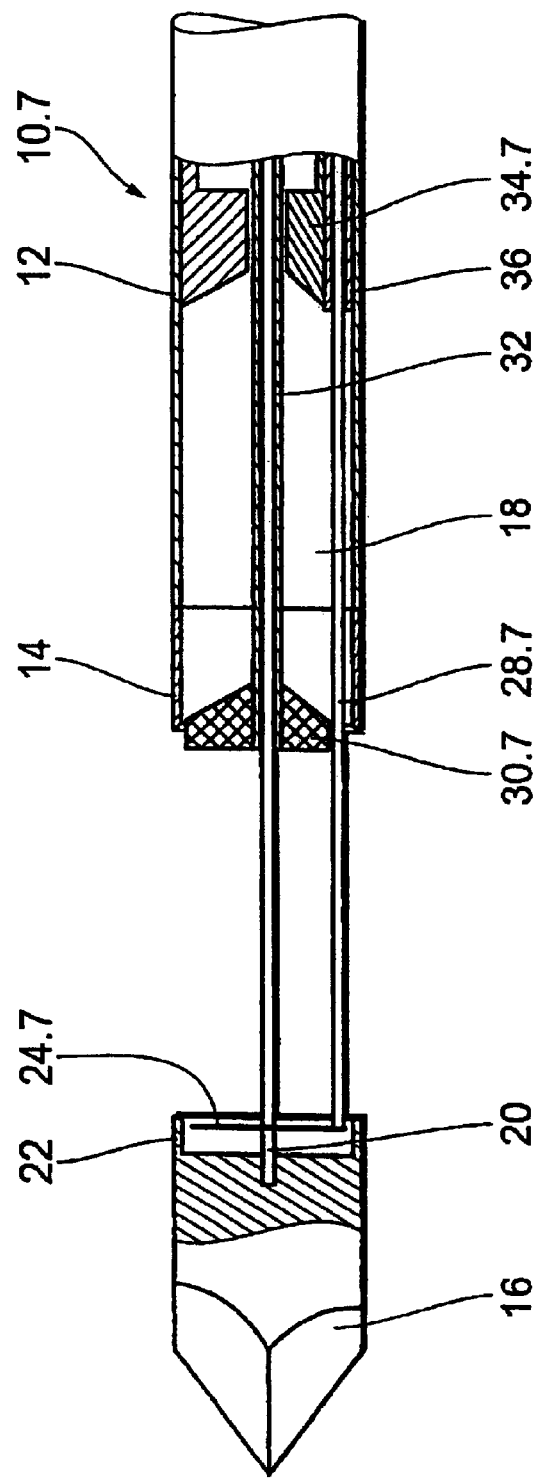

The hollow probe variant 10.6 shown in FIGS. 6a through 6e corresponds in its structure to the variant 10.1 shown in FIGS. 1a through 1l. Accordingly the metal tip 16, the cutting element 24 and the ejector 30 are each movable independently of each other by their respective separate thrust rods. The variants shown in FIGS. 1 and 6 differ in that the cutting element 24, after opening of the hollow probe 10.6, is not withdrawn from the metal tip 16 to the metal sleeve 12, but is advanced out of the receiving space 18 in the direction of the metal tip 16 so that, when the hollow probe 10.6 is in the open condition, tissue which penetrates into the opening between the metal tip 16 and the metal sleeve 12 is severed. FIG. 6e shows the position in which a severed portion of tissue is ejected.

The hollow probe variant 10.7 shown in FIGS. 7a through 7e corresponds in terms of its structure to the variant 10.5 shown in FIGS. 5a through 5e. Unlike the variant shown in FIG. 5 the cutting element 24, after opening of the hollow probe, is not withdrawn from the metal tip 16 into the distal end portion 14 of the metal sleeve 12 but is pushed out of the distal end portion 14 towards the metal tip 16. The operating movements involved therefore correspond to the variant shown in FIGS. 6a through 6e. The decentral thrust rod 28.7 for the cutting element 24 is guided in a guide sleeve 36.

Figure 8A:
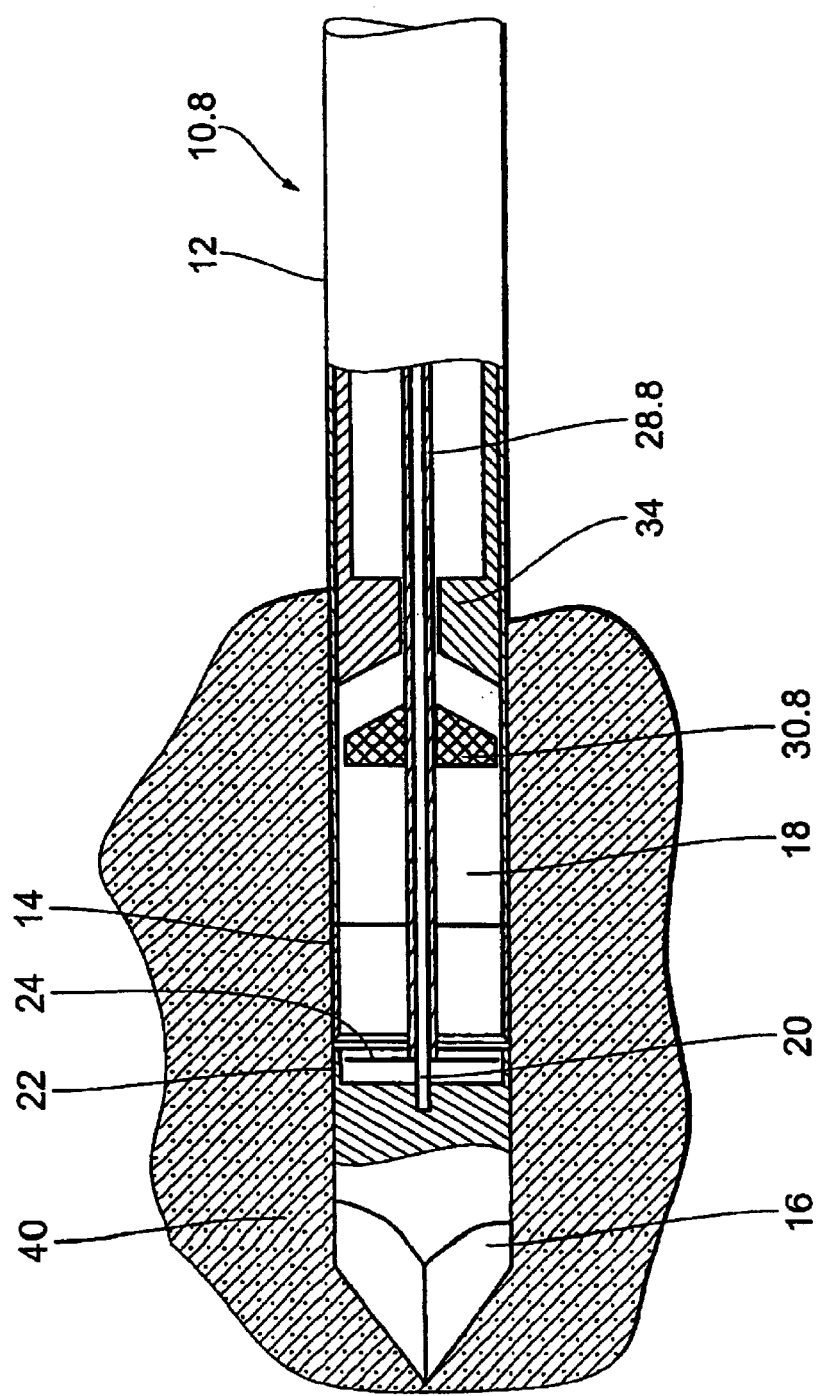
Figure 8B:
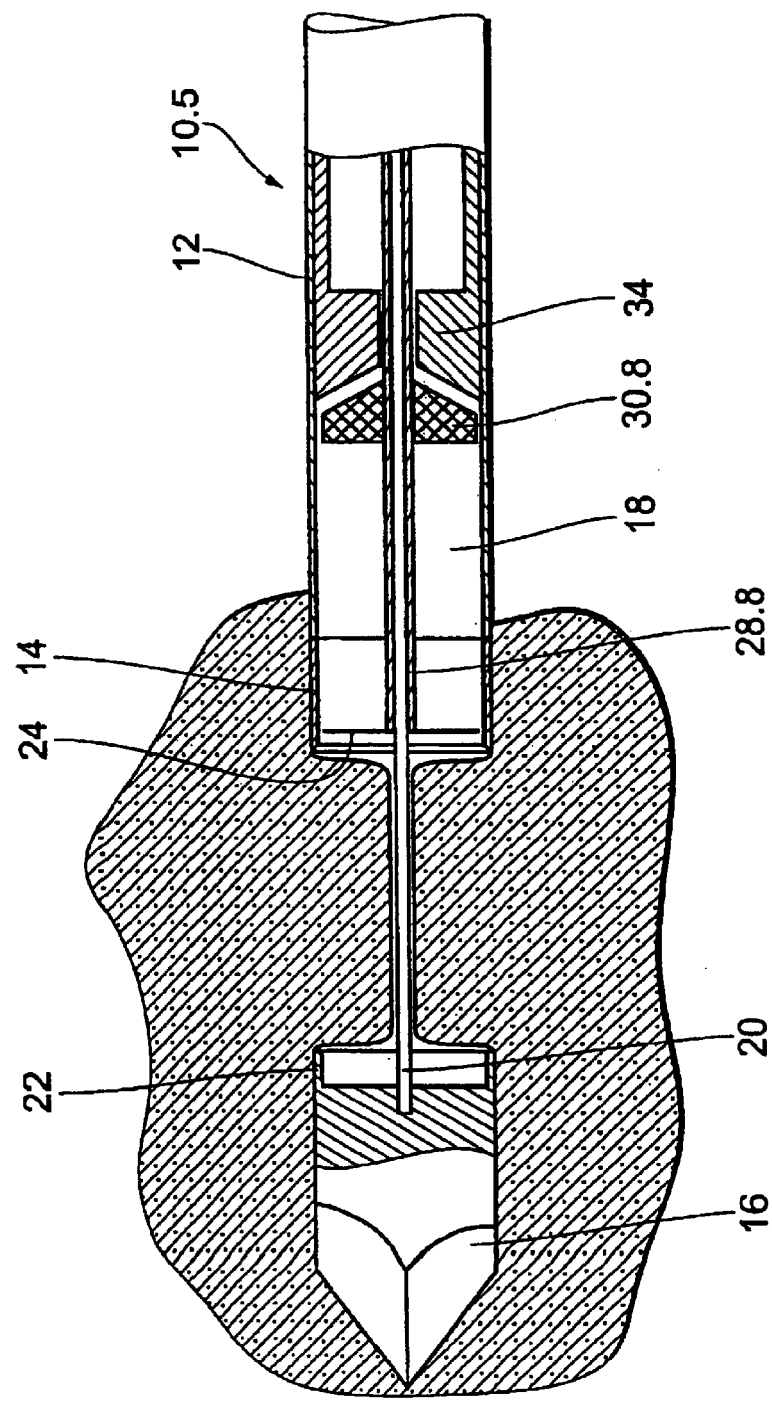
Figure 8C:
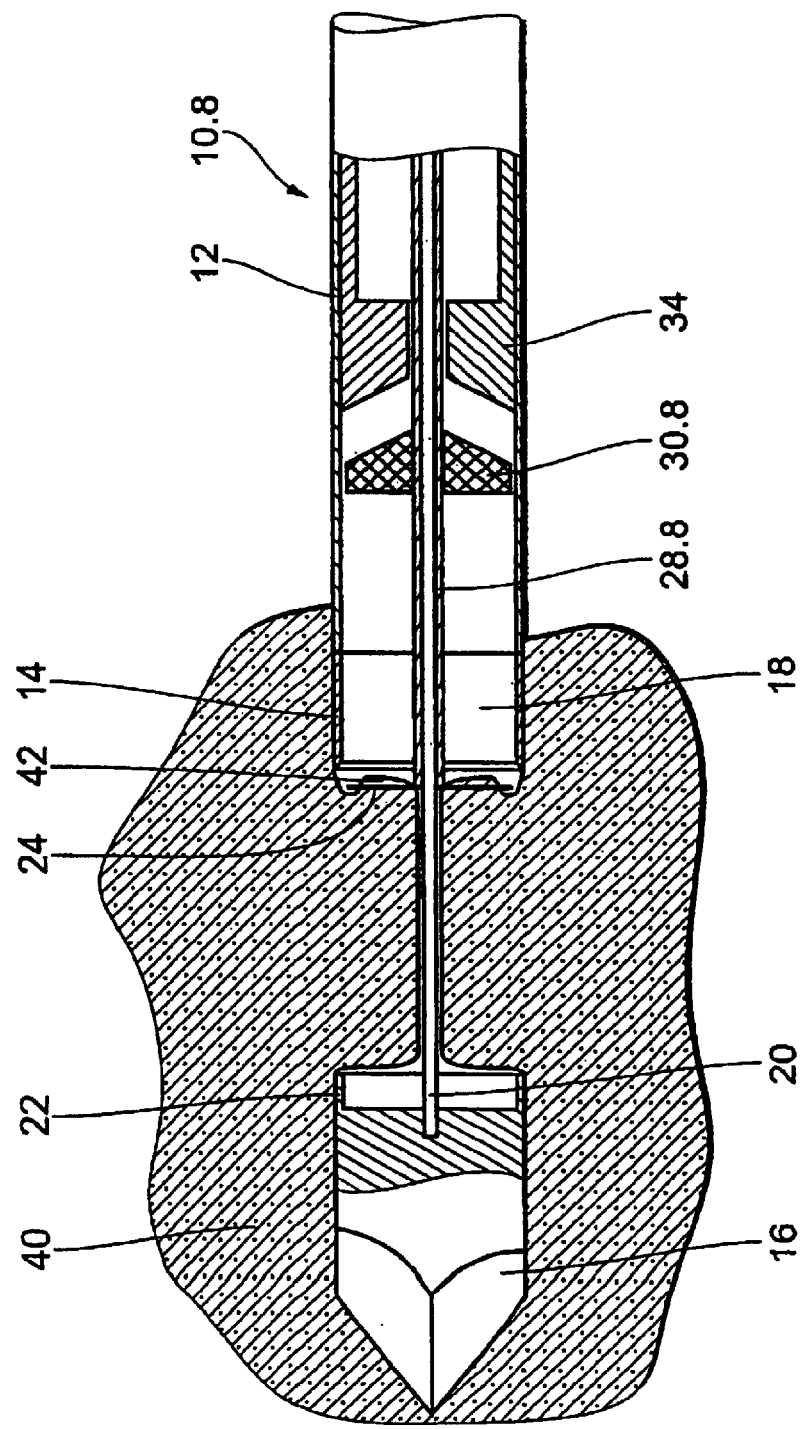
Figure 8D:
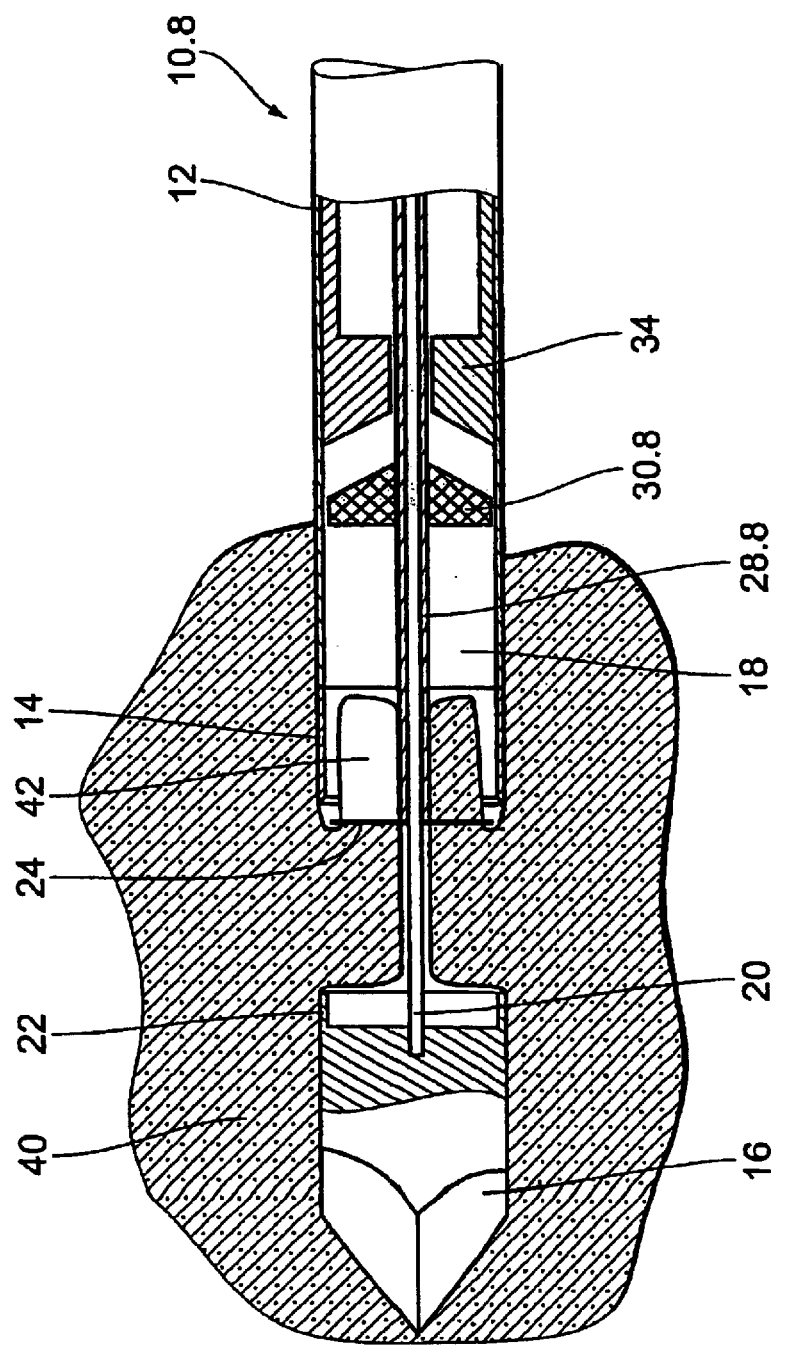
Figure 8E:
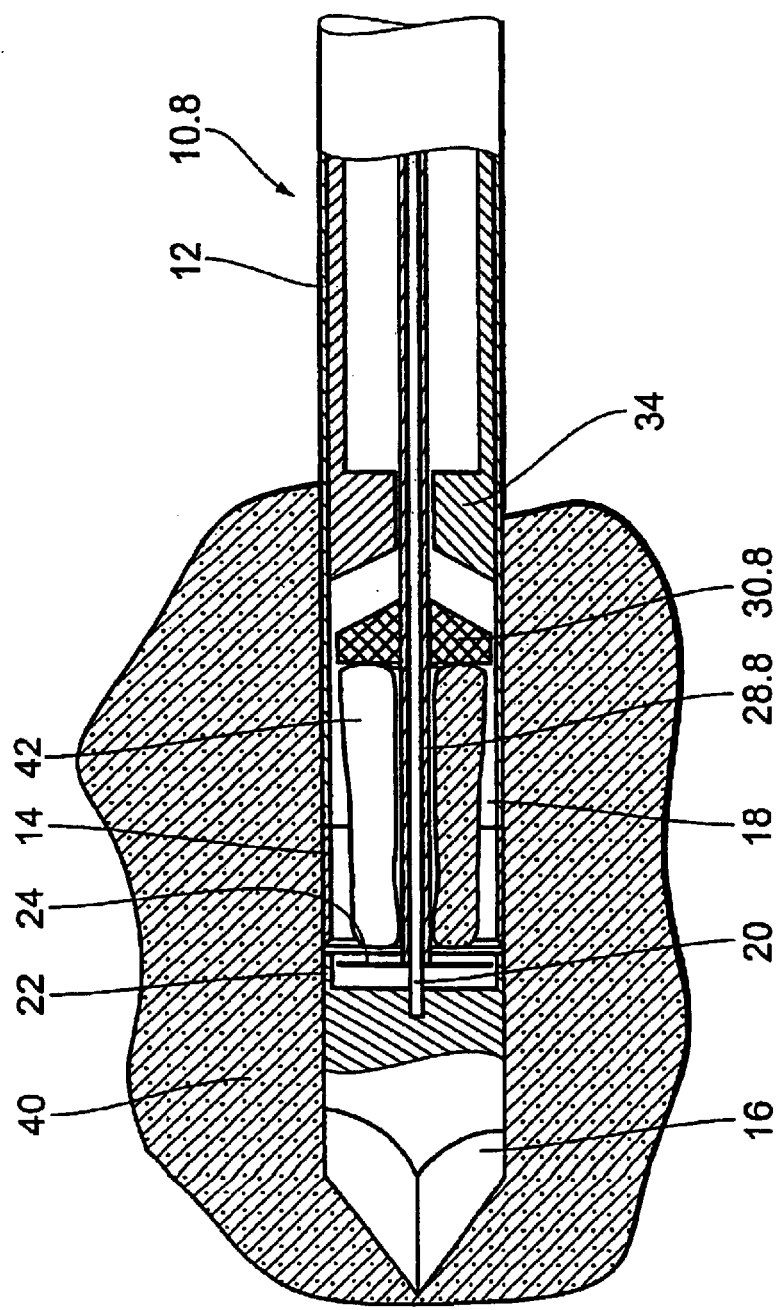
Figure 8F:
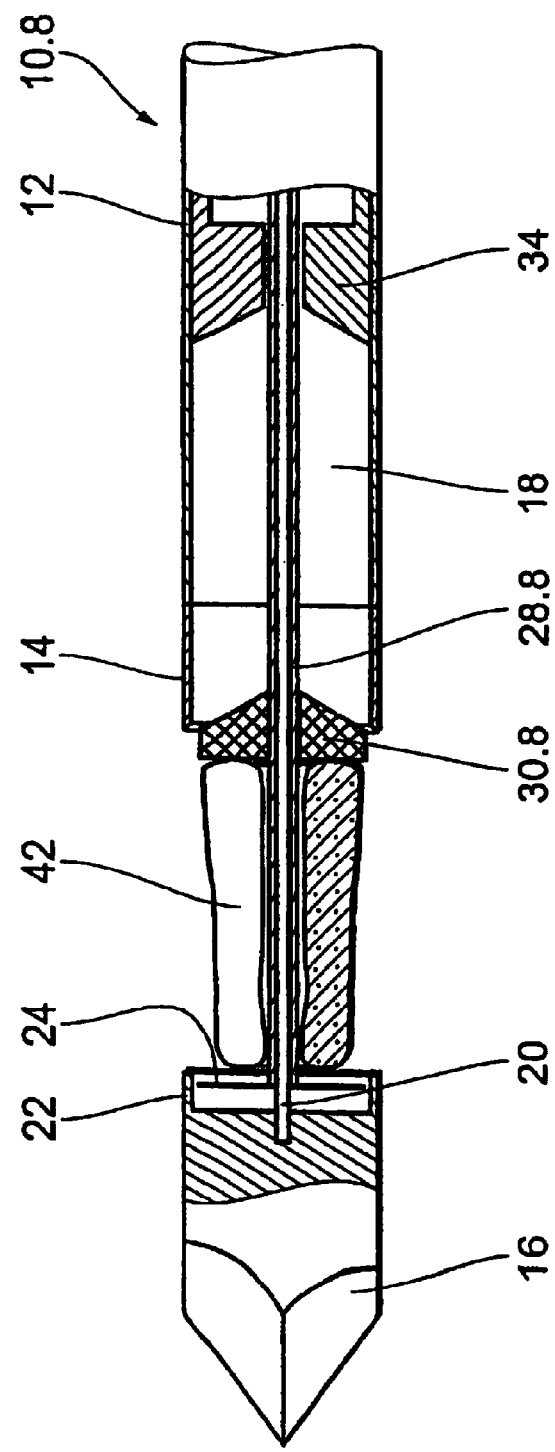

FIGS. 8a through 8f show a hollow probe 10.8 which is similar in its structure to the hollow probe 10.4 shown in FIGS. 4a through 4j. The hollow probe here has a central thrust rod 20 for the metal tip 16 and a common central thrust rod 28 for the cutting element 24 and the ejector 30. The receiving space 18 is overall smaller than in the variant shown in FIG. 4. As can be seen in particular from FIGS. 8c and 8d, after opening of the hollow probe 10.8 the metal sleeve 12 as well as the thrust rod 28 with the cutting element 24 and the ejector 30 are pushed together towards the metal tip 16. It is important in this respect that the cutting element 24 is arranged at a spacing—even if a small spacing—relative to the distal end of the metal sleeve 12 so that the cutting element 24 is free. While the metal sleeve 12 and the cutting element 24 are being pushed jointly towards the metal tip 16 the cutting element 24 cuts out a portion 42 of tissue which, during the advance movement of the metal sleeve 12, is likewise received in the receiving space 18. FIG. 8e shows the closed hollow probe 10.8 after total severing of the portion 42 of tissue. FIG. 8f shows the hollow probe 10.8 removed from the tissue 40 in the opened condition for ejection of the severed portion 42 of tissue.

Figure 9A:
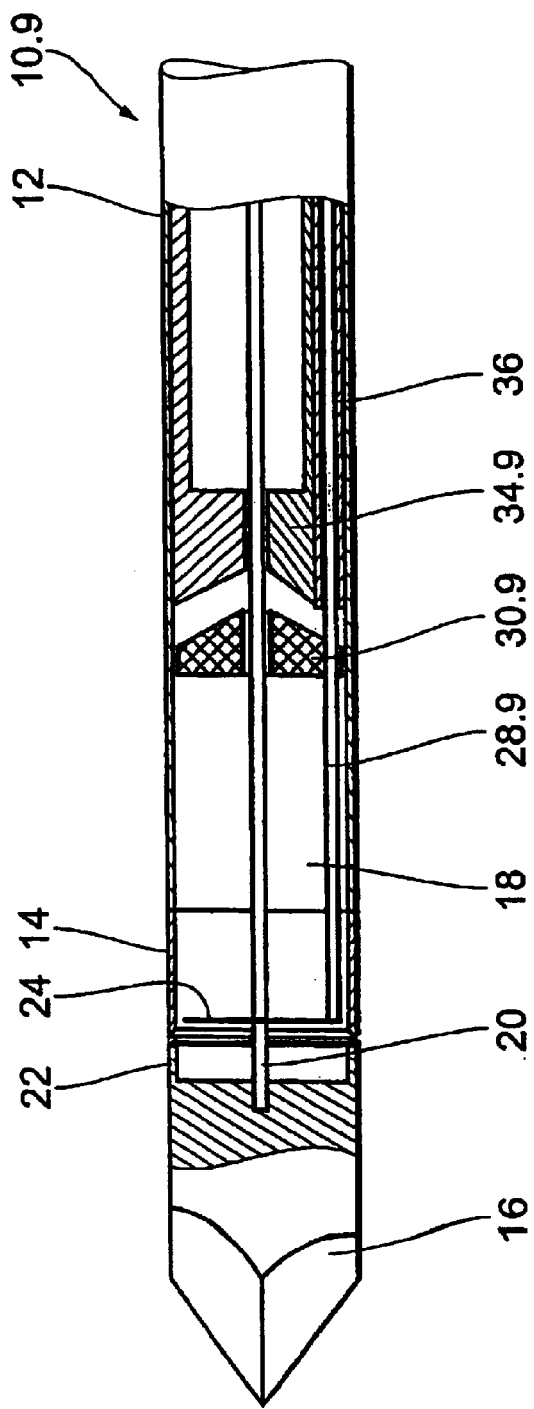
Figure 9B:
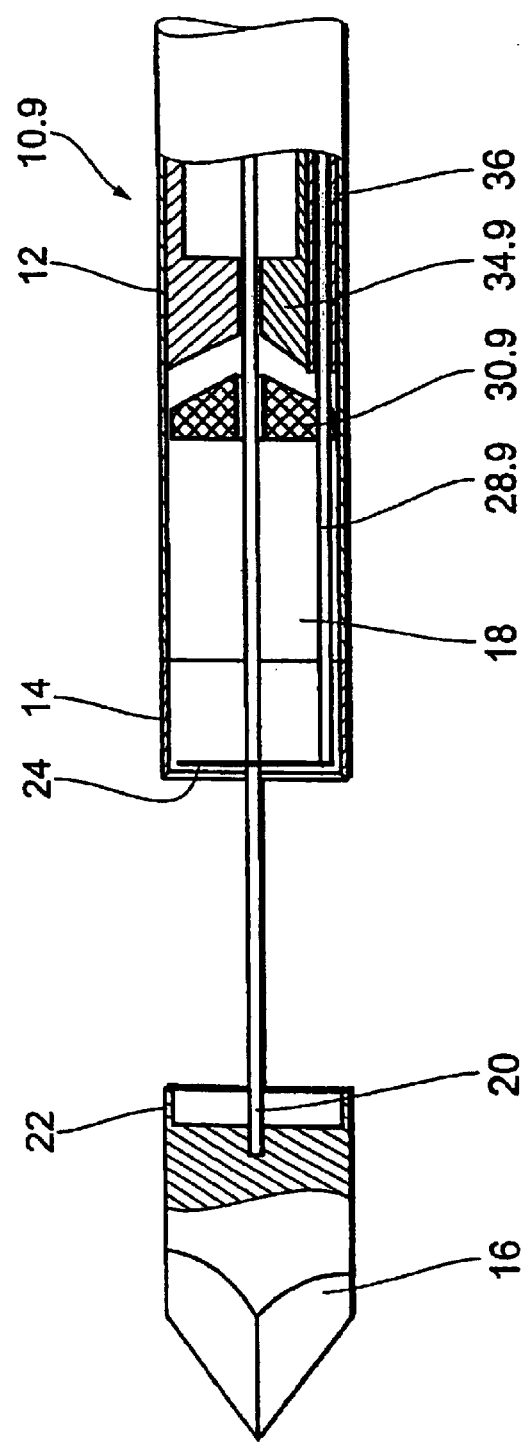
Figure 9C:
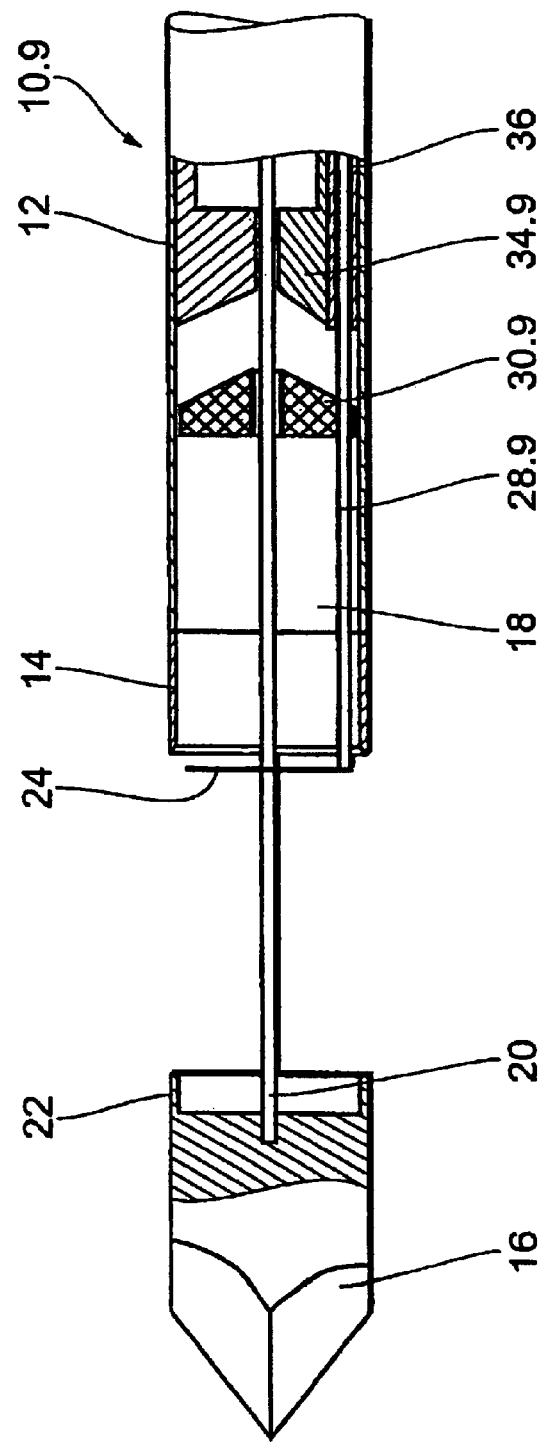
Figure 9D:
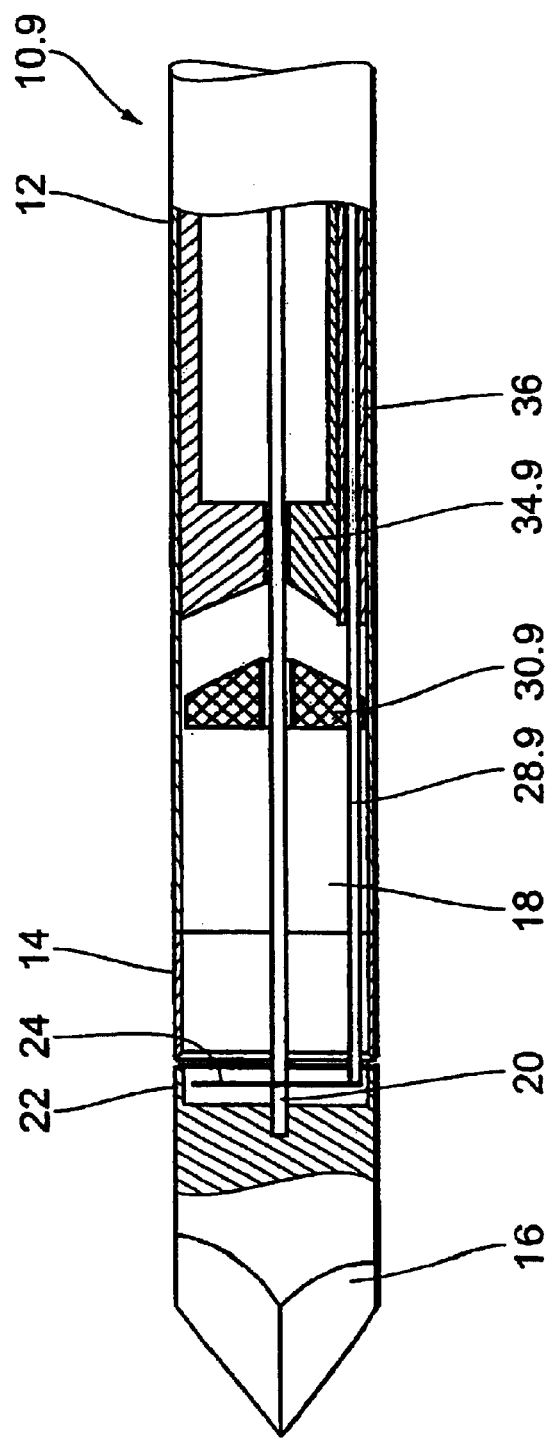
Figure 9E:
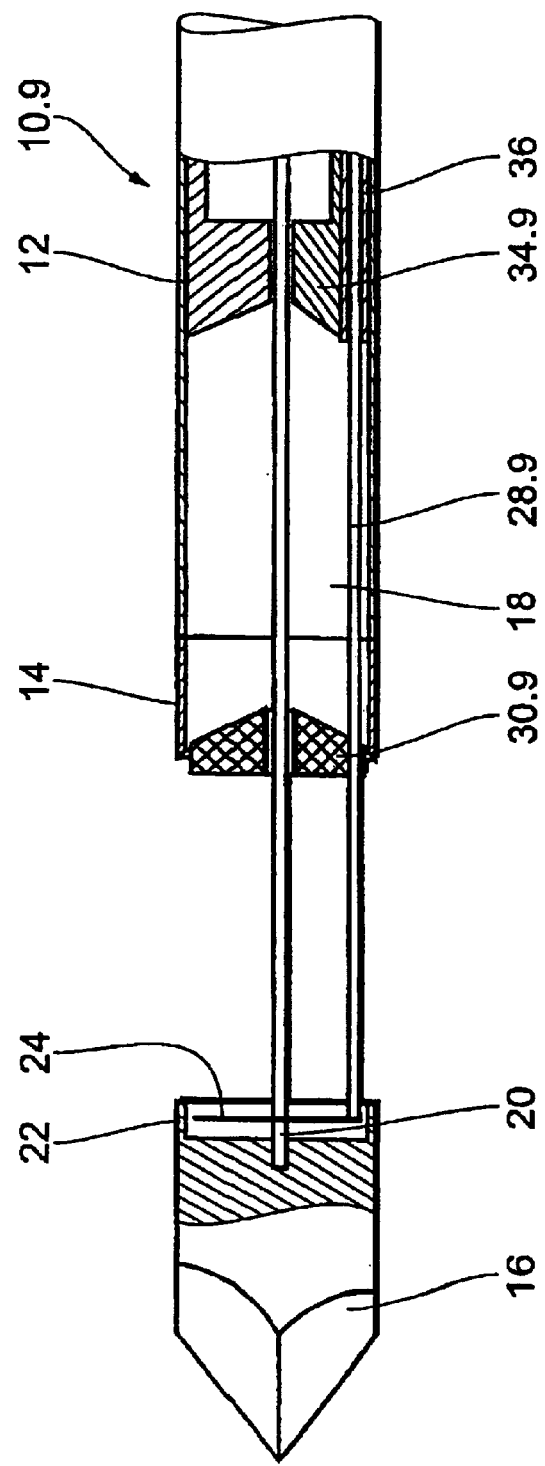

In the variant of a hollow probe 10.9 as shown in FIGS. 9a through 9e, instead of a common central thrust rod for the cutting element 24 and the ejector 30, there is a common decentral thrust rod 28.9 for the cutting element 24 and the ejector 30. The thrust rod 28.9 is guided in a guide sleeve 36. The operating movements involved when severing a portion of tissue are similar to those involved in the variant illustrated in FIG. 8. Unlike that construction the cutting element 24, upon opening of the hollow probe 10.9, is firstly retracted into the receiving space 18 and is then advanced somewhat in the direction of the metal tip 16, to sever the portion of tissue, so that the cutting element 24 is free; see FIG. 9c. Then the cutting element 24 together with the ejector 30 and the metal sleeve 12 are pushed towards the metal tip 16 so that a portion of tissue is severed in the same manner as shown in FIGS. 8a through 8e. FIG. 9d shows the closed probe 10.9 after severing a portion of tissue, while FIG. 9e shows the hollow probe 10.9 which is opened for ejection of a portion of tissue, after removal of the probe from the tissue.

FIGS. 10a through 10h show various variants of a cutting element 24 connected to a central thrust rod 28. Shown in each thereof are one or more struts 26 with which the respective cutting element 24 is connected to the respective thrust rod 28. The struts 26 are preferably of the same diameter as the cutting element 24 formed by a wire ring. The wire diameter is between 0.05 and 1.0 mm, preferably being 0.15 mm. The thrust rod 28 in each case is in the form of a tube so that a further thrust rod for the metal tip of the respective hollow probe can be guided in the thrust rod 28. The wire struts 26 not only involve the purpose of holding the cutting element 24 but they also have the property of longitudinally cutting severed portions of tissue, as described hereinbefore.

FIGS. 11a through 11k each show a respective thrust rod 28 with a cutting element 24 fixed thereto and formed by a wire ring. In the illustrated variants, wire struts are evidently not required for holding the cutting element 24 to the thrust rod 28. Thus the sole purpose of the wire struts 26 shown in FIGS. 11a through 11h is to serve as a cutting electrode for longitudinal slitting of a severed portion of tissue. As shown in FIGS. 11i through 11k a wire strut 26 can also be in the form of a wire loop. The front view of the wire loop 26 shown in FIGS. 11i through 11k is the same as that of the wire strut 26 shown in FIG. 11a so that the same cut is produced upon movement of the thrust rod 28 in the longitudinal direction in both cases.

Figure 12:
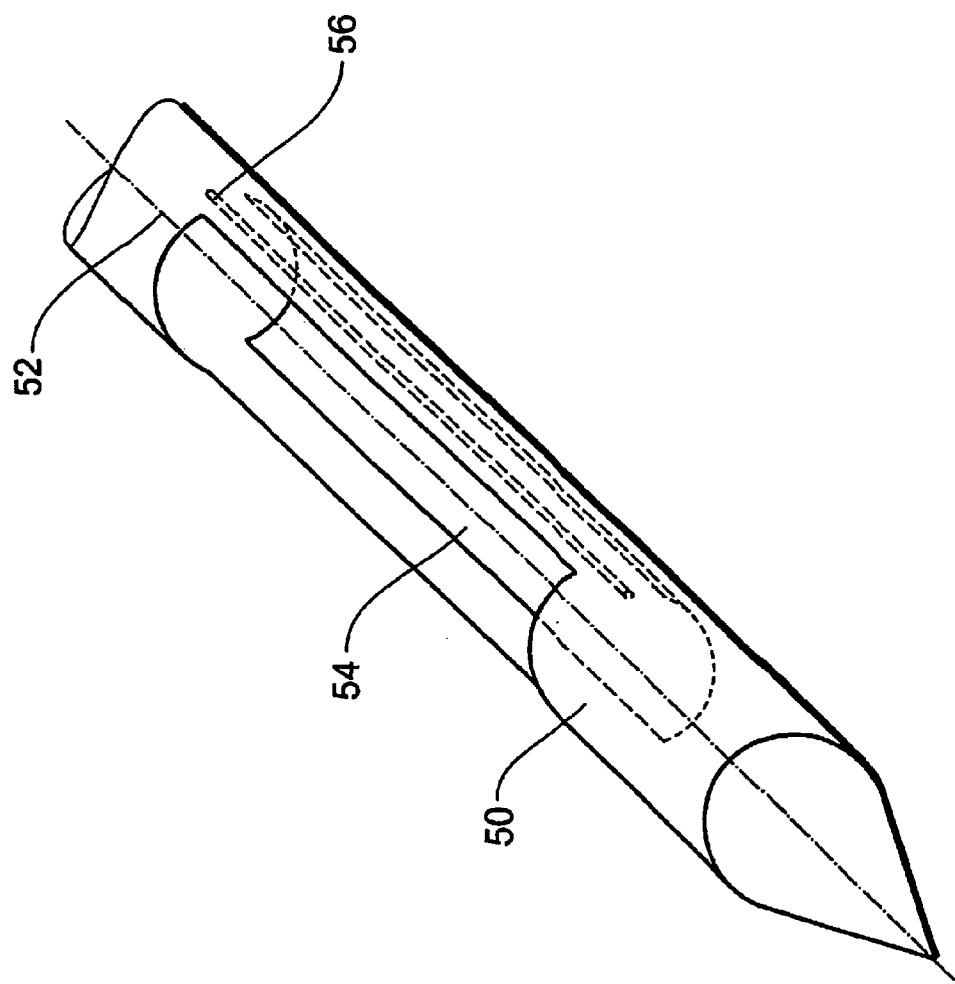
FIG. 12 is a diagrammatic perspective view showing an alternative hollow probe.
Figure 13C:
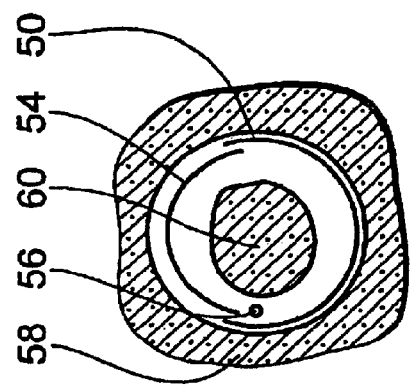
FIGS. 13 and 14 are diagrammatic sectional views of the hollow probe of FIG. 12 in various operating conditions.
Figure 13B:
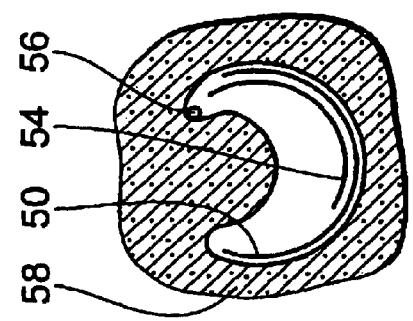
Figure 13A:
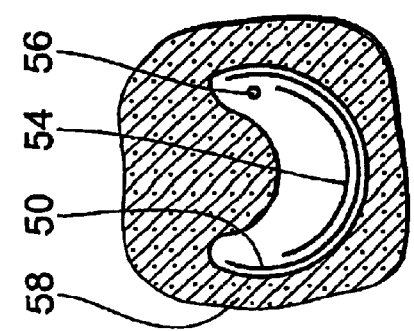
Figure 14D:
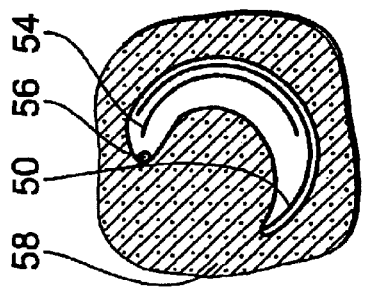
Figure 14C:
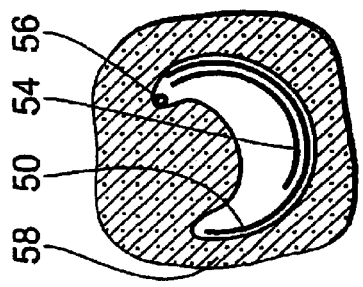
Figure 14B:
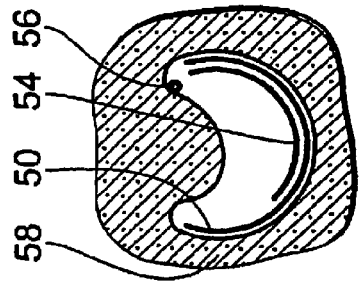
Figure 14A:
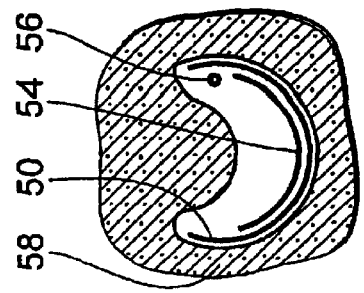
Figure 14H:
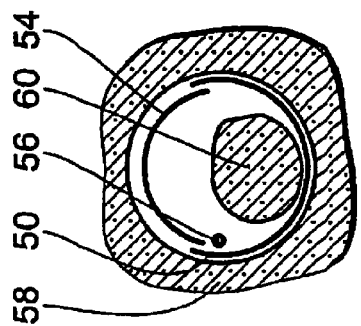
Figure 14G:
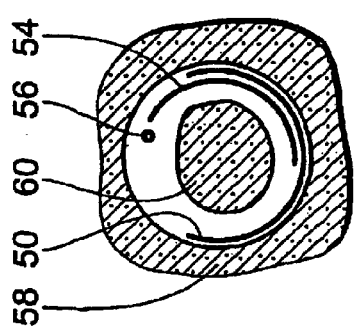
Figure 14F:
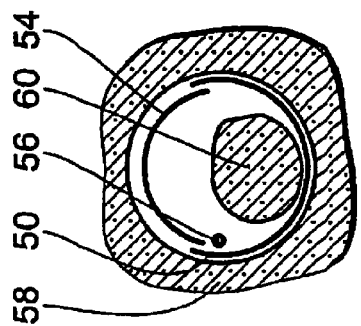
Figure 14E:
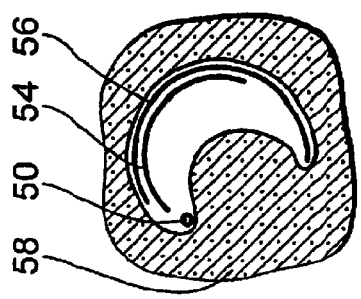

FIG. 12 shows an alternative hollow probe 50 in which a cylindrical receiving space is open outwardly at one half side. That opening is to be closed by a cover 54 rotatable about the longitudinal axis 52 of the hollow probe 50. Mounted in front of a longitudinal edge of the cover is a straight cutting element 56 which is oriented in parallel relationship with the longitudinal axis 52 of the hollow probe 50. Vacuum can preferably be applied to the hollow probe 50, tissue 58 being sucked by means of the vacuum into the hollow probe 50 in the opened condition. To close the opening the cover 54 together with the cutting element 56 is rotated about the longitudinal axis 52 of the hollow probe 50 in such a way that the cutting element 56 precedes the cover 54 and severs the portion 60 of tissue which has been sucked into the opening of the hollow probe 50. That is shown in FIGS. 13a through 13c.

In order to be able to sever a larger portion of tissue with the hollow probe 50 shown in FIG. 12, in a simple manner, the opened hollow probe 50 with the cutting element 56 in a free and exposed condition can be rotated about its longitudinal axis 52 in the tissue 58, see FIGS. 14a through 14h, in order in that way to pare out a corresponding tissue portion 60. The hollow probe 50 is then closed again and removed from the tissue.

FIG. 15 shows a perspective view of a variant of the hollow probe 10.3 shown in FIGS. 3a through 3e.

FIG. 16 shows a surgical apparatus 70 with a hollow probe 72 which is equipped with two electrodes 74, 76 for introducing high-frequency electrical current into tissue surrounding the hollow probe 72. The two electrodes 74 and 76 are connected by way of electrical lines 78 and 80 to a generator 82 for producing the electrical power to be introduced into the tissue. Also connected to the lines is a measuring unit 84 which is adapted to determine the impedance between the two electrodes 72 and 74. The measuring device 84 is connected to the generator in order to control the output power thereof in dependence on the impedance measured between the electrodes 74 and 76. That feedback of the impedance measurement values affords overall a generator regulation effect. Control of the generator 82 by means of the impedance signal an also be used for switching off the generator 82 in an appropriate manner suited to the therapy involved. With increasing sclerosis of the tissue the impedance thereof rises. Therefore it is possible to provide a limit value in respect of impedance, from which the generator is switched off, as the measured high specific tissue impedance shows that the tissue has been sufficiently sclerosed.

What is claimed is:

1. A surgical probe for the minimally invasive removal of tissue, comprising:
an elongate hollow body comprising a first segment and a second segment, at least the first segment includes an open cavity for receiving tissue and the second segment engages the open cavity of the first segment to enclose a hollow space, the first and second segments being movable relative to each other to selectively open or close access to the hollow space; and
an electrically conductive ring-shaped or loop-shaped wire cutting element, separate from the first and second segment, which is movable relative to at least one of the segments and which is adapted for electrosurgically cutting out tissue which has penetrated into an opening between the hollow body segments when the segments are in an open configuration.

2. The surgical probe of claim 1, comprising:
an ejector for ejecting tissue from the hollow probe.

3. The surgical probe of claim 2, wherein:
the cutting element is exposed or is movable into an exposed position.

4. The surgical probe of claim 3, wherein:
the cutting element is electrically conductive in the form of a cutting electrode for the application of an HF-voltage.

5. The surgical probe of claim 4, wherein:
the two segments are separable from each other along a peripheral line around the cavity.

6. The surgical probe of claim 4, wherein:
the cutting element is axially displaceable and has an electrically conductive loop which is shaped to cut out a cylindrical or prism-shaped portion of tissue.

7. The surgical probe of claim 5, wherein:
the two segments are axially displaceable relative to each other.

8. The surgical probe of claim 7, wherein:
the opening between the segments is cylindrical or prism-shaped, depending on the respective cross-sectional shape of the cavity.

9. The surgical probe of claim 8, wherein:
a thrust rod guided in one of the two segments connects the two segments.

10. The surgical probe of claim 9, wherein:
the thrust rod extends centrally in the cavity enclosed by the segments.

11. The surgical probe of claim 10, wherein:
the cutting element is axially displaceable and has an electrically conductive loop which is shaped to cut out a cylindrical or prism-shaped portion of tissue.

12. The surgical probe of claim 11, wherein:
the cutting element has a cutting arm which extends between the thrust rod and the electrically conductive loop and is connected thereto in an electrically conductive manner.

13. The surgical probe of claim 12, wherein:
the cutting element is displaceable within at least one of the opening and the cavity.

14. The surgical probe of claim 13, wherein:
the two segments which are movable relative to each other are in the form of electrodes for apply an HF-voltage for thermal inactivation of tissue.

15. The surgical probe of claim 14, wherein:
the two segments are separated from each other near a distal end of the hollow probe.

16. The surgical probe of claim 15, wherein:
one of the segments forms a sharpened metal tip at the distal end of the hollow probe.

17. The surgical probe of claim 16, wherein:
the ejector is arranged axially displaceably within the cavity.

18. The surgical probe of claim 17, wherein:
the ejector is arranged displaceably out of a rest position at one end of the cavity in the direction of the cavity and on a side thereof towards the cavity in the rest position carries a severing blade which is towards the cavity.

19. The surgical probe of claim 17, wherein:
the cutting element and the ejector are fixed to a common thrust rod which is guided longitudinally slidably with respect to the segments.

20. A surgical apparatus for excising tissue, comprising:
a hollow probe as defined in claim 14 wherein two electrodes of the hollow probe are adapted to deliver electrical energy to tissue surrounding the hollow probe, and are connected to a measuring device which is adapted to produce a signal dependent on an impedance measured between the two electrodes.

21. The surgical apparatus of claim 20, wherein:
the measuring device is connected to a generator of electrical energy to be delivered by way of the electrodes such that an electrical power delivered from the generator is controllable by the signal produced by the measurement device.

22. The surgical probe of claim 1, wherein:
the cutting element is exposed or is movable into an exposed position.

23. The surgical probe of claim 1, wherein:
the cutting element is electrically conductive in the form of a cutting electrode for the application of an HF-voltage.

24. The surgical probe of claim 1, wherein:
the two segments are separable from each other along a peripheral line around the cavity.

25. The surgical probe of claim 1, wherein:
the two segments are axially displaceable relative to each other.

26. The surgical probe of claim 25, wherein:
the opening between the segments is cylindrical or prism-shaped, depending on the respective cross-sectional shape of the cavity.

27. The surgical probe of claim 1, wherein:
a thrust rod guided in one of the two segments connects the two segments.

28. The surgical probe of claim 27, wherein:
the thrust rod extends centrally in the cavity enclosed by the segments.

29. The surgical probe of claim 1, wherein:
the cutting element is displaceable within at least one of the opening and the cavity.

30. The surgical probe of claim 1, wherein:
the two segments which are movable relative to each other are in the form of electrodes for apply an HF-voltage for thermal inactivation of tissue.

31. The surgical probe of claim 1, wherein:
the two segments are separated from each other near a distal end of the hollow probe.

32. The surgical probe of claim 1, wherein:
one of the segments forms a sharpened metal tip at a distal end of the hollow probe.

33. A surgical probe for the minimally invasive removal of tissue, comprising:
an elongate hollow body comprising a first segment and a second segment, at least the first segment includes an open cavity for receiving tissue and the second segment engages the open cavity of the first segment to enclose a hollow space, the first and second segments being movable relative to each other to selectively open or close access to the hollow space;
an electrically conductive ring-shaved or loop-shaped cutting element which is movable relative to at least one of the segments and which is adapted for electrosurgically cutting out tissue which has penetrated into an opening between the hollow body segments when the segments are in an open configuration; and
an ejector for ejecting tissue from the hollow probe, wherein
the ejector is arranged axially displaceably within the cavity.

34. The surgical probe of claim 33, wherein:
the ejector is arranged displaceably out of a rest position at one end of the cavity in the direction of the cavity and on a side thereof towards the cavity in the rest position carries a severing blade which is towards the cavity.

35. The surgical probe of claim 33, wherein:
the cutting element and the ejector are fixed to a common thrust rod which is guided longitudinally slidably with respect to the segments.

36. A surgical probe for the minimally invasive removal of tissue, comprising:
an elongate hollow body comprising a first segment and a second segment, at least the first segment includes an open cavity for receiving tissue and the second segment engages the open cavity of the first segment to enclose a hollow space, the first and second segments being movable relative to each other to selectively open or close access to the hollow space;
a thrust rod guided in one of the two segments connects the two segments an electrically conductive cutting element comprising a ring-shaped or loop-shaped portion and a cutting arm portion connecting the loop portion to the thrust rod in an electrically conductive manner, wherein the cutting element is movable relative to at least one of the segments and which is adapted for electrosurgically cutting out tissue which has penetrated into an opening between the hollow body segments when the segments are in an open configuration.

* * * * *